(12) United States Patent  (10) Patent No.: US 7,842,484 B2
Lewis  (45) Date of Patent: Nov. 30, 2010

(54) METHOD FOR PRODUCING ETHANOL USING RAW STARCH

(75) Inventor: Stephen M. Lewis, Sioux Falls, SD (US)

(73) Assignee: Poet Research, Inc., Sioux Falls, SD (US)

( * ) Notice: Subject to any disclaimer, the term of this patent is extended or adjusted under 35 U.S.C. 154(b) by 788 days.

(21) Appl. No.: 11/676,965

(22) Filed: Feb. 20, 2007

(65) Prior Publication Data

US 2007/0196907 A1  Aug. 23, 2007

Related U.S. Application Data

(63) Continuation of application No. 10/798,226, filed on Mar. 10, 2004, now abandoned.

(60) Provisional application No. 60/453,442, filed on Mar. 10, 2003.

(51) Int. Cl.
*C12P 7/06* (2006.01)
*C12Q 1/54* (2006.01)
*C12Q 1/34* (2006.01)
*C12Q 1/40* (2006.01)
*C12C 11/00* (2006.01)
*C12C 11/07* (2006.01)
*C12C 11/11* (2006.01)

(52) U.S. Cl. .................. 435/161; 426/11; 426/14; 426/16; 435/14; 435/18; 435/22

(58) Field of Classification Search ............ None
See application file for complete search history.

(56) References Cited

U.S. PATENT DOCUMENTS

| | | | |
|---|---|---|---|
| 2,440,925 A | 5/1948 | Boeckeler |
| 3,940,492 A | 2/1976 | Ehnstrom |
| 4,009,074 A | 2/1977 | Walon |
| 4,092,434 A | 5/1978 | Yoshizumi et al. |
| 4,243,750 A | 1/1981 | Muller et al. |
| 4,279,747 A | 7/1981 | Chen |
| 4,287,303 A | 9/1981 | Dahlberg et al. |
| 4,309,254 A | 1/1982 | Dahlstrom et al. |
| 4,316,956 A | 2/1982 | Lutzen |
| 4,358,536 A | 11/1982 | Thorsson et al. |
| 4,376,163 A | 3/1983 | Ehnstrom |
| 4,460,687 A | 7/1984 | Ehnstrom |
| 4,474,883 A | 10/1984 | Yamamoto et al. |
| 4,490,469 A | 12/1984 | Kirby et al. |
| 4,514,496 A | 4/1985 | Yoshizumi et al. |
| 4,522,920 A | 6/1985 | Thorsson et al. |
| 4,540,663 A | 9/1985 | Witt |
| 4,591,560 A | 5/1986 | Kainuma et al. |
| 4,618,579 A | 10/1986 | Dwiggins et al. |
| 4,716,218 A | 12/1987 | Chen et al. |
| 4,727,026 A | 2/1988 | Sawada et al. |
| 4,760,025 A | 7/1988 | Estell et al. |
| 4,863,864 A | 9/1989 | Ashikari et al. |
| 4,876,196 A | 10/1989 | Salzbrunn et al. |
| 4,933,279 A | 6/1990 | Carroll et al. |
| 5,061,497 A | 10/1991 | Thacker et al. |
| 5,084,385 A | 1/1992 | Ashikari et al. |
| 5,087,417 A | 2/1992 | Dumbroff et al. |
| 5,180,669 A | 1/1993 | Antrim |
| 5,231,017 A | 7/1993 | Lantero et al. |
| 5,250,182 A | 10/1993 | Bento et al. |
| RE34,606 E | 5/1994 | Estell et al. |
| 5,322,778 A | 6/1994 | Antrim et al. |
| 5,364,770 A | 11/1994 | Berka et al. |
| 5,545,543 A | 8/1996 | Zinnamosca et al. |
| 5,559,031 A | 9/1996 | Zinnamosca et al. |
| 5,652,127 A | 7/1997 | Mitchinson et al. |
| 5,688,674 A | 11/1997 | Choi et al. |
| 5,721,127 A | 2/1998 | Deweer et al. |
| 5,721,128 A | 2/1998 | Deweer et al. |
| 5,736,375 A | 4/1998 | Deweer et al. |
| 5,736,499 A | 4/1998 | Mitchinson et al. |
| 5,756,714 A | 5/1998 | Antrim et al. |
| 5,817,498 A | 10/1998 | Deweer et al. |
| 5,824,532 A | 10/1998 | Barnett et al. |
| 5,849,549 A | 12/1998 | Barnett et al. |
| 5,958,739 A | 9/1999 | Mitchinson et al. |
| 5,981,237 A | 11/1999 | Meagher et al. |
| 6,074,854 A | 6/2000 | Deweer et al. |
| 6,136,576 A | 10/2000 | Diaz-Torres et al. |
| 6,171,817 B1 | 1/2001 | Berka et al. |
| 6,228,177 B1 | 5/2001 | Torget |
| 6,313,328 B1 | 11/2001 | Ulrich et al. |
| 6,423,145 B1 | 7/2002 | Nguyen et al. |
| 6,451,063 B1 | 9/2002 | Clarkson et al. |
| 6,509,180 B1 | 1/2003 | Verser et al. |
| 6,538,182 B1 | 3/2003 | Thompson et al. |
| 6,616,948 B2 | 9/2003 | Gustavsson et al. |
| 6,664,095 B1 | 12/2003 | Suryanarayan et al. |
| 6,774,284 B1 | 8/2004 | Thompson et al. |
| 6,803,218 B1 | 10/2004 | Seyfried et al. |
| 6,849,782 B2 | 2/2005 | Thompson et al. |
| 6,855,529 B2 | 2/2005 | Thompson et al. |
| 6,867,237 B1 | 3/2005 | Taylor et al. |

(Continued)

FOREIGN PATENT DOCUMENTS

DE  267508 A  *  5/1989

(Continued)

OTHER PUBLICATIONS

Han et al. (1987). Amylolysis of Raw Corn by *Aspergillus niger* for Simultaneous Ethanol Fermentation. Biotechnology and Bioengineering, vol. 30, pp. 225-232.*

(Continued)

*Primary Examiner*—Ralph Gitomer
*Assistant Examiner*—Kailash C Srivastava
(74) *Attorney, Agent, or Firm*—Swiss Tanner, P.C.

(57) ABSTRACT

Disclosed are methods for producing high levels of alcohol during fermentation of plant material, and to the high alcohol beer produced.

13 Claims, 25 Drawing Sheets

U.S. PATENT DOCUMENTS

| | | | |
|---|---|---|---|
| 6,878,860 | B1 | 4/2005 | Thompson et al. |
| 2003/0134395 | A1 | 7/2003 | Shetty et al. |
| 2003/0134396 | A1 | 7/2003 | Shetty et al. |
| 2003/0180900 | A1 | 9/2003 | Lanteo |
| 2003/0203454 | A1 | 10/2003 | Chpotani et al. |
| 2004/0023349 | A1 | 2/2004 | Bisgaard-Frantzen et al. |
| 2004/0043117 | A1 | 3/2004 | Cope et al. |
| 2004/0091983 | A1 | 5/2004 | Veit et al. |
| 2004/0157301 | A1 | 8/2004 | Chotani et al. |
| 2004/0192896 | A1 | 9/2004 | Finch |
| 2004/0197409 | A1 | 10/2004 | Iyer et al. |
| 2004/0219649 | A1 | 11/2004 | Olsen et al. |
| 2004/0234649 | A1 | 11/2004 | Lewis et al. |
| 2005/0026261 | A1 | 2/2005 | Otto et al. |
| 2005/0042737 | A1 | 2/2005 | Vikso-Nielsen et al. |
| 2005/0100996 | A1 | 5/2005 | Lantero, Jr. et al. |
| 2005/0136525 | A1 | 6/2005 | Baldwin et al. |
| 2005/0208623 | A1 | 9/2005 | Baldwin et al. |
| 2005/0233030 | A1 | 10/2005 | Lewis et al. |
| 2005/0239181 | A1 | 10/2005 | Lewis et al. |
| 2007/0178567 | A1* | 8/2007 | Lewis .................... 435/161 |
| 2007/0202214 | A1* | 8/2007 | Lewis et al. ............. 426/52 |
| 2010/0041116 | A1* | 2/2010 | Lewis et al. ............. 435/161 |

FOREIGN PATENT DOCUMENTS

| | | |
|---|---|---|
| EP | 0 140 410 | 5/1985 |
| EP | 0 171 218 | 2/1986 |
| JP | 58-005145 | 1/1983 |
| JP | 59-179093 | 10/1984 |
| WO | WO 92/20777 | 11/1992 |
| WO | WO 95/13362 | 5/1995 |
| WO | WO 97/27047 | 7/1997 |
| WO | WO03/066816 | 8/2003 |
| WO | WO 03/066826 | 8/2003 |
| WO | WO 03/068976 | 8/2003 |
| WO | WO 2004/081193 | 9/2004 |
| WO | WO 2004/081193 A2 | 9/2004 |
| WO | WO 2005/052148 | 6/2005 |
| WO | WO 2005/082155 | 9/2005 |

OTHER PUBLICATIONS

Weiss et al. Updated 2009 Distillers Grains—eXtension, pp. 1-6, Printed 05;08/1010.*
Minnesota Pollution Control Agency (i.e., MPCA) (2002). Ethanol Production in Minnesota. Air Quality/ General #1.20/ Oct. pp. 1-4.*
International Search Report dated Jun. 1, 2005.
Internal Search Report mailed Dec. 9, 2005.
Han, M. et al., "Saccharification and Ethanol Fermentation from Uncooked Starch Using *Aspergillus niger* Koji," *Korean J. Food Sci. Technol.*, vol. 17, No. 4,pp. 258-264 91985).
Suresh, K. et al., "Production of ethanol by raw starch hydrolysis and fermentation of damaged grains of wheat and sorghum," *Bioprocess Engineering*, vol. 21, pp. 165-168 (1999).
International Search Report mailed Sep. 15, 2006.
Kang, H. et al., "Effect of Initiation Factor eIF-5A Depletion on Protein Synthesis and Proliferation of *Saccharomyces cerevisiae*," *J. Biol. Chem.*, vol. 269, No. 6, pp. 3934-3940 (Feb. 11, 1994).
Schnier, J. et al., "Translation Initiation Factor 5A and its Hypusine Modification are Essential for Cell Viability in the yeast *Saccharomyces cerevisiae*," *Molecular and Cellular Biology*, vol. 11, No. 6, pp. 3105-3114 (Jun. 1991).
Civil Docket Sheet for Case No. 04-ev-4202 printed Jun. 23, 2006.
1, Complaint, filed by Broin and Associates, Inc., Entered: Dec. 15, 2004.
15-1, First Amended Complaint, filed by Broin and Associates, Inc. (Attachments: #1 Exhibit A—Press Release #2 Exhibit B—Magazine Article), Entered Jan. 25, 2005.
15-2, Press Release dated Nov. 4, 2004, *Broin Companies Announces Ethanol Technology Revolution.*
15-3, Swanson, *Company Spotlight: Patterning in Progress, Ethanol Producers Magazine*, pp. 62-68 (Dec. 2004).
16, First Motion to Expedite *Discovery and Supporting Brief* by Broin and Associates, Inc., Entered: Jan. 25, 2005.
17-1, Declaration of Jeffrey C. Brown regarding (16) First Motion to Expedite *Discovery and Supporting Brief*, Entered: Jan. 25, 2005.
17-6, Exhibit E of Docket No. 17, Plaintiff's First Set of Interrogatories to Defendant, Entered: Jan. 25, 2005.
50-1, Affidavit of Steven W. Sanford in Support of Defendant Genencor's Opposition to Motion for Summary Judgment, Entered Feb. 14, 2005.
50-6, Exhibit D of Docket No. 50, Jan. 10, 2005 letter from Mark Skoog to Ben Brown, Entered: Feb. 14, 2005.
52, Memorandum in Opposition regarding Docket No. 16, First Motion to Expedite Discovery and Supporting Brief, filed by Genencor International, Inc., Entered: Feb. 14, 2005.
53, Motion for Discovery, *Requiring Plaintiff to Specify Trade Secrets Prior to Commencement of Discovery and Supporting Brief*, b y Genencor International, Inc. Entered: Feb. 14, 2005.
54, Motion to Dismiss Pursuant to FRCP 12(b)(6); Motion for a More Definite Statement Pursuant to FRCP 12(e) and Supporting Brief, by Genencor International, Inc., Entered: Feb. 14, 2005.
61, Response to Motion regarding Docket No. 53, Motion for Discovery, *Requiring Plaintiff to Specify Trade Secrets Prior to Commencement of Discovery and Supporting Brief*, filed by Broin and Associates, Inc., Entered: Feb. 28, 2005.
62, Reply to Motion Response regarding Docket No. 16, First Motion to Expedite Discovery and Supporting Brief, filed by Broin and Associates, Inc., Entered: Mar. 1, 2005.
67, Reply to Motion Response regarding Docket No. 53, Motion for Discovery, *Requiring Plaintiff to Specify Trade Secrets Prior to Commencement of Discovery and Supporting Brief*, filed by Genencor International, Inc. Entered: Mar. 2, 2005.
68, Form 35 Report of parties Planning Meeting and Scheduling Information, Entered: Mar. 3, 2005.
77, Memorandum in Opposition regarding Docket No. 54, Motion to Dismiss Pursuant to FRCP 12(b)(6); Motion for a More Definite Statement Pursuant to FRCP 12(e) and Supporting Brief, filed by Broin and Associates, inc. Entered: Mar. 9, 2005.
85, Reply to Motion Response regarding Docket No. 54, Motion to Dismiss Pursuant to FRCP 12(b0(6); Motion for a More Definite Statement Pursuant to FRCP 12(e) and Supporting Brief, filed by Genencor International, Inc., Entered: Mar. 23, 2005.
90, Response to Docket No. 87 Brief, *Regarding Genencor's Objections to Broin's Identification of Trade Secrets*, filed by Broin and Associates, inc., Entered: Apr. 11, 2005.
95, Form 35 Report of Parties Planning Meeting *and Scheduling information*, Entered: Apr. 18, 2005.
102, Genencor's Notice to Take Deposition of Novozymes North America, Inc., Entered May 2, 2005.
112, Transcript of Proceedings held on Mar. 4, 2005 regarding Docket No. 69, motion Hearing, Entered: May 13, 2005.
132, Memorandum Opinion and Order regarding Docket No. 54, denying in part Motion to Dismiss as to Counts III, IV, V, and VIII and granting without prejudice to Plaintiff's right to amend as to Counts VI and VII, denying Docket No. 54, Motion for a more Definite Statement Signed by Judge Lawrence L. Piersol on Jul. 26, 2005, Entered: Jul. 26, 2005.
138, Genencor International, Inc.'s Answer to Amended Complaint and Counterclaim against Broin and Associates, Inc., by Genencor International, inc. Entered: Aug. 29, 2005.
148, Reply to Docket No. 138, Answer to Amended Complaint and Counterclaim against filed by Broin and Associates, Inc., Broin and Associates, Inc. Entered: Sep. 20, 2005.
153, Memorandum in Support regarding Docket No. 152, Motion to dismiss First Amended Complaint Based on Intentional Violations of Protective Order filed by Genencor International, Inc. (Sanford, Steven) (Entered: Sep. 30, 2005).
"Determination of acid or-Amylase activity, FIA", SOP No. EB-SM-0259.01/01 pp. 1-14 (Internet Mar. 2003).
"Determination of Amyloglucosidase Activity using the Auto Analyzer", Novozymes Analytical Method EB-SM-0131.02/01 (Internet Mar. 2003).
"Spirizyme Plus for ethanol production", Novozymes Application Sheet Ethanol/2002-03379-03.pdf (Internet Mar. 2003).

Bardini, G. et al., "Continuous clarification of grape must by flotation," *Vini d'italia*, vol. 34, No. 1 pp. 31-38 (1992)(1 page Abstract).

Biotimes: The enzyme e-zine, "Fuel Ethanol Products" (Jan. 2003).

Carlson, M., "Distillers ByProducts for Swine Diets", *Missouri Value Added Development Center* (Internet Mar. 2003).

PCT2005US008155 International Search Report Dated Nov. 30, 2005 and Written Opinion.

Farid, M. et al., "Alcohol production from starch by mixed cultures of *Aspergillus awamori* and immobilized *Saccharomyces cerevisiae* a different agitation speeds", *J. Basic Microbio*, 42(3):162-71 (2002) (Abstract only).

Honeyman et al., "Evaluation of a Distillers Dried Grain Derivative Feedstuff on Performance of Nursery Pigs", *Iowa State University* (Internet Mar. 2003).

Makarov, O. et al. "Quality improvement of table wines following continuous clarification treatments," Kharachova Promislovist (1976)(1 page Abstract).

Shleser, R., Ethanol Production in Hawaii: Processes, Feedstocks, and Current Economic Feasibility of Fuel Grade Ethanol Produciton in Hawaii *Hawaii State Department of Business, Economic Development & Tourism*, Final Report (Jul. 1994).

Shurson, J., "Overview of Swine Nutrition Research on the Value and Application of Distiller's Dried Grains with Solubles Produced by Minnesota and South Dakota Ethanol Plants", pp. 1-40 (Internet Mar. 2003).

The fuel of the future, *Novozymes* (May 2002).

Waxy Corn, *U.S. Grains Council*, pp. 1-8 (Internet Mar. 2003).

Weigel et al., "Feed Co-Products of the Dry Corn Milling Process", *Feed Co-Products Handbook*, pp. 1-13 (Internet Mar. 2003).

PCT Patent Title Word Search, Genencor Assignee, Oct. 4, 2005.

Genencor Inventor Search, Oct. 3, 2005.

Patent Title Word Search, Sep. 28, 2005.

Bryan, "Changing the Game", *Ethanol Producer Magazine*, pp. 58-63 (Aug. 2005).

Narita et al., "Efficient Production of L-(+)-Lactic Acid from Raw Starch by *Streptococcus bovis* 148" *Journal of Bioscience and Bioengineering*, vol. 97, No. 6, 423-425 (2004).

Casey et al., "Reevaluation of Alcohol Synthesis and Tolerance on Brewer's Yeast", American Society of Brewing Chemists, Inc., vol. 43, No. 2, pp. 75-83 (1985).

Jones, "review: Biological principles for the effects of ethanol", *Enzyme Microb. Technol.*, vol. 11, pp. 130-153 (Mar. 1989).

Van Uden et al., "Effects of ethanol on yeast performance; targets and underlying mechanisms". *European Brewery Convention*, Proceeding of the 19$^{th}$ Congress, London (1983) pp. 137-144.

GCOR Lantero patent application search USPTO site.5.17.05.

Rosentrater, "Understanding Distillers Grain Storage, Handling and Flowability Challenges", *Distillers Grain Quarterly*, First Quarter 2006, pp. 18-21.

Jacques et al., *The Alcohol Textbook, 3$^{rd}$ Edition*, A reference for the beverage, fuel and industrial alcohol industries, Nottingham University Press 1999, Alltech Inc. 1999 (386 pages).

Jacques et al., *The Alcohol Textbook, 4$^{th}$ Edition*, A reference for the beverage, fuel and industrial alcohol industries, Nottingham University Press 2003 Alltech Inc. 203 (446 pages).

Allison et al., "Transformation of the thermophilic fungus *Humicola grisea* var. *thermoidea* and overproduction of *Humicola glucoamylase*", *Curr Genet* (1992) 21:225-229.

Ashikari et al., "*Rhizopus* Raw-Starch-Degrading Glucoamylase: Its Cloning and Expression in Yeast". *Agric. Bio. Chem.* 50(4), 957-964 (1986).

Belya et al., "Composition of corn and distillers dried grains with solubles from dry grind ethanol processing", *Bioresource Technology* 94 (2004) 293-298.

Biswas et al., "Analysis of Headspace Compounds of Distillers Grains using SPME in Conjunction with GC/MS and TGA", *Journal of Cereal Science*, 33(2001) 223-229.

Boel et al., "Glucoamylases G1 and G2 from *Aspergillus niger* are synthesized from two different but closely related mRNAs", *The EMBP Journal*, vol. 3, No. 5 pp. 1097-1102 (1984).

Chen et al., "Effect of replacing helical glycine residues with alanines on reversible and irreversible stability and production of *Aspergillus awamori* glucoamylase", *Protein Engineering*, vol. 9, No. 6, pp. 499-505 (1996).

Dettori-Campus et al., "Hydrolysis of Starch Granules by the Amyase from *Bacillus stearothermophilus* NCA 26", *Process Biochemistry*, 27 (1992) 17-21.

Han et al., "Amyloysis of raw corn by *Aspergillus niger* from simultaneous ethanol fermentation", *Biotechnology and Bioengineering*, vol. 30 pp. 225-232 (1987).

Hayashida et al., "High Concentration-Ethanol Fermantation of Raw Ground Corn", *Agric. Biol. Chem.*, 46(7), 1947-1950 (1982).

Hayashida et al., "Molecular cloning of Glucoamylase 1 Gene of *Aspergillus awamori* var. *kawachi* for Localization of the Raw-starch-affinity Site", *Agric. Biol. Chem.*, 53(4), 923-929 (1989).

Jensen et al., "Purification of extracellular amylolytic enzymes from the thermophilic fungus *Thermomyces lanuginosus*", *Can. J. Microbiol.*, vol. 34, 218-223 (1988).

Joutsjoki et al., "A Novel Glucoamylase Preparation for Grain Mash Saccharification", *Biotechnology Letters*, vol. 15, No. 3, pp. 227-282 (Mar. 1993).

Lang et al., "Recycle Bioreactor for Bioethanol Production from Wheat Starch II. Fermentation and Economics", *Energy Sources*, 23:427-436 (2001).

Lutzen, "Enzyme Technology in the Production of Ethanol—Recent Process Development". *Advances in Biotechnology*, vol. II: *Fuels, Chemicals, Foods and Waste Treatment*, 1981 Pergamon Pres Canada Ltd., pp. 161-167.

Matsumoto et al., "Industrialization of a Noncooking System for Alcoholic Fermantation from Grains", *Agric. Biol. Chem.* 46(6): 1549-1558 (1982).

Matsuoka et al., "Alcoholic Fermentation of Sweet Potato without Cooking", *J. Ferment. Technol.*, vol. 60, No. 6, pp. 599-602 ) (1982).

Morris, et al., "AFM Images of Complexes between Amylose and *Aspergillus niger* Glucoamylase Mutants, Native and Mutant Starch Binding Domains: A Model for the Action of glucoamylase", *Starch/Starke*, 57:1-7 (2005).

Narendranath et al., "Acetic Acid Lacti Acid Inhibition of Growth of *Saccharomyces cerevisiac* b Different Mechanisms", *American Society of Brewing Chemists, Inc.* 59(4): 187-194 (2001).

Narendranath et al., "Effect of yeast inoculation rate on the metabolism of contaminating lactobailli during fermentation of corn mash", *J. Ind. Microbiol. Biotechnol.* 31:581-584 (2004).

Narendranath et al., "Effects of acetic acid lactic acid on the growth of *Saccharomyces cerevisiae* in minimal medium", *Journal of Industrial Microbiology & Biotechnology*, 26: 171-177 (2001).

Narendranath et al., "Effects of Lactobacilli on Yeast-Catalyzed Ethanol Fermentations", *Applied and Environmental Microbiology*, vol. 60, No. 11, p. 4158-4163 (Nov. 1997).

Neelakantam et al., "Relationship between pH and Medium Dissolved Solids in Terms of Growth and Metabolism of Lactobacilli and *Saccharomyces cerevisiae* during Ethanol Production", *Applied and Environmental Microbiology*, vol. 71, No. 5, p. 2239-2243 (May 2005).

Narendranath et al., "Urea hydrogen Peroxide Reduces the Number of Laactobacilli Nourishes Yeast, and Leaves No Residues in the Ethanol Fermentation", *Applied and Environmental Microbiology*, vol. 66, No. 10, p. 4187-4192 (Oct. 2000).

Porter et al., "Variability in Soy Flour Composition", *JAOCS*, vol. 80, No. 6, pp. 557-562 (2003).

Shibuya et al., "Molecular Cloning of the Glucoamylase Gene of *Aspergillus shirousami* and its Expression in *Aspergillus oryzae*", *Agric. Biol. Chem.*, 54(8): 1905-1914 (1990).

Sigmund et al., "The Economics of Fair Play", *Scientific American*, pp. 83-87 (Jan. 2002).

Taylor et al., "Some Properties of a Glucoamylase produced by the Thermophilic Fungus *Humicola lanuginose*", *Carbohydrate Research*, 61:301-308 (1978).

Thammarutwasik et al., "Alcoholic Fermentation of Sorghum Without Cooking", *Biotechnology and Bioengineering*, vol. 28 pp. 1122-1125 (Jul. 1986).

Tosi et al., "Purification and characterization of an extracellular glucoamylase from the thermophilic fungus *Humicola grisea* var. *thermoidea*", *Can J. Microbiol.*, vol. 39, pp. 846-852 (1993).

Ueda et al., "Alchoholic Fermentation of Raw Starch without Cooking by Using Back-*koji* Amylase", *J. Ferment. Technol.*, vol. 58, No. 3, p. 237-242 (1980).

Ueda et al., "Direct hydrolysis of raw starch", *Microbiological Sciences*, vol. 1, No. 1, pp. 21-24 (1984).

Ueda, "Ethanol Fermentation of Starch Materials without Cooking", *J. Jap. Soc. Starch Sci.*, 29(2):123-130 (1982), (English Abstract).

Weller et al., "Fuel Ethanol from Raw Corn by *Aspergilli* Hydrolysis with Concurrent Yeast Fermentation", *Biotechnology and Bioengineering Symp.*, No. 13, pp. 437-447 (1983).

Thomas et al., "Fuel Alcohol Production: Effects of Free Amino Nitrogen on Fermentation of Very-High-Gravity Wheat Mashes", *Applied and Environmental Microbiology*, vol. 56, No. 7, p. 2046-2050 (Jul. 1990).

McAloon et al., "Determining the Cost of Producing Ethanol from Corn Starch and Lignocellulosic Feedstocks", *Technical Report NREL TP-580-28893*, (Oct. 2000) www.doe.gov/bridge.

McLean et al., "Fluorometric Method for Measuring Yeast Metabolic Activity", *Technical Report*, 3:5-25 (2002).

McLean et al. A Novel Method for Quantitation of Active Yeast Cells, *Technical Report*, 3;5-25 (2002).

Yue et al., Functionality of resistant starch in food applications:, National Starch & Chemical (reprinted from Dec. 1998 issue of Food Australia) (1999).

Hamdy et al., "Effects of virginiamycin on Fermentation Rate by Yeast", *Biomass and Bioenergy*, vol. 11, No. 1 pp. 1-9 (1996).

Islam et al., "Stability of virginiamycin and penicillin during alcohol fermentation", *Biomass and Bioenergy*, 17: 369-376 (1999).

Daugulis et al., "The Economics of Ethanol Production by Extractive Fermentation", *The Canadian J. of Chemical Engineering*, vol. 69, pp. 48-497 (Apr. 1991).

"SIU Edwardsville National Corn to Ethanol Research Pilot Plant Process Description", Project No. 24307-78188, Washington group Nov. 12, 2001.

"Ready for Research", *BioFuels Journal*, pp. 20-23 (4Q04).

Bothast, "Ethanol research facility one of a kind", *Industrial Oil Products Article*, vol. 15(8):518-519 (Aug. 2004).

Tritto et al., "2 grants, 6 clients boot yields at ethanol center", *St. Louis Business Journal*, Nov. 26-Dec. 2, 2004.

Fujio et al., "Ethanol Fermentation of Raw Cassava Starch with *Rhizopus koji* in a Gas Circulation Type Fermentor", *Biotechnology and Bioengineering*, vol. 27:1270-1273, Aug. 1985.

Swanson, Company Spotlight, "Partnering in Progress", *Ethanol Producer Magazine*, pp. 62-68, Dec. 2004.

Argus Leader.Com., Web Page—Business—Broin Goes to Court, Printed Jun. 27, 2006, pp. 1-3.

Springer Link-Article, Web Page—Article—Natural Resources—"Ethanol Fuels: Energy Balance, Economics, and Enviornmental Impacts Are Negative", Printed Jul. 5, 2005, pp. 1-2.

Berven, "The Making of Broin Project X", *Ethanol Producer Magazine*, Feb. 2005, pp. 66-71.

"Grain Processing Enzymes for Sweetener Production", *Genencor International*. Apr. 2004, pp. 1-3.

"NOVELOSE" Resistant Starch—The starch that thinks it's a fiber, *National Starch and Chemical Compnay*, 2003.

"Enzymatic modification of starch granules: peeling off versus porosity", *TNO Nutrition and Food Research*, Dec. 28, 2000, ppp. 1-2.

"Nutrient composiiton of DDGS (100% dry matter basis) from various reference—Table 1", *Distillers Grains Quarterly*, First Quarter 2006, pp. 27-28.

"Very High Gravity Technology", *Ethanol Producer Magazine*, Jan. 2006.

Saha et al., Raw Starch Absorption, Elution and Digestion behavior of Glucoamylase of *Rhizopus niveus, J. Ferment. Technol.*, vol. 61, No. 1, p. 67-72, 1983.

Hayashida et al., Raw Starch-digestive Glucoamulase Productivity of Protease-less Mutant from *Asoergukkys awaniru* var. *kawachi, Agric. Biol. Chem.*, 45(12)m p. 2675-2681, 1981.

Norman et al., "Process Considerations for the Production of Ethanol from Cereals", *Novo Research Institute—Denmark*, p. 1-15, Date Unknown.

Fujio et al., Alcohol Fermentation of Raw Cassava Starch by *Rhizopus koji* without cooking. *Biotechnology and Bioengineering*, vol. XXVI, p. 315-319, 1984.

Mikuni et al., "Alcohol Fermentation of Corn Starch Digested by Chalara paradoxa Amylase without Cooking", *Biotechnology and Bioengineering*, vol. XXIX, p. 729-732 1987.

Brown et al., "The effect of temperature on the ehtanol tolerance of the yeast, *Saccharomyces uvarum*", *Biotechnology Letters*, vol. 4, 269-274 (1982).

Aldrich. "New Enzymes Lower Ethanol Production Fuel Costs", *BridgeNews*, Kansas City, Apr. 4, 2004.

Barr-Rosin. "Fluidised Bed Dryers and Coolers." *GEA*. www.barr-rosin.com/english/pdf/fluid.pdf.

Knott et al. "Effects of the Nutrient Variability of Distiller's Solubles and Grains within Ethanol Plants and the Amount of Distiller's Solubles Blended with Distiller's Grains on Fat, Protein and Phosphorus Content of DDGS." 2004.

Knott et al. "Variation in Particle Size and Bulk Density of Distiller's Dried Grains with Solubles (DDGS) Produced by 'New Generation' Ethanol Plants in Minnesota and South Dakota." 2004.

Naidu Beesabathuni. "Effect of Corn Flour Particle Size on Ethanol Yield and Soluble Solids in Thin Stillage in a Dry Grind Process." *American Society of Agricultural and Biological Engineers*, Paper No. 036067, 2003.

Shurson. "The Value of High-Protein Distillers Coproducts in Swine Feeds." *Distillers Grains Quarterly*, First Quarter, pp. 22-25, 2006.

Wang. "Argonne National Laboratory Ethanol Study: Key points." *Office of Energy Efficiency and Renewal Energy—U.S. Department of Energy*, pp. 1-3, 2005.

www.nrel.gov/docs/fy02osti/31195.pdf, Biofuels News, vol. 4, No. 3, Fall 2001.

* cited by examiner

US 7,842,484 B2

METHOD FOR PRODUCING ETHANOL USING RAW STARCH

CROSS-REFERENCE TO RELATED APPLICATIONS

This application claims priority to U.S. patent application Ser. No. 10/798,226, filed Mar. 10, 2004, abandoned Feb. 20, 2007, which claims priority to Provisional Application Ser. No. 60/453,442 filed Mar 10, 2003.

FIELD OF THE INVENTION

The present invention relates to methods for producing high levels of alcohol during fermentation of plant material, and to the high alcohol beer produced. The present invention also relates to methods for producing high protein distiller's dried grain from fermentation of plant material, and to the high protein distiller's dried grain produced. The present invention further relates to reduced stack emissions from drying distillation products from the production of ethanol.

BACKGROUND OF THE INVENTION

Numerous conventional methods exist for converting plant material to ethanol. However, these methods suffer from numerous inefficiencies. There remains a need for additional more effective methods for converting plant material to ethanol and for producing improved fermentation products.

SUMMARY OF THE INVENTION

The present invention relates to methods for producing high levels of alcohol during fermentation of plant material, and to the high alcohol beer produced. The present invention also relates to methods for producing high protein distiller's dried grain from fermentation of plant material, and to the high protein distiller's dried grain produced.

In an embodiment, the present invention relates to a process for producing ethanol from plant material. This method includes grinding the plant material to produce ground plant material including starch; saccharifying the starch, without cooking; fermenting the incubated starch; and recovering the ethanol from the fermentation. The present method can include varying the temperature during fermentation. The present method can include employing a plant material with a particle size such that more than 50% of the material fits though a sieve with a 0.5 mm mesh. The present method can yield a composition including at least 18 vol-% ethanol.

In an embodiment, the present invention relates to a process for producing high protein distiller's dried grain from plant material. This method includes grinding the plant material to produce ground plant material including starch; producing sugars from the starch without cooking; fermenting the uncooked sugars to yield a composition including ethanol; and recovering distiller's dried grain from the fermentation. The distiller's dried grain can include at least about 30% protein. The distillers dried grain can include increased levels of the protein zein.

In an embodiment, the present invention relates to a process of producing ethanol from corn. This process includes producing starch from corn and ethanol from the starch; producing dryer stack emissions including a significantly lower level of volatile organic compounds than conventional technologies.

DETAILED DESCRIPTION OF THE INVENTION

Definitions

Figure 1A:
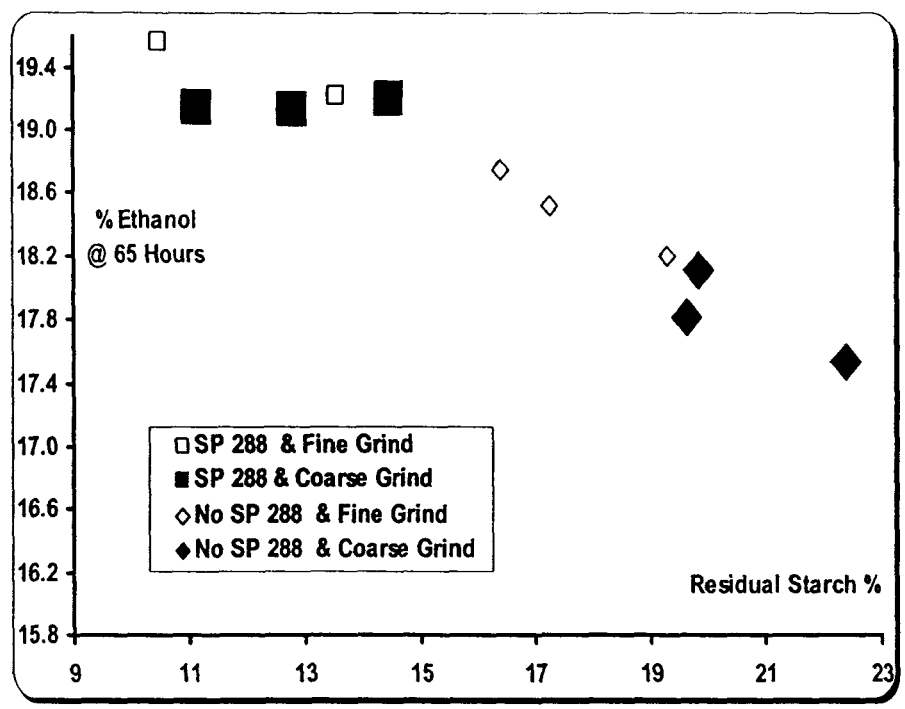
FIGS. 1A-E illustrate a comparison of the yield of the process of the present invention compared to a convention process.

As used herein, the phrase "without cooking" refers to a process for converting starch to ethanol without heat treatment for gelatinization and dextrinization of starch using alpha-amylase. Generally, for the process of the present invention, "without cooking" refers to maintaining a temperature below starch gelatinization temperatures, so that saccharification occurs directly from the raw native insoluble starch to soluble glucose while bypassing conventional starch gelatinization conditions. Starch gelatinization temperatures are typically in a range of 57° C. to 93° C. depending on the starch source and polymer type. In the method of the present invention, dextrinization of starch using conventional liquefaction techniques is not necessary for efficient fermentation of the carbohydrate in the grain.

As used herein, the phrase "plant material" refers to all or part of any plant (e.g., cereal grain), typically a material including starch. Suitable plant material includes grains such as maize (corn, e.g., whole ground corn), sorghum (milo), barley, wheat, rye, rice, and millet; and starchy root crops, tubers, or roots such as sweet potato and cassava. The plant material can be a mixture of such materials and byproducts of such materials, e.g., corn fiber, corn cobs, stover, or other cellulose and hemicellulose containing materials such as wood or plant residues. Suitable plant materials include corn, either standard corn or waxy corn.

As used herein, the terms "saccharification" and "saccharifying" refer to the process of converting starch to smaller polysaccharides and eventually to monosaccharides, such as glucose. Conventional saccharification uses liquefaction of gelatinized starch to create soluble dextrinized substrate which glucoamylase enzyme hydrolyzes to glucose. In the present method, saccharification refers to converting raw starch to glucose with enzymes, e.g., glucoamylase and acid fungal amylase (AFAU). According to the present method, the raw starch is not subjected to conventional liquefaction and gelatinization to create a conventional dextrinized substrate.

As used herein, a unit of acid fungal amylase activity (AFAU) refers to the standard Novozymes units for measuring acid fungal amylase activity. The Novozymes units are described in a Novozymes technical bulletin SOP No.: EB-SM-0259.02/01. Such units can be measured by detecting products of starch degradation by iodine titration. 1 unit is defined as the amount of enzyme that degrades 5.260 mg starch dry matter per hour under standard conditions.

As used herein, a unit of glucoamylase activity (GAU) refers to the standard Novozymes units for measuring glucoamylase activity. The Novozymes units and assays for determining glucoamylase activity are described in a publicly available Novozymes technical bulletin.

As used herein, a unit of amyloglucosidase activity (AGU) refers to the standard Novozymes units for measuring amyloglucosidase activity. The Novozymes units are described in a Novozymes technical bulletin SOP No.: EB-SM-0131.02/01. Such units can be measured by detecting conversion of maltose to glucose. The glucose can be determined using the glucose dehydrogenase reaction. 1 unit is defined as the amount of enzyme that catalyzes the conversion of 1 mmol maltose per minute under the given conditions.

As used herein, the term "about" modifying any amount refers to the variation in that amount encountered in real world conditions of producing sugars and ethanol, e.g., in the lab, pilot plant, or production facility. For example, an amount of an ingredient employed in a mixture when modified by "about" includes the variation and degree of care typically employed in measuring in an ethanol production plant or lab. For example, the amount of a component of a product when modified by "about" includes the variation between batches in an ethanol production plant or lab and the variation inherent in the analytical method. Whether or not modified by "about," the amounts include equivalents to those amounts. Any quantity stated herein and modified by "about" can also be employed in the present invention as the amount not modified by "about."

Converting Starch to Ethanol

The present invention relates to methods for producing high levels of alcohol during fermentation of plant material, and to the high alcohol beer produced. The present invention also relates to methods for producing high protein distiller's dried grain from fermentation of plant material, to the high protein distiller's dried grain produced, and to the cleaner dryer stack emissions.

The present method converts starch from plant material to ethanol. In an embodiment, the present method can include preparing the plant material for saccharification, converting the prepared plant material to sugars without cooking, and fermenting the sugars.

The plant material can be prepared for saccharification by any a variety of methods, e.g., by grinding, to make the starch available for saccharification and fermentation. In an embodiment, the vegetable material can be ground so that a substantial portion, e.g., a majority, of the ground material fits through a sieve with a 0.1-0.5 mm screen. For example, in an embodiment, about 70% or more, of the ground vegetable material can fit through a sieve with a 0.1-0.5 mm screen. In an embodiment, the reduced plant material can be mixed with liquid at about 20 to about 50 wt-% or about 25 to about 45 wt-% dry reduced plant material.

The present process can include converting reduced plant material to sugars that can be fermented by a microorganism such as yeast. This conversion can be effected by saccharifying the reduced plant material with an enzyme preparation, such as a saccharifying enzyme composition. A saccharifying enzyme composition can include any of a variety of known enzymes suitable for converting reduced plant material to fermentable sugars, such as amylases (e.g., α-amylase and/or glucoamylase). In an embodiment, saccharification is conducted at a pH of about 6.0 or less, for example, about 4.5 to about 5.0.

The present process includes fermenting sugars from reduced plant material to ethanol. Fermenting can be effected by a microorganism, such as yeast. In an embodiment, fermentation is conducted at a pH of about 6 or less, for example, about 4.5 to about 5. In an embodiment, the present method can include varying the pH. For example, fermentation can include filling the fermenter at pH of about 3 to about 4.5 during the first half of fill and at a pH of about 4.5 to about 6 during the second half of the fermenter fill cycle. In an embodiment, fermentation is conducted at a temperature of about 25 to about 40° C. or about 30 to about 35° C. In an embodiment, during fermentation the temperature is decreased from about 40° C. to about 30° C. or about 25° C., or from about 35° C. to about 30° C., during the first half of the fermentation, and the temperature is held at the lower temperature for the second half of the fermentation. In an embodiment, fermentation is conducted for about to 25 (e.g., 24) to about to 150 hours, for example, for about 48 (e.g., 47) to about 96 hours.

The present process can include simultaneously converting reduced plant material to sugars and fermenting those sugars with a microorganism such as yeast.

The product of the fermentation process is referred to herein as "beer". Ethanol can be recovered from the fermentation mixture, from the beer, by any of a variety of known processes, such as by distilling. The remaining stillage includes both liquid and solid material. The liquid and solid can be separated by, for example, centrifugation.

Preparing the Plant Material

The present method converts starch from plant material to ethanol. The plant material can be reduced by a variety of methods, e.g., by grinding, to make the starch available for saccharification and fermentation. Other methods of plant material reduction are available. For example, vegetable material, such as kernels of corn, can be ground with a ball mill, a roller mill, a hammer mill, or another mill known for grinding vegetable material, and/or other materials for the purposes of particle size reduction. The use of emulsion technology, rotary pulsation, and other means of particle size reduction can be employed to increase surface area of plant material while raising the effectiveness of flowing the liquefied media. The prepared plant material can be referred to as being or including "raw starch".

A fine grind exposes more surface area of the plant material, or vegetable material, and can facilitate saccharification and fermentation. In an embodiment, the vegetable material is ground so that a substantial portion, e.g., a majority, of the ground material fits through a sieve with a 0.1-0.5 mm screen. In an embodiment, about 35% or more of the ground vegetable material can fit through a sieve with a 0.1-0.5 mm screen. In an embodiment, about 35 to about 70% of the ground vegetable material can fit through a sieve with a 0.1-0.5 mm screen. In an embodiment, about 50% or more of the ground vegetable material can fit through a sieve with a 0.1-0.5 mm screen. In an embodiment, about 90% of the ground vegetable material can fit through a sieve with a 0.1-0.5 mm screen. In an embodiment, all of the ground vegetable material can fit through a sieve with a 0.1-0.5 mm screen.

Fractionation

In an embodiment, the vegetable material can be fractionated into one or more components. For example, a vegetable material such as a cereal grain or corn can be fractionated into components such as fiber (e.g., corn fiber), germ (e.g., corn germ), and a mixture of starch and protein (e.g., a mixture of corn starch and corn protein). One or a mixture of these components can be fermented in a process according to the present invention. Fractionation of corn or another plant material can be accomplished by any of a variety of methods or apparatus. For example, a system manufactured by Satake can be used to fractionate plant material such as corn.

Saccharification

The present process can include converting reduced plant material to sugars that can be fermented by a microorganism such as yeast. This conversion can be effected by saccharifying the reduced plant material with any of a variety of known saccharifying enzyme compositions. In an embodiment, the saccharifying enzyme composition includes an amylase, such as an alpha amylase (e.g., acid fungal amylase). The enzyme preparation can also include glucoamylase. The enzyme preparation need not, and, in an embodiment, does not include protease. However, ethanol production methods according to the present invention can conserve water by reusing process waters (backset) which may contain protease. In an embodiment, the present method employs acid fungal amylase for hydrolyzing raw starch.

Saccharifying can be conducted without cooking. For example, saccharifying can be conducted by mixing source of saccharifying enzyme composition (e.g., commercial enzyme), yeast, and fermentation ingredients with ground grain and process waters without cooking.

In an embodiment, saccharifying can include mixing the reduced plant material with a liquid, which can form a slurry or suspension and adding saccharifying enzyme composition (e.g., at least one of acid fungal amylase and glucoamylase) to the liquid. In an embodiment, the method includes mixing the reduced plant material and liquid and then adding the saccharifying enzyme composition (e.g., at least one of acid fungal amylase and glucoamylase). Alternatively, adding enzyme composition can precede or occur simultaneously with mixing.

In an embodiment, the reduced plant material can be mixed with liquid at about 20 to about 50 wt-%, about 25 to about 45 (e.g., 44) wt-%, about 30 to about 40 (e.g., 39) wt-%, or about 35 wt-% dry reduced plant material. As used herein, wt-% of reduced plant material in a liquid refers to the percentage of dry substance reduced plant material or dry solids. In an embodiment, the method of the present invention can convert raw or native starch (e.g., in dry reduced plant material) to ethanol at a faster rate at higher dry solids levels compared to conventional saccharification with cooking. Although not limiting to the present invention, it is believed that the present method can be practiced at higher dry solids levels because, unlike the conventional process, it does not include gelatinization, which increases viscosity.

Suitable liquids include water and a mixture of water and process waters, such as stillage (backset), scrubber water, evaporator condensate or distillate, side stripper water from distillation, or other ethanol plant process waters. In an embodiment, the liquid includes water. In an embodiment, the liquid includes water in a mixture with about 1 to about 70 vol-% stillage, about 15 to about 60 vol-% stillage, about 30 to about 50 vol-% stillage, or about 40 vol-% stillage.

In the conventional process employing gelatinization and liquefaction, stillage provides nutrients for efficient yeast fermentation, especially free amino nitrogen (FAN) required by yeast. The present invention can provide effective fermentation with reduced levels of stillage and even without added stillage. In an embodiment, the present method employs a preparation of plant material that supplies sufficient quantity and quality of nitrogen for efficient fermentation under high gravity conditions (e.g., in the presence of high levels of reduced plant material). Thus, in an embodiment, no or only low levels of stillage can suffice.

However, the present method provides the flexibility to employ high levels of stillage if desired. The present method does not employ conventional liquefaction. Conventional liquefaction increases viscosity of the fermentation mixture and the resulting stillage. The present method produces lower viscosity stillage. Therefore, in an embodiment, increased levels of stillage can be employed in the present method without detrimental increases in viscosity of the fermentation mixture or resulting stillage.

Further, although not limiting to the present invention, it is believed that conventional saccharification and fermentation processes require added FAN due to undesirable "Maillard Reactions" which occur during high temperature gelatinization and liquefaction. The Maillard Reactions consume FAN during cooking. As a result, the conventional process requires adding stillage to increase levels of FAN in fermentation. It is believed that the present process avoids temperature induced Maillard Reactions and provides increased levels of FAN in the reduced plant material, which are effectively utilized by the yeast in fermentation.

Saccharification can employ any of a variety of known enzyme sources (e.g., a microorganism) or compositions to produce fermentable sugars from the reduced plant material. In an embodiment, the saccharifying enzyme composition includes an amylase, such as an alpha amylase (e.g., acid fungal amylase) or a glucoamylase.

In an embodiment, saccharification is conducted at a pH of about 6.0 or less, pH of about 3.0 to about 6.0, about 3.5 to about 6.0, about 4.0 to about 5.0, about 4.0 to about 4.5, or about 4.5 to about 5.0. The initial pH of the saccharification mixture can be adjusted by addition of, for example, ammonia, sulfuric acid, phosphoric acid, process waters (e.g., stillage (backset), evaporator condensate (distillate), side stripper bottoms, and the like), and the like. Activity of certain saccharifying enzyme compositions (e.g., at least one of acid fungal amylase and glucoamylase) can be enhanced at pH lower than the above ranges.

In an embodiment, saccharification is conducted at a temperature of about 25 to about 40° C. or about 30 to about 35° C.

In an embodiment, saccharifying can be carried out employing quantities of saccharifying enzyme composition (e.g., at least one of acid fungal amylase and glucoamylase) selected to maintain low concentrations of dextrin in the fermentation broth. For example, the present process can employ quantities of saccharifying enzyme composition (e.g., at least one of acid fungal amylase and glucoamylase) selected to maintain maltotriose (DP3) at levels at or below about 0.2 wt-% or at or below about 0.1 wt-%. For example, the present process can employ quantities of saccharifying enzyme composition (e.g., at least one of acid fungal amylase and glucoamylase) selected to maintain dextrin with a degree of polymerization of 4 or more (DP4+) at levels at or below about 1 wt-% or at or below about 0.5 wt-%. For maintaining low levels of maltotriose and/or DP4+, suitable levels of acid fungal amylase and glucoamylase include about 0.3 to about 3 AFAU/gram dry solids reduced plant material (e.g., DSC) of acid fungal amylase and about 1 to about 2.5 (e.g., 2.4) AGU per gram dry solids reduced plant material (e.g., DSC) of glucoamylase. In an embodiment, the reaction mixture includes about 1 to about 2 AFAU/gram dry solids reduced plant material (e.g., DSC) of acid fungal amylase and about 1 to about 1.5 AGU per gram dry solids reduced plant material (e.g., DSC) of glucoamylase.

In an embodiment, saccharifying can be carried out employing quantities of saccharifying enzyme composition (e.g., at least one of acid fungal amylase and glucoamylase) selected to maintain low concentrations of maltose in the fermentation broth. For example, the present process can employ quantities of saccharifying enzyme composition (e.g., at least one of acid fungal amylase and glucoamylase) selected to maintain maltose at levels at or below about 0.3 wt-%. For maintaining low levels of maltose, suitable levels of acid fungal amylase and glucoamylase include about 0.3 to about 3 AFAU/gram dry solids reduced plant material (e.g., DSC) of acid fungal amylase and about 1 to about 2.5 (e.g., 2.4) AGU per gram dry solids reduced plant material (e.g., DSC) of glucoamylase. In an embodiment, the reaction mixture includes about 1 to about 2 AFAU/gram dry solids reduced plant material (e.g., DSC) of acid fungal amylase and about 1 to about 1.5 AGU per gram dry solids reduced plant material (e.g., DSC) of glucoamylase.

Acid Fungal Amylase

In certain embodiments, the present method employs an a-amylase. The α-amylase can be one produced by fungi. The α-amylase can be one characterized by its ability to hydrolyze carbohydrates under acidic conditions. An amylase produced by fungi and able to hydrolyze carbohydrates under acidic conditions is referred to herein as acid fungal amylase, and is also known as an acid stable fungal a-amylase. Acid fungal amylase can catalyze the hydrolysis of partially hydrolyzed starch and large oligosaccharides to sugars such as glucose. The acid fungal amylase that can be employed in the present process can be characterized by its ability to aid the hydrolysis of raw or native starch, enhancing the saccharification provided by glucoamylase. In an embodiment, the acid fungal amylase produces more maltose than conventional (e.g., bacterial) α-amylases.

Suitable acid fungal amylase can be isolated from any of a variety of fungal species, including *Aspergillus, Rhizopus, Mucor, Candida, Coriolus, Endothia, Enthomophtora, Irpex,* *Penicillium, Sclerotium* and *Torulopsis* species. In an embodiment, the acid fungal amylase is thermally stable and is isolated from *Aspergillus* species, such as *A. niger, A. saitoi* or *A. oryzae*, from *Mucor* species such as *M. pusillus* or *M. miehei*, or from *Endothia* species such as *E. parasitica*. In an embodiment, the acid fungal amylase is isolated from *Aspergillus niger*. The acid fungal amylase activity can be supplied as an activity in a glucoamylase preparation, or it can be added as a separate enzyme. A suitable acid fungal amylase can be obtained from Novozymes, for example in combination with glucoamylase.

The amount of acid fungal amylase employed in the present process can vary according to the enzymatic activity of the amylase preparation. Suitable amounts include about 0.1 to about 10 acid fungal amylase units (AFAU) per gram of dry solids reduced plant material (e.g., dry solids corn (DSC)). In an embodiment, the reaction mixture can include about 0.3 to about 3 AFAU/gram dry solids reduced plant material (e.g., DSC). In an embodiment, the reaction mixture can include about 1 to about 2 AFAU/gram dry solids reduced plant material (e.g., DSC).

Glucoamylase

In certain embodiments, the present method can employ a glucoamylase. Glucoamylase is also known as amyloglucosidase and has the systematic name 1,4-alpha-D-glucan glucohydrolase (E.C. 3.2.1.3). Glucoamylase refers to an enzyme that removes successive glucose units from the non-reducing ends of starch. For example, certain glucoamylases can hydrolyze both the linear and branched glucosidic linkages of starch, amylose, and amylopectin. A variety of suitable glucoamylases are known and commercially available. For example, suppliers such as Novozymes and Genencor provide glucoamylases. The glucoamylase can be of fungal origin.

The amount of glucoamylase employed in the present process can vary according to the enzymatic activity of the amylase preparation. Suitable amounts include about 0.1 to about 6.0 glucoamylase units (AGU) per gram dry solids reduced plant material (e.g., DSC). In an embodiment, the reaction mixture can include about 1 to about 3 AGU per gram dry solids reduced plant material (e.g., DSC). In an embodiment, the reaction mixture can include about 1 to about 2.5 (e.g., 2.4) AGU per gram dry solids reduced plant material (e.g., DSC). In an embodiment, the reaction mixture can include about 1 to about 2 AGU per gram dry solids reduced plant material (e.g., DSC). In an embodiment, the reaction mixture can include about 1 to about 1.5 AGU per gram dry solids reduced plant material (e.g., DSC). In an embodiment, the reaction mixture can include about 1.2 to about 1.5 AGU per gram dry solids reduced plant material (e.g., DSC).

Fermentation

The present process includes fermenting sugars from reduced plant material to ethanol. Fermenting can be effected by a microorganism, such as yeast. The fermentation mixture need not, and in an embodiment does not, include protease. However, the process waters may contain protease. The amount of protease can be less than that used in the conventional process. According to the present invention, fermenting is conducted on a starch composition that has not been cooked. In an embodiment, the present fermentation process produces potable alcohol. Potable alcohol has only acceptable, nontoxic levels of other alcohols, such as fusel oils. Fermenting can include contacting a mixture including sugars from the reduced plant material with yeast under conditions suitable for growth of the yeast and production of ethanol. In an embodiment, fermenting employs the saccharification mixture.

Any of a variety of yeasts can be employed as the yeast starter in the present process. Suitable yeasts include any of a variety of commercially available yeasts, such as commercial strains of *Saccharomyces cerevisiae*. Suitable strains include "Fali" (Fleischmann's), Thermosac (Alltech), Ethanol Red (LeSafre), BioFerm AFT (North American Bioproducts), and the like. In an embodiment, the yeast is selected to provide rapid growth and fermentation rates in the presence of high temperature and high ethanol levels. In an embodiment, Fali yeast has been found to provide good performance as measured by final alcohol content of greater than 17% by volume.

The amount of yeast starter employed is selected to effectively produce a commercially significant quantity of ethanol in a suitable time, e.g., less than 75 hours.

Yeast can be added to the fermentation by any of a variety of methods known for adding yeast to fermentation processes. For example, yeast starter can be added by as a dry batch, or by conditioning/propagating. In an embodiment, yeast starter is added as a single inoculation. In an embodiment, yeast is added to the fermentation during the fermenter fill at a rate of 5 to 100 pounds of active dry yeast (ADY) per 100,000 gallons of fermentation mash. In an embodiment, the yeast can be acclimated or conditioned by incubating about 5 to 50 pounds of ADY per 10,000 gallon volume of fermenter volume in a prefermenter or propagation tank. Incubation can be from 8 to 16 hours during the propagation stage, which is also aerated to encourage yeast growth. The prefermenter used to inoculate the main fermenter is can be from 1 to 10% by volume capacity of the main fermenter, for example, from 2.5 to 5% by volume capacity relative to the main fermenter.

In an embodiment, the fermentation is conducted at a pH of about 6 or less, pH of about 3 to about 6, about 3.5 to about 6, about 4 to about 5, about 4 to about 4.5, or about 4.5 to about 5. The initial pH of the fermentation mixture can be adjusted by addition of, for example, ammonia, sulfuric acid, phosphoric acid, process waters (e.g., stillage (backset), evaporator condensate (distillate), side stripper bottoms, and the like), and the like.

Although not limiting to the present invention, it is believed that known distillery yeast grow well over the pH range of 3 to 6, but are more tolerant of lower pH's down to 3.0 than most contaminant bacterial strains. Contaminating lactic and acetic acid bacteria grow best at pH of 5.0 and above. Thus, in the pH range of 3.0 to 3.5, it is believed that ethanol fermentation will predominate because yeast will grow better than contaminating bacteria.

In an embodiment, the present method can include varying the pH. It is believed that varying the pH can be conducted to reduce the likelihood of contamination early in fermentation and/or to increase yeast growth and fermentation during the latter stages of fermentation. For example, fermentation can include filling the fermenter at pH of about 3 to about 4.5 during the first half of fill. Fermentation can include increasing the slurry pH to pH of about 4.5 to about 6 during the second half of the fermenter fill cycle. Fermentation can include maintaining pH by adding fresh substrate slurry at the desired pH as described above. In an embodiment, during fermentation (after filling), pH is not adjusted. Rather, in this embodiment, the pH is determined by the pH of the components during filling.

In an embodiment, the pH is decreased to about five (5) or below in the corn process waters. In an embodiment, the pH is about pH 4 (e.g. 4.1) at the start of fermentation fill and is increased to about pH 5 (e.g. 5.2) toward the end of fermentation fill. In an embodiment, the method includes stopping pH control of the mash slurry after the yeast culture becomes established during the initial process of filling the fermenter, and then allowing the pH to drift up in the corn process waters during the end stages of filling the fermenter.

In an embodiment, fermentation is conducted for about to 25 (e.g., 24) to about to 150 hours, about 25 (e.g., 24) to about 96 hours, about 40 to about 96 hours, about 45 (e.g., 44) to about 96 hours, about 48 (e.g., 47) to about 96 hours. For example, fermentation can be conducted for about 30, about 40, about 50, about 60, or about 70 hours. For example, fermentation can be conducted for about 35, about 45, about 55, about 65, or about 75 hours.

In an embodiment, fermentation is conducted at a temperature of about 25 to about 40° C. or about 30 to about 35° C. In an embodiment, during fermentation the temperature is decreased from about 40° C. to about 30° C. or about 25° C., or from about 35° C. to about 30° C., during the first half of the fermentation, and the temperature is held at the lower temperature for the second half of the fermentation. In an embodiment, the temperature can be decreased as ethanol is produced. For example, in an embodiment, during fermentation the temperature can be as high as about 99° F. and then reduced to about 79° F. This temperature reduction can be coordinated with increased ethanol titers (%) in the fermenter.

In an embodiment, the present method includes solids staging. Solids staging includes filling at a disproportionately higher level of solids during the initial phase of the fermenter fill cycle to increase initial fermentation rates. The solids concentration of the mash entering the fermenter can then be decreased as ethanol titers increase and/or as the fermenter fill cycle nears completion. In an embodiment, the solids concentration can be about 40% (e.g. 41%) during the first half of the fermentation fill. This can be decreased to about 25% after the fermenter is 50% full and continuing until the fermenter fill cycle is concluded. In the above example, such a strategy results in a full fermenter with solids at 33%.

It is believed that solids staging can accelerate enzyme hydrolysis rates and encourage a rapid onset to fermentation by using higher initial fill solids. It is believed that lowering solids in the last half of fill can reduce osmotic pressure related stress effects on the yeast. By maintaining overall fermenter fill solids within a specified range of fermentability, solids staging improves the capacity of the yeast to ferment high gravity mashes toward the end of fermentation.

Simultaneous Saccharification and Fermentation

The present process can include simultaneously converting reduced plant material to sugars and fermenting those sugars with a microorganism such as yeast. Simultaneous saccharifying and fermenting can be conducted using the reagents and conditions described above for saccharifying and fermenting.

In an embodiment, saccharification and fermentation is conducted at a temperature of about 25 to about 40° C. or about 30 to about 35° C. In an embodiment, during saccharification and fermentation the temperature is decreased from about 40 to about 25° C. or from about 35 to about 30° C. during the first half of the saccharification, and the temperature is held at the lower temperature for the second half of the saccharification.

Although not limiting to the present invention, it is believed that higher temperatures early during saccharification and fermentation can increase conversion of starch to fermentable sugar when ethanol concentrations are low. This can aid in increasing ethanol yield. At higher ethanol concentrations, this alcohol can adversely affect the yeast. Thus, it is believed that lower temperatures later during saccharification and fermentation are beneficial to decrease stress on the yeast. This can aid in increasing ethanol yield.

Also not limiting to the present invention, it is believed that higher temperatures early during saccharification and fermentation can reduce viscosity during at least a portion of the fermentation. This can aid in temperature control. It is also believed that lower temperatures later during saccharification and fermentation are beneficial to reduce the formation of glucose after the yeast has stopped fermenting. Glucose formation late in fermentation can be detrimental to the color of the distillers dried grain co-product.

In an embodiment, saccharification and fermentation is conducted at a pH of about 6 or less, pH of about 3 to about 6, about 3.5 to about 6, about 4 to about 5, about 4 to about 4.5, or about 4.5 to about 5. The initial pH of the saccharification and fermentation mixture can be adjusted by addition of, for example, ammonia, sulfuric acid, phosphoric acid, process waters (e.g., stillage (backset), evaporator condensate (distillate), side stripper bottoms, and the like), and the like.

In an embodiment, saccharification and fermentation is conducted for about to 25 (e.g., 24) to about to 150 hours, about 25 (e.g., 24) to about 72 hours, about 45 to about 55 hours, about 50 (e.g., 48) to about 96 hours, about 50 to about 75 hours, or about 60 to about 70 hours. For example, saccharification and fermentation can be conducted for about 30, about 40, about 50, about 60, or about 70 hours. For example, saccharification and fermentation can be conducted for about 35, about 45, about 55, about 65, or about 75 hours.

In an embodiment, simultaneous saccharifying and fermenting can be carried out employing quantities of enzyme and yeast selected to maintain high concentrations of yeast and high levels of budding of the yeast in the fermentation broth. For example, the present process can employ quantities of enzyme and yeast selected to maintain yeast at or above about 300 cells/mL or at about 300 to about 600 cells/mL.

In an embodiment, simultaneous saccharifying and fermenting can be carried out employing quantities of enzyme and yeast selected for effective fermentation without added exogenous nitrogen; without added protease; and/or without added backset. Backset can be added, if desired, to consume process water and reduce the amount of wastewater produced by the process. In addition, the present process maintains low viscosity during saccharifying and fermenting.

For example, simultaneous saccharifying and fermenting can employ acid fungal amylase at about 0.1 to about 10 AFAU per gram of dry solids reduced plant material (e.g., DSC) and glucoamylase at about 0.5 to about 6 AGU per gram dry solids reduced plant material (e.g., DSC). For example, simultaneous saccharifying and fermenting can employ acid fungal amylase at about 0.3 to about 3 AFAU per gram of dry solids reduced plant material (e.g., DSC) and glucoamylase at about 1 to about 3 AGU per gram dry solids reduced plant material (e.g., DSC). For example, simultaneous saccharifying and fermenting can employ acid fungal amylase at about 1 to about 2 AFAU per gram of dry solids reduced plant material (e.g., DSC) and glucoamylase at about 1 to about 1.5 AGU per gram dry solids reduced plant material (e.g., DSC).

In an embodiment, simultaneous saccharifying and fermenting can be carried out employing quantities of enzyme and yeast selected to maintain low concentrations of glucose in the fermentation broth. For example, the present process can employ quantities of enzyme and yeast selected to maintain glucose at levels at or below about 2 wt-%, at or below about 1 wt-%, at or below about 0.5 wt-%, or at or below about 0.1 wt-%. For example, the present process can employ quantities of enzyme and yeast selected to maintain glucose at levels at or below about 2 wt-% during saccharifying and fermenting. For example, the present process can employ quantities of enzyme and yeast selected to maintain glucose at levels at or below about 2 wt-% from hours 0-10 (or from 0 to about 15% of the time) of saccharifying and fermenting. For example, the present process can employ quantities of enzyme and yeast selected to maintain glucose at levels at or below about 1 wt-%, at or below about 0.5 wt-%, or at or below about 0.1 wt-% from hours 12-54 (or from about 15% to about 80% of the time) of saccharifying and fermenting. For example, the present process can employ quantities of enzyme and yeast selected to maintain glucose at levels at or below about 1 wt-% from hours 54-66 (or about from 80% to about 100% of the time) of saccharifying and fermenting. Suitable levels of enzyme include acid fungal amylase at about 0.3 to about 3 AFAU per gram of dry solids reduced plant material (e.g., DSC) and glucoamylase at about 1 to about 3 AGU per gram dry solids reduced plant material (e.g., DSC). For example, simultaneous saccharifying and fermenting can employ acid fungal amylase at about 1 to about 2 AFAU per gram of dry solids reduced plant material (e.g., DSC) and glucoamylase at about 1 to about 1.5 AGU per gram dry solids reduced plant material (e.g., DSC).

In an embodiment, simultaneous saccharifying and fermenting can be carried out employing quantities of enzyme and yeast selected to maintain low concentrations of maltose (DP2) in the fermentation broth. For example, the present process can employ quantities of enzyme and yeast selected to maintain maltose at levels at or below about 0.5 wt-% or at or below about 0.2 wt-%. Suitable levels of enzyme include acid fungal amylase at about 0.3 to about 3 AFAU per gram of dry solids reduced plant material (e.g., DSC) and glucoamylase at about 1 to about 3 AGU per gram dry solids reduced plant material (e.g., DSC). For example, simultaneous saccharifying and fermenting can employ acid fungal amylase at about 1 to about 2 AFAU per gram of dry solids reduced plant material (e.g., DSC) and glucoamylase at about 1 to about 1.5 AGU per gram dry solids reduced plant material (e.g., DSC).

In an embodiment, simultaneous saccharifying and fermenting can be carried out employing quantities of enzyme and yeast selected to maintain low concentrations of dextrin in the fermentation broth. For example, the present process can employ quantities of enzyme and yeast selected to maintain maltotriose (DP3) at levels at or below about 0.5 wt-%, at or below about 0.2 wt-%, or at or below about 0.1 wt-%. For example, the present process can employ quantities of enzyme and yeast selected to maintain dextrin with a degree of polymerization of 4 or more (DP4+) at levels at or below about 1 wt-% or at or below about 0.5 wt-%. Suitable levels of enzyme include acid fungal amylase at about 0.3 to about 3 AFAU per gram of dry solids reduced plant material (e.g., DSC) and glucoamylase at about 1 to about 3 AGU per gram dry solids reduced plant material (e.g., DSC). For example, simultaneous saccharifying and fermenting can employ acid fungal amylase at about 1 to about 2 AFAU per gram of dry solids reduced plant material (e.g., DSC) and glucoamylase at about 1 to about 1.5 AGU per gram dry solids reduced plant material (e.g., DSC).

In an embodiment, simultaneous saccharifying and fermenting can be carried out employing quantities of enzyme and yeast selected to maintain low concentrations of fusel oils in the fermentation broth. For example, the present process can employ quantities of enzyme and yeast selected to maintain fusel oils at levels at or below about 0.4 to about 0.5 wt-%. Suitable levels of enzyme include acid fungal amylase at about 0.3 to about 3 AFAU per gram of dry solids reduced plant material (e.g., DSC) and glucoamylase at about 1 to about 3 AGU per gram dry solids reduced plant material (e.g., DSC). For example, simultaneous saccharifying and fermenting can employ acid fungal amylase at about 1 to about 2 AFAU per gram of dry solids reduced plant material (e.g., DSC) and glucoamylase at about 1 to about 1.5 AGU per gram dry solids reduced plant material (e.g., DSC).

Additional Ingredients for Saccharification and/or Fermentation

The saccharification and/or fermentation mixture can include additional ingredients to increase the effectiveness of the process. For example, the mixture can include added nutrients (e.g., yeast micronutrients), antibiotics, salts, added enzymes, and the like. Nutrients can be derived from stillage or backset added to the liquid. Suitable salts can include zinc or magnesium salts, such as zinc sulfate, magnesium sulfate, and the like. Suitable added enzymes include those added to conventional processes, such as protease, phytase, cellulase, hemicellulase, exo- and endo-glucanase, xylanase, and the like.

Recovering Ethanol from the Beer

The product of the fermentation process is referred to herein as "beer". For example, fermenting corn produces "corn beer". Ethanol can be recovered from the fermentation mixture, from the beer, by any of a variety of known processes. For example, ethanol can be recovered by distillation.

The remaining stillage includes both liquid and solid material. The liquid and solid can be separated by, for example, centrifugation. The recovered liquid, thin stillage, can be employed as at least part of the liquid for forming the saccharification and fermentation mixture for subsequent batches or runs.

The recovered solids, distiller's dried grain, include unfermented grain solids and spent yeast solids. Thin stillage can be concentrated to a syrup, which can be added to the distiller's dried grain and the mixture then dried to form distiller's dried grain plus solubles. Distiller's dried grain and/or distiller's dried grain plus solubles can be sold as animal feed.

Burn-out of Residual Starches for Subsequent Fermentation

In an embodiment, the present method can include heat treatment of the beer or stillage, e.g., between the beer well and distillation. This heat treatment can convert starches to dextrins and sugars for subsequent fermentation in a process known as burn-out. Such a treatment step can also reduce fouling of distillation trays and evaporator heat exchange surfaces. In an embodiment, heat treatment staging can be performed on whole stillage. Following enzymatic treatment of the residual starches, in an embodiment, the resulting dextrins and sugars can be fermented within the main fermentation process as recycled backset or processed in a separate fermentation train to produce ethanol.

Fractionation of Solids from Fermentation

Large pieces of germ and fiber can ferment the residual starch in the fermenter. After fermentation, the fractions could be removed prior to or after distillation. Removal can be effected with a surface skimmer before to distillation. In an embodiment, screening can be performed on the beer. The screened material can then be separated from the ethanol/water mix by, for example, centrifugation and rotary steam drum drying, which can remove the residual ethanol from the cake. In embodiments in which the larger fiber and germ pieces are removed prior to bulk beer distillation, a separate stripper column for the fiber/germ stream can be utilized. Alternatively, fiber and germ could be removed by screening the whole stillage after distillation.

In an embodiment, all the components are blended and dried together. The fiber and germ can be removed from the finished product by aspiration and/or size classification. The fiber from the DDGS can be aspirated. Removal of fiber by aspiration after drying increased the amount of oil and protein in the residual DDGS by 0.2 to 1.9% and 0.4 to 1.4%, respectively. The amount of NDF in the residual DDGS decreased by 0.1 to 2.8%.

In an embodiment, fractionation can employ the larger fiber and germ pieces to increase the particle size of that part of the DDGS derived from the endosperm, as well as to improve syrup carrying capacity. A ring dryer disintegrator can provide some particle size reduction and homogenization.

Continuous Fermentation

The present process can be run via a batch or continuous process. A continuous process includes moving (pumping) the saccharifying and/or fermenting mixtures through a series of vessels (e.g., tanks) to provide a sufficient duration for the process. For example, a multiple stage fermentation system can be employed for a continuous process with 48-96 hours residence time. For example, reduced plant material can be fed into the top of a first vessel for saccharifying and fermenting. Partially incubated and fermented mixture can then be drawn out of the bottom of the first vessel and fed in to the top of a second vessel, and so on.

Although not limiting to the present invention, it is believed that the present method is more suitable than conventional methods for running as a continuous process. It is believed that the present process provides reduced opportunity for growth of contaminating organisms in a continuous process. At present, the majority of dry grind ethanol facilities employ batch fermentation technology. This is in part due to the difficulty of preventing losses due to contamination in these conventional processes. For efficient continuous fermentation using traditional liquefaction technology, the conventional belief is that a separate saccharification stage prior to fermentation is necessary to pre-saccharify the mash for fermentation. Such pre-saccharification insures that there is adequate fermentable glucose for the continuous fermentation process.

The present method achieves efficient production of high concentrations of ethanol without a liquefaction or saccharification stage prior to fermentation. This is surprising since this conventional wisdom teaches that it is necessary to have adequate levels of fermentable sugar available during the fermentation process when practiced in a continuous mode. In contrast the present method can provide low concentrations of glucose and efficient fermentation. In the present method, it appears that the glucose is consumed rapidly by the fermenting yeast cell. It is believed that such low glucose levels reduce stress on the yeast, such as stress caused by osmotic inhibition and bacterial contamination pressures. According to the present invention, ethanol levels greater than 18% by volume can be achieved in about 45 to about 96 hours.

High Alcohol Beer

The present invention also relates to a high alcohol beer. In an embodiment, the process of the present invention produces beer containing greater than 18 vol-% ethanol. The present process can produce such a high alcohol beer in about 40 to about 96 hours or about 45 to about 96 hours. In an embodiment, the beer includes 18 vol-% to about 23 vol-% ethanol. For example, the present method can produce alcohol contents in the fermenter of 18 to 23% by volume in about 45 to 96 hours.

By way of further example, the present method can produce alcohol content in the fermenter of 18 to 23% by volume in about 45 to 96 hours. In certain embodiments, the majority of the alcohol (80% or more of the final concentration) is produced in the first 45 hours. Then, an additional 2 to 5 vol-% alcohol can be produced in the final 12-48 hours. Concentrations of ethanol up to 23 vol-% can be achieved with fermentation time up to 96 hours. It can be economically advantageous to harvest after 48 to 72 hours of fermentation to increase fermenter productivity.

The present beer can include this high level of ethanol even when it includes high levels of residual starch. For example, the present beer can include ethanol at 18 to 23 vol-% when it contains 0 to 30% residual starch. The present beer can contain residual starches as low as 0% to as high as 20% residual starch.

By conventional measures, high levels of residual starch indicate inefficient fermentation, which yields only low levels of ethanol. In contrast, although not limiting to the present invention, it is believed that the present method results in fewer Maillard type reaction products and more efficient yeast fermentation (e.g., reduced levels of secondary metabolites). This is believed to be due to the low glucose levels and low temperatures of the present method compared to conventional saccharification and liquefaction. Thus, the present method can produce more alcohol even with higher levels of residual starch.

In an embodiment, the present beer includes fewer residual byproducts than conventional beers, even though residual starch can be higher. For example, residual glucose, maltose, and higher dextrins (DP3+) can be as much as 0.8 wt-% lower than in conventional beers produced under similar fermentation conditions. By way of further example, residual glycerol can be as much as 0.45 wt-% less. Lactic acid and fusel oils can also be significantly reduced. For example, the present beer can include less than or equal to about 0.2 wt-% glucose, about 0.4 wt-%, about 0.1 wt-% DP3, undetectable DP4+, 0.45 wt-% glycerol, about 0.01 wt-% lactic acid, and/or about 0.4 wt-% fusel oils.

High Protein Distiller's Dried Grain

The present invention also relates to a distiller's dried grain product. The distiller's dried grain can also include elevated levels of one or more of protein, fat, fiber (e.g., neutral detergent fiber (NDF)), and starch. For example, the distiller's dried grain can include 34 or more wt-% protein or about 30 to about 45 wt-% protein, or about 1 to about 2 wt-% more protein than produced by the conventional process. For example, the distiller's dried grain can include 15 or more wt-% fat, about 13 to about 17 wt-% fat, or about 1 to about 6 wt-% more fat than produced by the conventional process. For example, the distiller's dried grain can include 31 or more wt-% fiber, about 23 to about 37 wt-% fiber, or about 3 to about 13 wt-% more fiber than produced by the conventional process. For example, the distiller's dried grain can include 12 or more wt-% starch, about 1 to about 23 wt-% starch, or about 1 to about 18 wt-% more starch than produced by the conventional process.

In an embodiment, the present distiller's dried grain includes elevated levels of B vitamins, vitamin C, vitamin E, folic acid, and/or vitamin A, compared to conventional distiller's dried grain products. The present distiller's dried grain has a richer gold color compared to conventional distiller's dried grain products.

Distiller's Dried Grain with Improved Physical Characteristics

The present invention also relates to a distiller's dried grain with one or more improved physical characteristics, such as decreased caking or compaction or increase ability to flow. The present process can produce such an improved distiller's dried grain.

Although not limiting to the present invention, it is believed that the present process can produce fermentation solids including higher molecular weight forms of carbohydrates. Such fermentation solids can, it is believed, exhibit a higher glass transition temperature (i.e. higher $T_g$ values). For example, residual starches have a high $T_g$ value. Thus, through control of starch content in the DDG and DDGS, the present process can manufacture DDG or DDGS with target $T_g$ values.

Further, according to the present invention, adding an alkaline syrup blend (e.g., syrup plus added lime or other alkaline material) to the fermentation solids (e.g., distiller's dried grains) can provide decreased caking or compaction or increase ability to flow to the distiller's dried grain with solubles (DDGS).

Although not limiting to the present invention, it is believed that organic acids such as lactic, acetic, and succinic acids which are produced in fermentation have a lower $T_g$ value than their corresponding calcium salts. Maintenance of residual carbohydrate in higher molecular weight form, or addition of lime to form calcium salts of organic acids, are two strategies for forming higher $T_g$ value co-products that will be less likely to undergo the glass transition, resulting in the deleterious phenomenon known as caking.

Although not limiting to the present invention, it is believed that process of the present invention can need not destroy protein in the fermented plant material. Corn contains prolamins, such as zein. Grain sorghum, for example, contains a class of zein-like proteins known as kafirins, which resemble zein in amino acid composition. The thermal degradation that occurs during liquefaction, distillation, and high temperature drying produces DDG and DDGS including significant amounts of degraded protein. It is believed that the process of the present invention can provides improved levels of the prolamin fraction of cereal grains.

It is believed that extended exposure to high alcohol concentrations that can be achieved by the present process can condition the proteins in the plant material. This can solubilize some of the proteins. For example, it is believed that in distillation the ethanol concentration reaches levels that can solubilize prolamins (e.g., zein) in the beer. Upon the removal, or "stripping," of ethanol from the beer, prolamins (such as zein) can be recovered concentrated in DDG and DDGS. The resulting high protein content of DDG and DDGS an be advantageous for various end used of DDG and DDGS, for example in further processing or compounding.

In an embodiment, efficient fermentation of the present process removes from the DDG or DDGS non zein components such as starch. Fractionating the plant material, e.g., corn, can also increase levels of proteins, such as zein, in the DDG or DDGS. For example, removing the bran and germ fractions prior to fermentation can concentrate zein in the substrate. Zein in corn is isolated in the endosperm. Fermentation of zein enriched endosperm results in concentration of the zein in the residuals from fermentation.

In an embodiment, the process of the present invention can provide DDG and DDGS with different, predetermined $T_g$ values. The process of the present invention can ferment fractions containing high, medium, or low levels of zein, thus varying the glass transition temperature of the resulting DDG or DDGS. The resulting co-product $T_g$ can be directly proportional to the prolamin protein (such as zein) content. The process of the current invention is desirable for the fermentation of high protein corn. This also allows production of DDG and DDGS with a higher prolamin (zein) content.

Residual starch remaining at the end of fermentation preferentially segregates into the thin stillage fraction, which is subsequently evaporated to produce syrup. The wet cake fraction produced by the present method, which can be dried separately to produce DDG, can be higher in prolamin protein (such as zein) than conventional DDG. The present process allows syrup and wet cake blend ratios to be varied. This results in DDG/DDGS with varying ratios of prolamin protein (such as zein) and residual starch. As the residual starch in the wet cake reduces the protein in the wet cake increases. This indicates an inverse relationship. A similar response occurs in the syrup fraction.

It is believed that starch can segregate into the liquid fraction. The amount of starch in the DDGS can be varied by blending syrup at rates ranging from 0 lbs. dry weight of syrup solids to 1.2 lbs. of syrup solids per lb. of wet cake solids before, and various times during drying to create the final DDGS product. The disproportionate segregation of residual starches into the backset or thin stillage fraction can provide both the aforementioned burn-out and secondary fermentation to be performed on these fractions. Since the thin stillage is evaporated to produce syrup, the centrifuge mass balance also enables DDGS production at various $T_g$ values depending on the desired properties and their dependence on $T_g$.

Emissions

The present invention has emissions benefits. Emissions benefits result in the reduction in byproducts created in the ethanol manufacturing process. There is a marked reduction in extraction of fats and oils in the mash from the germ fraction of cereal grains. There is a reduction of byproducts from Maillard reactions typically formed during cooking and liquefaction. And there is a reduction in fermentation byproducts. These observations result in reduced emissions during the recovery of co-products. The concentration and emission rates of volatile organic compounds (VOC), carbon monoxide (CO), nitric oxide compounds (NOx), sulfur oxides (SO2), and other emissions are considerably lower. See Table 1. Note that other manufacturers have attempted to lower emissions by manufacturing wet cake instead of drying to DDG or DDGS.

The present invention also relates to volatile organic compounds (VOC), such as those produced by drying products of a fermentation process. The present method includes producing ethanol, distiller's dried grain, and additional useful fermentation products with production of lower levels of VOC compared to conventional processes. For example, in the present method, drying distillation products (e.g., spent grain) produces reduced levels of VOC.

Conventional fermentation processes using corn, for example, produces about 2.1 pounds of VOC's from drying distillation products from each ton of corn processed. The actual stack emissions can be less due to pollution control equipment. The present method results in at least 30% reduction in VOC production to about 1.47 or less pounds per ton of corn processed. These emissions reductions are unexpected yet highly significant, and provide for more efficient use of emissions reduction control technology, such as thermal oxidizers.

VOC produced by fermentation processes include ethanol, acetic acid, formaldehyde, methanol, acetaldehyde, acrolein, furfural, lactic acid, formic acid, and glycerol.

The present invention also relates to carbon monoxide (CO), such as those produced by drying products of a fermentation process. The present method includes producing ethanol, distiller's dried grain, and additional useful fermentation products with production of lower levels of CO compared to conventional processes. For example, in the present method, drying distillation products (e.g., spent grain) produces reduced levels of CO.

Conventional fermentation processes using corn, for example, produces about 1.4 pounds of CO's from drying distillation products from each ton of corn processed. The actual stack emissions can be less due to pollution control equipment. The present method results in a 30% reduction in CO production to about 0.98 or less pounds per ton of corn processed. These emissions reductions are unexpected yet highly significant, and provide for more efficient use of emissions reduction control technology, such as thermal oxidizers.

TABLE 1

Emissions Reductions

| Emission Type | | Units | Conventional Run | Inventive Process | Emissions Reduction % |
|---|---|---|---|---|---|
| VOC | Concentration | ppmv lb/dscf | 663 | 459.65 | 30.67 |
| | Emission Rate | lb/hr | 13.35 | 7.91 | 40.75 |
| CO | Concentration | ppmv lb/dscf | 434 | 234.13 | 46.05 |
| | Emission Rate | lb/hr | 9.1 | 4.94 | 45.71 |

The present invention may be better understood with reference to the following examples. These examples are intended to be representative of specific embodiments of the invention, and are not intended as limiting the scope of the invention.

EXAMPLES

Example 1

Production of Improved Distiller's Dried Grain from Corn

A method according to the present invention was employed to produce distiller's dried grain from corn. This method produced high protein, high fat, and high fiber distiller's dried grain. Comparison with a conventional saccharification and liquefaction process indicates superior performance of the present method.

Materials and Methods

Raw Starch Fermentation

Yeast inoculum was prepared by adding glucoamylase (0.088 ml of Novozyme's Spirizyme Plus gluco-amylase at 400 AGU/g) and protease (0.018 ml of Genencor International's GC 106 protease 1000 SAPU/g) to 400 ml of stillage containing 70 grams of maltodextrin. Stillage (backset) used was prepared from prior conventional or raw starch fermentations by distilling off the alcohol and subjecting the resulting whole stillage to centrifugal separation to produce backset. 1.07 grams of urea, 0.13 grams of zinc sulfate, and 0.00067 ml of a 1:1000 dilution of Antibiotic (Alltech Lactocide. [amount?]mg) were also added. About 300-400 million cells/ml of viable cells of yeast (*Saccharomyces cervisiae*) (0.48 g of Fleischmann's Fali yeast) was added to this mixture and propagation was conducted without stirring, or agitating, for 8 hours at an incubation temperature of 90° F. Flasks were periodically swirled under gentle conditions to effect mixing of the contents. The resulting yeast culture (10.8 ml) was added directly to each fermenter for inoculation.

Corn was obtained from commercial suppliers of seed corn and was ground through a 0.5 mm screen using a hammermill prior to fermentation. Several varieties of conventional number 2 yellow dent corn were compared, and in several experiments their isogenically equivalent of waxy corn was also tested. Different corn varieties were tested to demonstrate that the present methods produce improved DDG using any of a variety of corn hybrids.

Approximately 129 to 134 grams of the appropriate corn was mixed in about 225 ml of water. Actual grams of flour (ground corn) and water volumes were adjusted for each fermenter based on the moisture content of the flour so that all fermentations were run at approximately 33.4 grams of dry solids corn per 100 grams of water (33.4% DSC). All raw starch fermenters were adjusted to pH 5.0 with sulfuric acid.

Fermentations were conducted at 82° F. Antibiotic (Alltech Lactocide. 3 mg) was added to each fermentation batch. The raw starch fermentations employed a commercially available glucoamylase preparation (Novozymes' Spirizyme Plus 0.317 ml of GAU/ml) which also includes acid fungal amylase activity.

Fermentations were conducted for 72 hours with sampling conducted at approximately 24 (e.g. 25) hour intervals. All samples were analyzed by HPLC. At the end of fermentation beer samples were placed in metal pans, pH was decreased to <3.5 to inactivate residual enzyme activity, and dried.

Conventional Fermentation

Preparation of yeast inoculum and grinding of corn to corn flour was accomplished as described above for the raw starch fermentation.

For fermentations employing the conventional process, pH adjustment was not necessary; the natural pH of the water and corn flour was 5.8 to 6.0. The conventional fermentations started with a saccharification or cooking stage to liquefy the starch in the mixture. The cook stage was conducted for 60 minutes at a temperature of 85° C. 0.044 ml of Novozymes Liquozyme SC Alpha-amylase (0.044 ml of Novozymes Liquozyme SC 120 AFAU (KNU)/ml) was added to liquefy the corn mash.

Conventional fermentations were also run at 82° F. and included Antibiotic (3 mg of Alltech Lactocide antibiotic). Protease (0.0047 ml of GC 106 protease (1000 SAPU/g/ml) and 0.64 ml of 50% urea liquor (50% of industrial grade urea) were added to fermenters using the conventional process. A commercially available glucoamylase (0.095 ml of Genencor International's GC 480 glucoamylase at 400 AGU/ml) was added for fermentation. Otherwise, fermentations were generally conducted as described above for raw starch fermentations.

Results and Discussion

Fermentation Results are shown in Table 1 and summarized in Table 2.

TABLE 1

Comparison of Process Impacts on Proximate Analysis of DDGS

| Corn Hybrid | Residual Sugars as Glucose (%) | | % Acids Lactic & Acetic | |
|---|---|---|---|---|
| | Conv | RSH | Conv | RSH |
| #2 Yellow Hybrid A | 2.57 | 0.58 | 0.09 | 0.06 |
| #2 Yellow Hybrid B | 1.67 | 0.84 | 0.09 | 0.06 |
| Waxy Isogenic Pair to Hybrid B | 1.70 | 2.11 | 0.10 | 0.06 |
| #2 Yellow Hybrid C | 1.18 | 0.62 | 0.08 | 0.06 |
| Waxy Isogenic Pair to Hybrid C | 1.43 | 1.49 | 0.10 | 0.07 |
| #2 Yellow Hybrid D | 0.84 | 0.49 | 0.06 | 0.05 |
| Waxy Isogenic Pair to Hybrid D | 0.58 | 0.89 | 0.06 | 0.07 |
| Waxy Hybrid E | 1.15 | 0.50 | 0.10 | 0.06 |
| #2 Yellow Hybrid F | 1.86 | 0.61 | 0.11 | 0.07 |
| Waxy Hybrid G | 1.23 | 0.97 | 0.12 | 0.09 |
| Hetero Waxy Isogenic Pair to Hybrid G | 1.14 | 0.39 | 0.10 | 0.07 |
| Averages | 1.40 | 0.86 | 0.09 | 0.07 |

| | % Glycerol | | % Starch | | % Protein | | % Fat | | % NDF | |
|---|---|---|---|---|---|---|---|---|---|---|
| Corn Hybrid | Conv | RSH | Conv | RSH | Conv | RSH | Conv | RSH | Conv | RSH |
| #2 Yellow Hybrid A | 1.09 | 0.86 | 6.86 | 22.24 | 31.25 | 32.15 | 11.05 | 13.65 | 20.45 | 29.00 |
| #2 Yellow Hybrid B | 1.12 | 0.77 | 2.78 | 21.14 | 31.90 | 33.20 | 13.30 | 17.00 | 24.90 | 32.30 |
| Waxy Isogenic Pair to Hybrid B | 1.11 | 0.75 | 1.97 | 14.35 | 31.10 | 30.40 | 14.30 | 16.40 | 25.30 | 34.10 |
| #2 Yellow Hybrid C | 1.20 | 0.85 | 1.68 | 17.51 | 31.50 | 33.80 | 15.00 | 21.30 | 22.00 | 31.00 |
| Waxy Isogenic Pair to Hybrid C | 1.13 | 0.82 | 1.79 | 9.92 | 30.00 | 29.70 | 15.20 | 17.10 | 24.60 | 37.40 |
| #2 Yellow Hybrid D | 1.03 | 0.74 | 0.83 | 14.61 | 36.40 | 37.60 | 11.90 | 14.80 | 23.40 | 28.90 |
| Waxy Isogenic Pair to Hybrid D | 1.06 | 0.78 | 1.11 | 3.39 | 33.30 | 34.20 | 12.80 | 15.70 | 24.60 | 31.70 |
| Waxy Hybrid E | 1.11 | 0.76 | 0.65 | 1.90 | 35.60 | 35.90 | 11.60 | 13.30 | 26.90 | 29.90 |

TABLE 1-continued

Comparison of Process Impacts on Proximate Analysis of DDGS

| | | | | | | | | | | |
|---|---|---|---|---|---|---|---|---|---|---|
| #2 Yellow Hybrid F | 1.17 | 0.78 | 3.27 | 15.99 | 31.80 | 31.10 | 12.50 | 13.30 | 28.10 | 33.10 |
| Waxy Hybrid G | 1.11 | 0.84 | 10.49 | 1.04 | 39.70 | 41.10 | 12.10 | 14.00 | 20.30 | 23.70 |
| Hetero Waxy Isogenic Pair to Hybrid G | 1.05 | 0.84 | 12.15 | 13.74 | 36.60 | 38.90 | 8.96 | 10.90 | 20.80 | 26.50 |
| Averages | 1.11 | 0.80 | 3.96 | 12.35 | 33.56 | 34.37 | 12.61 | 15.22 | 23.76 | 30.69 |

TABLE 2

Comparison of Process Impacts on Proximate Analysis of DDGS (Summary)

| | Process | |
|---|---|---|
| Proximate Analysis | Conventional | Raw Starch |
| Starch | 3.96 | 12.35 |
| Protein | 33.56 | 34.37 |
| Fat | 12.61 | 15.22 |
| Fiber | 23.76 | 30.69 |
| Ash | 4.06 | 4.29 |
| Unknown | 22.05 | 3.08 |
| Summation | 100.00 | 100.00 |

An interesting feature of the raw starch process is that it results in distiller's dried grain with solubles (DDGS) with equal or higher levels of several components, even when it appears that fermentation efficiency, as measured by residual starch, was decreased for the raw starch process. One would expect that, with the lower efficiency, the other components of the DDGS would be lower based on mass balance. The raw starch process apparently results in less damage to the constituents of the grain.

Another interesting feature of the raw starch process is the performance improvement realized using waxy corn hybrids. Waxy corn is almost entirely comprised of amylopectin starch, whereas normal #2 yellow corn is about 25 to 28% amylose starch with the remainder being amylopectin. Waxy corn is generally not used in the conventional process because of the high peak viscosity and more rapid rate of viscosity development compared to regular corn. The high initial viscosity makes the corn slurry more difficult to pump during the initial primary high temperature liquefaction. Waxy corn varieties can, however, be readily employed in the present process. Because no cook stage is employed, the high peak viscosity is not a processing issue.

Example 2

The Present Process Provides Improved Yield Potential

The yield potential of the method of the present invention was compared to a conventional process. The present method exhibited improved yield using temperature staging. The present method exhibited an increased potential maximum yield for ethanol production. Comparison with conventional saccharification and liquefaction process indicates superior performance of the present method.

Materials and Methods

Fermentations were prepared in a similar manner as in Example 1 except for intentional differences in particle size, alpha amylase enzyme dose, gluco-amylase enzyme dose, or acid fungal amylase enzyme dose. Conditions for this experiment are described in Table 3. Corn for all tests was obtained from Broin Enterprises (BEI), Scotland, S. Dak., USA. Corn representing a coarse particle size by raw starch standards was ground at BEI. Finely ground corn was produced using a lab hammermill through a 0.5 mm screen.

The conventional process utilized indicated levels of Liquozyme SC and GC 480. The raw starch process used indicated levels of Spirizyme Plus and SP 288 acid fungal amylase at 1700 AFAU's per gm. Dosages of urea liquor, zinc sulfate, and antibiotic were adjusted accordingly for the conventional process. Stillage (backset) used was prepared from prior conventional or raw starch fermentations by distilling off the alcohol and subjecting the resulting whole stillage to centrifugal separation to produce backset. Fermentation temperatures were staged according to the following set points: 0-18 hours at 90° F., 18-42 hours at 86° F., and 42-72 hours at 82° F. Samples were taken at 65 hours to represent the end of fermentation.

Results and Discussion

The objective of these experiments was to illustrate the sensitivities of the two processes to changes in enzyme dose rate and compare differences in ethanol % and residual starch. The results are shown in Table 3 and FIGS. 1A, 1B, 1C, 1D and 1E. The impact of grind size and enzyme dose on the two processes is apparent. Note that SP 288 acid fungal amylase is effective at accessing raw starch. Acid fungal amylase appears to improve the ability to access starch such that grind size has less effect on yield when SP 288 is present. The present process achieved significantly better alcohol yields at equivalent or higher residual starch levels. FIG. 1B illustrates a similar effect of grind size on ethanol yield in the conventional process, and demonstrates the importance of GA dosage level on accessing starch in coarse grain particles.

Figure 1B:
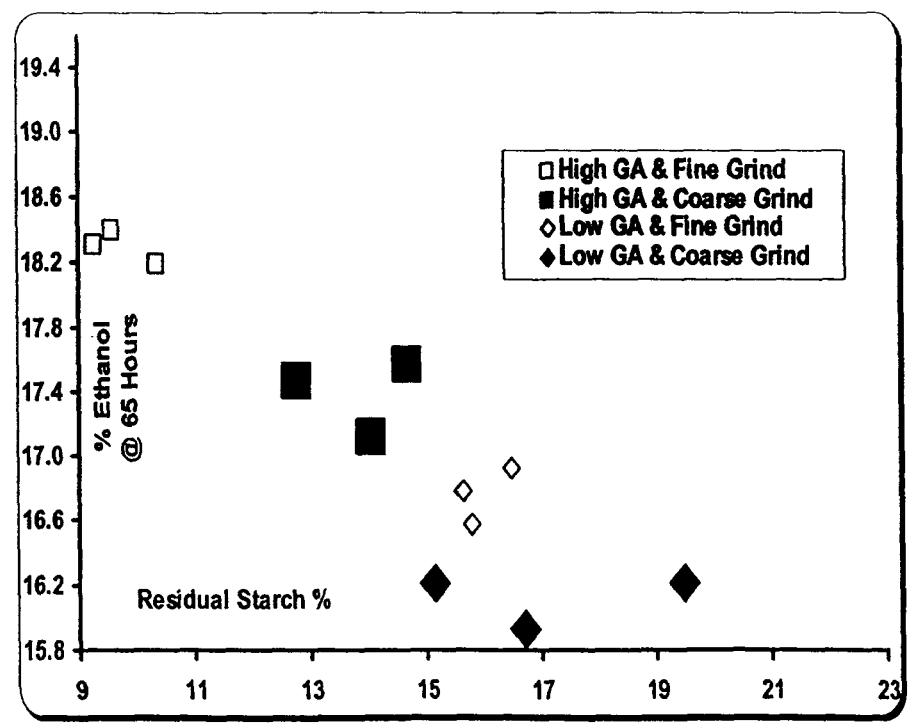
Figure 1C:
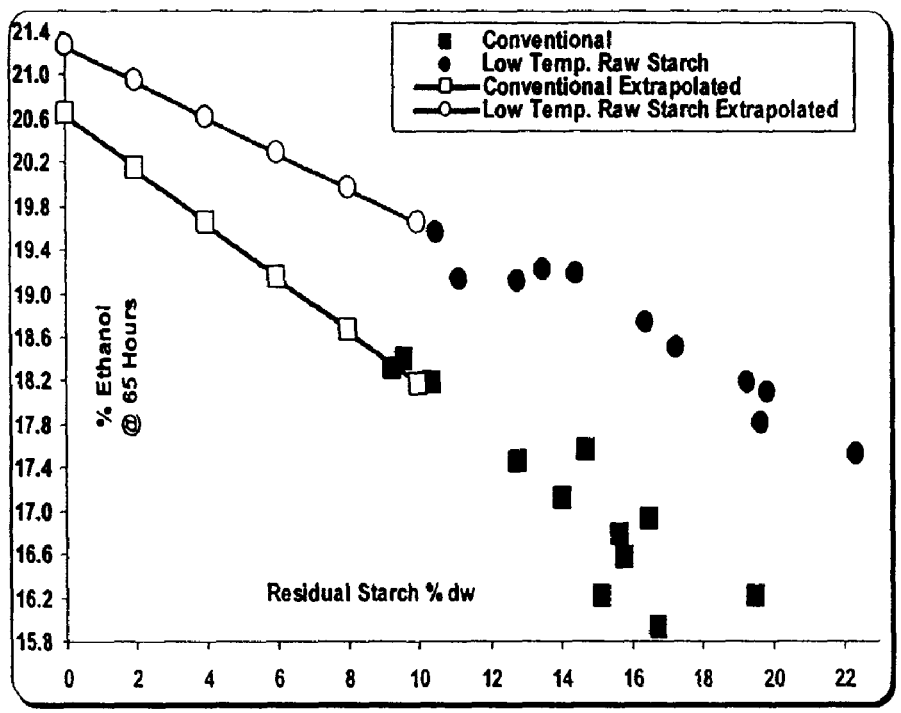
Figure 1D:
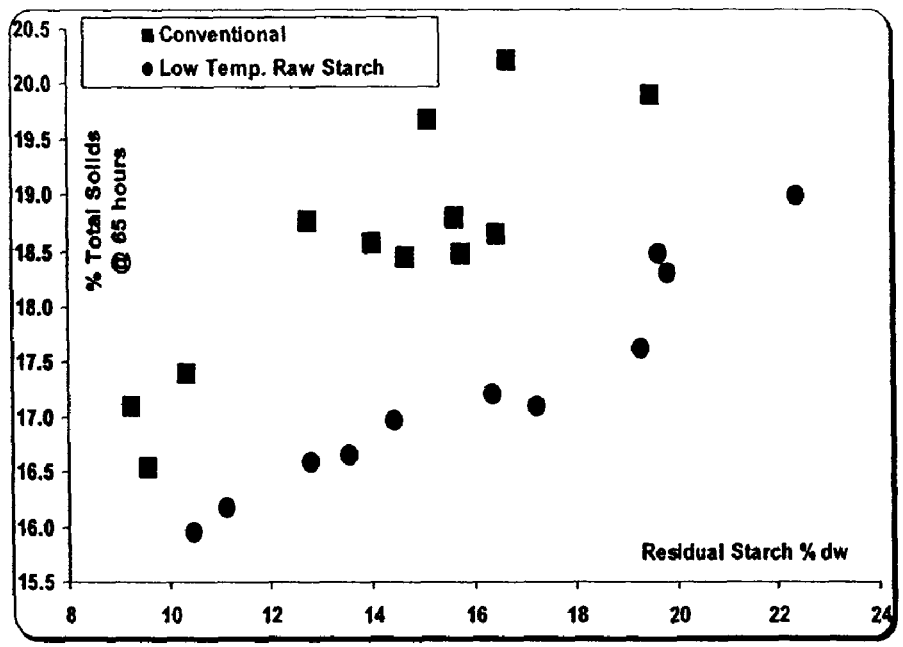

Extrapolation of the results for both the conventional and raw starch process shown in FIGS. 1A and 1B to zero residual starch reveals an embodiment of the raw starch process. As residual starch levels decrease based on improving conversion efficiencies, this process can achieve higher ethanol % than the conventional process. For example, in the absence of residual starch, the present process in this example would produce 21.3 vol-% ethanol, but the conventional process would produce only 20.6 vol-% ethanol. Such an increase is significant. The present process potential of the new process compared to the existing process is shown in FIGS. 1C and 1D. These figures summarize the results for both processes run under the varying grind size and enzyme dosage combinations. FIG. 1C illustrates the potential for the new process to produce more alcohol than the conventional process, even when residual starch levels are higher. Conventional wisdom would suggest the raw starch process is less efficient due to the higher levels of residual starch, however, this is not the case. The present process is superior to the conventional method. Note that fermentation efficiency can also be assessed by examining the fermentation drop solids. This is shown in the composite data comparing both processes in FIG. 1D. Since all fermentations in the above example were started at the same initial set solids, a lower drop solids suggests a more efficient conversion of starch to ethanol. The potential of this process is also indicated by the achievement of an equal to or reduced level of drop solids, despite the higher residual starches observed.

Figure 1E:
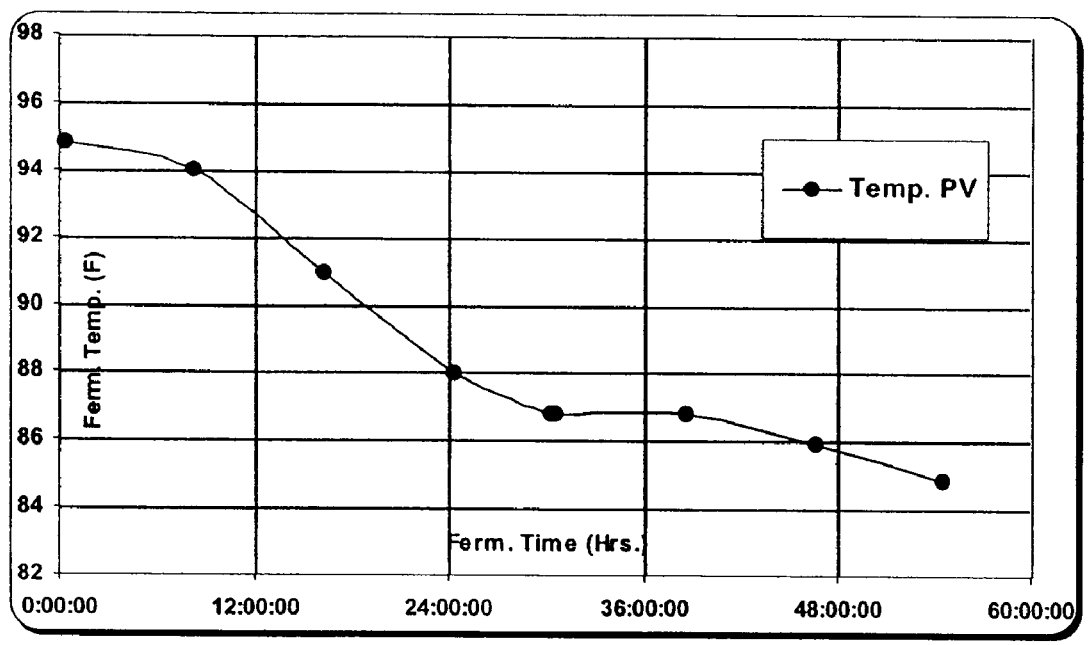

FIG. 1E shows the temperature staging done during the present process. Fermentation temperatures were staged according to the following set points: 0-18 hours at approximately 90° F. (ranging from about 95° F. to about 90° F.), 18-42 hours at approximately 86° F. (ranging from 90° F. to 86° F.), and 42-72 hours at about 82° F. (ranging from 86° F. to 84° F.). Staging of temperature helps to increase ethanol production process by reducing stress on yeast. The temperature is decreased as ethanol is produced to reduce the stress on yeast caused by ethanol production.

Example 3

The Present Process Exhibits Improved Results with increased Levels of Acid Fungal Amylase and Increased Levels of Glucoamylase Results of an embodiment of the method of the present invention were evaluated with increased levels of acid fungal amylase and increased levels of glucoamylase. Increased levels of acid fungal amylase improved results with the present process. The increased levels of glucoamylase improved results with the present process.

Materials and Methods

Glucoamylase (Novozymes Spirizyme Plus) and acid fungal amylase (Novozymes SP 288) were both tested in raw starch fermentations in a manner similar to Example 2, using the coarser grind.

Results and Discussion

The objective of this test was to examine the effect of a range of dosages of glucoamylase and acid fungal amylase on

TABLE 3

Comparison of the Yield Potential of Conventional vs. Raw Starch Processes

Conventional Fermentation Process

| Grind Used | Enzyme Dosages | | Process Water Amounts | | Corn Flour Wt. % | Slurry Dry Solids | AA Dose | Ethanol Vol % | Residual Starch Dry Wt. % |
|---|---|---|---|---|---|---|---|---|---|
| | AA (ml) | GA (ml) | Water (ml) | Backset % | | | | | |
| BEI | 0.04 | 0.08 | 285 | 40 | 190 | 35.91 | Low | 16.21 | 19.49 |
| BEI | 0.04 | 0.12 | 285 | 40 | 190 | 35.89 | Low | 17.57 | 14.69 |
| BEI | 0.06 | 0.08 | 285 | 40 | 190 | 35.90 | Medium | 16.22 | 15.14 |
| BEI | 0.06 | 0.12 | 285 | 40 | 190 | 35.89 | Medium | 17.12 | 14.03 |
| BEI | 0.08 | 0.08 | 285 | 40 | 190 | 35.89 | High | 15.93 | 16.72 |
| BEI | 0.08 | 0.12 | 285 | 40 | 190 | 35.88 | High | 17.47 | 12.78 |
| 0.5 mm | 0.04 | 0.08 | 295 | 40 | 176 | 35.85 | Low | 16.78 | 15.64 |
| 0.5 mm | 0.04 | 0.12 | 295 | 40 | 176 | 35.83 | Low | 18.40 | 9.58 |
| 0.5 mm | 0.06 | 0.08 | 295 | 40 | 176 | 35.84 | Medium | 16.57 | 15.77 |
| 0.5 mm | 0.06 | 0.12 | 295 | 40 | 176 | 35.83 | Medium | 18.19 | 10.36 |
| 0.5 mm | 0.08 | 0.08 | 295 | 40 | 176 | 35.83 | High | 16.92 | 16.48 |
| 0.5 mm | 0.08 | 0.12 | 295 | 40 | 176 | 35.82 | High | 18.31 | 9.27 |

Raw Starch Fermentation Process

| Grind Used | Enzyme Dosages | | Process Water Amounts | | Corn Flour Wt. % | Slurry Dry Solids | GA Dose | Ethanol Vol % | Residual Starch Dry Wt. % |
|---|---|---|---|---|---|---|---|---|---|
| | AA (ml) | GA (ml) | Water (ml) | Backset % | | | | | |
| BEI | 0.00 | 0.34 | 285 | 40 | 190 | 36.35 | Low | 17.53 | 22.37 |
| BEI | 0.03 | 0.34 | 285 | 40 | 190 | 36.35 | Low | 19.19 | 14.45 |
| BEI | 0.00 | 0.42 | 285 | 40 | 190 | 36.32 | Medium | 17.82 | 19.65 |
| BEI | 0.03 | 0.42 | 285 | 40 | 190 | 36.32 | Medium | 19.14 | 11.15 |
| BEI | 0.00 | 0.53 | 285 | 40 | 190 | 36.28 | High | 18.11 | 19.83 |
| BEI | 0.03 | 0.53 | 285 | 40 | 190 | 36.28 | High | 19.13 | 12.80 |
| 0.5 mm | 0.00 | 0.34 | 295 | 40 | 176 | 36.31 | Low | 18.20 | 19.30 |
| 0.5 mm | 0.03 | 0.34 | 295 | 40 | 176 | 36.31 | Low | 19.22 | 13.54 |
| 0.5 mm | 0.00 | 0.42 | 295 | 40 | 176 | 36.28 | Medium | 18.51 | 17.24 |
| 0.5 mm | 0.03 | 0.42 | 295 | 40 | 176 | 36.28 | Medium | 19.56 | 10.50 |
| 0.5 mm | 0.00 | 0.53 | 295 | 40 | 176 | 36.24 | High | 18.75 | 16.38 |

| Screen Size (mm) | No. 12 1.70 mm | No. 16 1.18 mm | No. 20 0.85 mm | No. 25 0.71 mm | No. 30 0.60 mm | No. 35 0.50 mm | Pan <0.50 mm | Sieve Size Pore Size (mm) |
|---|---|---|---|---|---|---|---|---|
| BEI Grind | 0.02 | 0.26 | 2.53 | 7.91 | 12.14 | 20.80 | 54.96 | Percentage on Pan |
| 0.5 mm | 0.00 | 0.00 | 0.00 | 0.00 | 0.00 | 0.00 | 100.00 | |

| Process | AA | GA |
|---|---|---|
| Conventional | Liquozyme SC | GC 480 |
| Raw Starch | SP 288 | Spirizyme Plus | production of ethanol and other products from raw starch hydrolysis fermentations. In particular, dosages above 0.3 AFAU's per gm dry solids corn for acid fungal amylase and dosages above 0.3 AGU's per gram of dry solids corn produce higher alcohol and consistently higher residual glucose. The consistently higher glucose indicates that these fermentations have the potential for even higher ethanol yield.

Figure 2A:
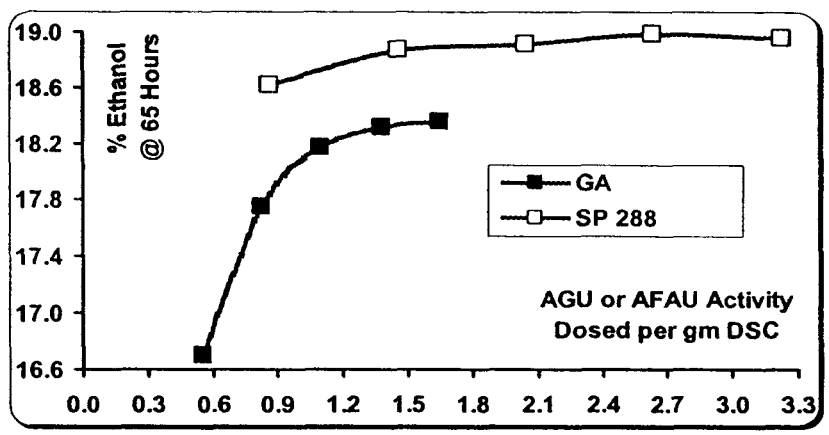
FIGS. 2A-2C illustrate the effect of dosages of glucoamylase and acid fungal amylase in the present process.
Figure 2B:
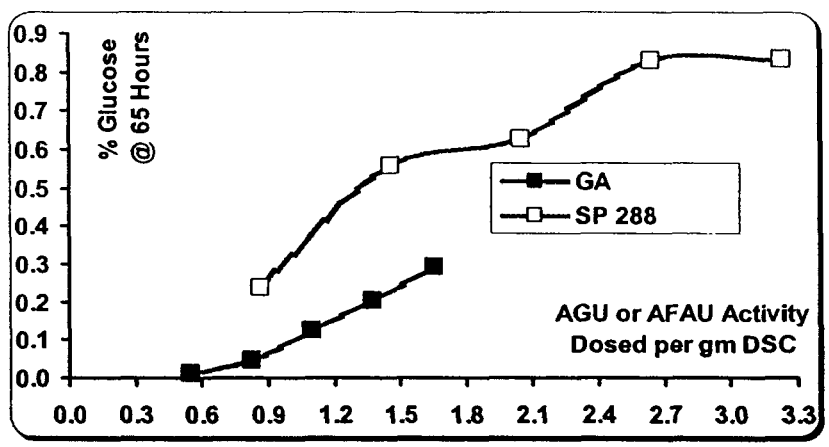
Figure 2C:
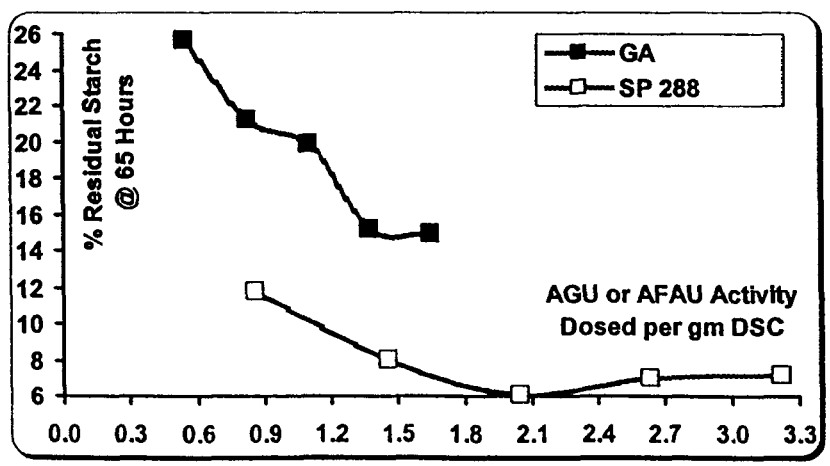
Figure 3A:
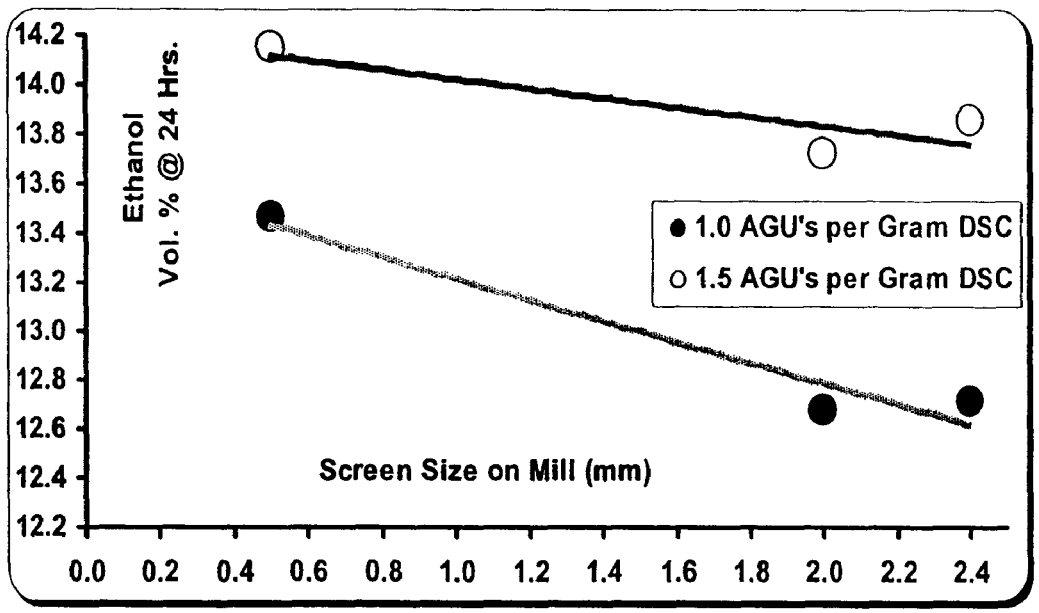
FIGS. 3A-3D illustrate the effect of grind size and enzyme dosage on fermentation efficiency in the present process.
Figure 3B:
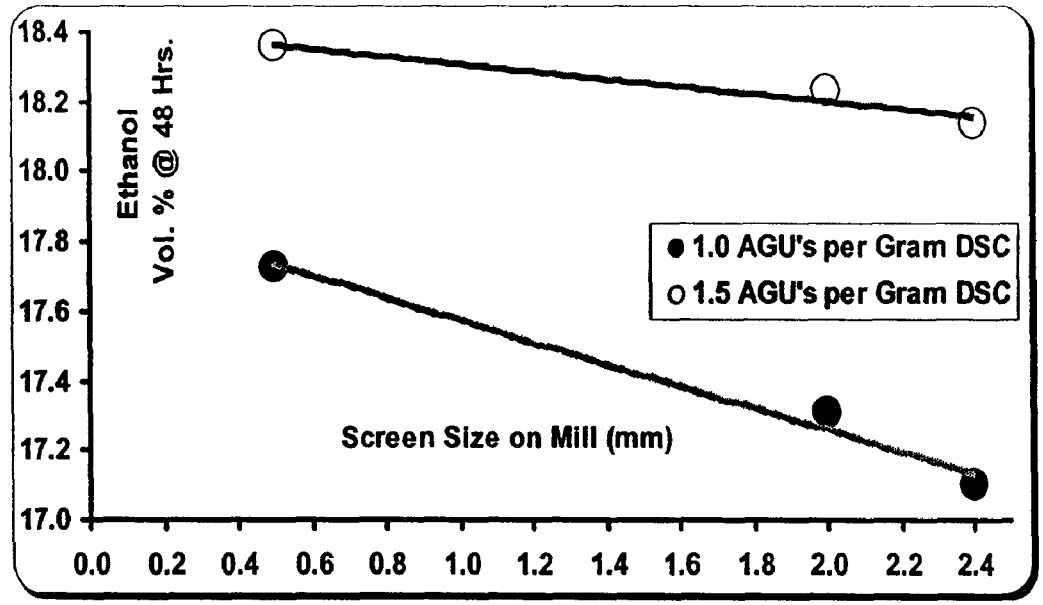
Figure 3C:
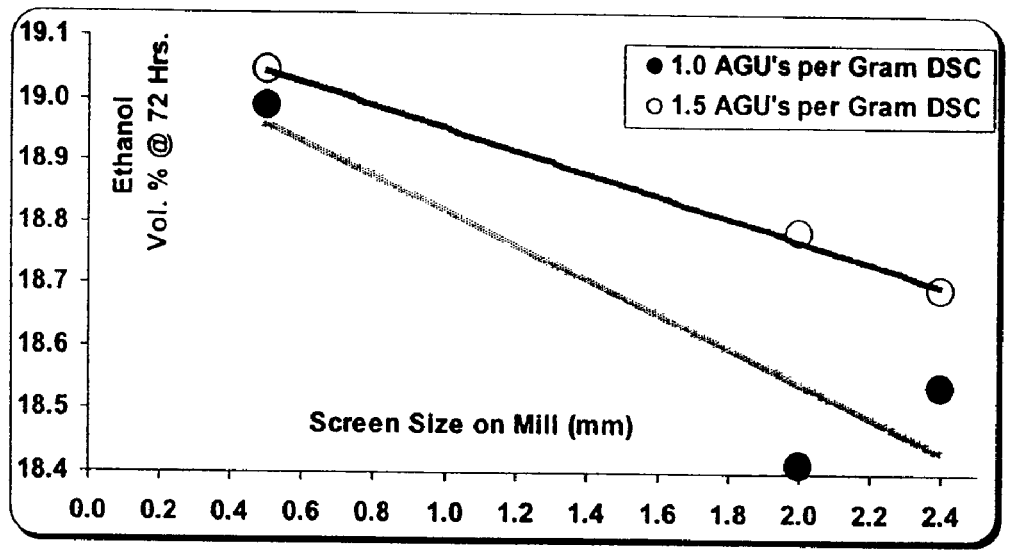
Figure 3D:
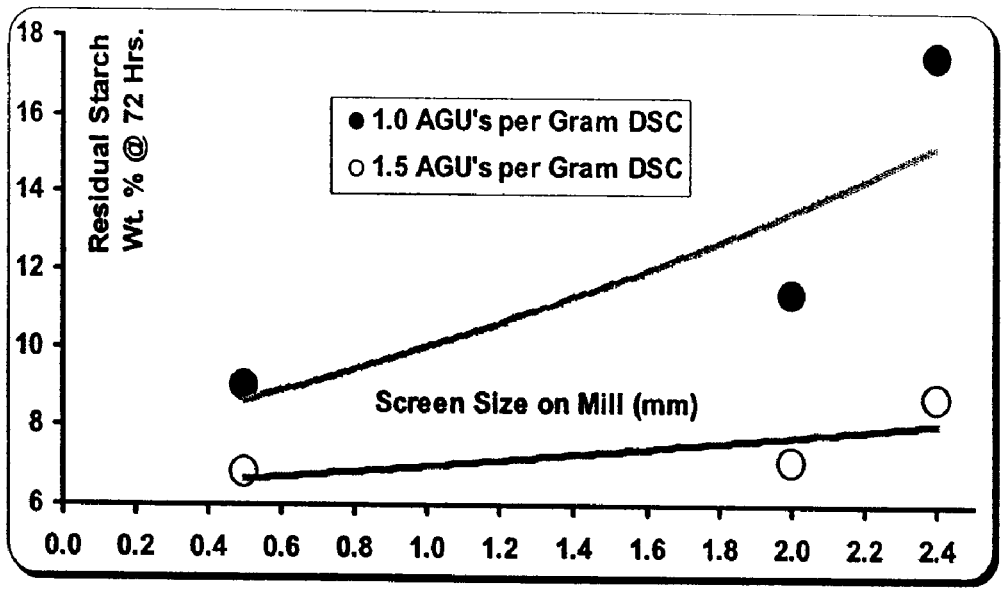

These results suggest that glucoamylase and acid fungal amylase acted synergistically to access raw starch and convert the starch to fermentable sugar. See FIGS. 2A, 2B, and 2C.

Example 4

Impact of Grinding or Reducing Grain Particle Size on Fermentation Efficiency

Results of an embodiment of the method of the present invention were evaluated with varying particle size of the ground plant material. Smaller particle sizes improved results with the present process.

Materials and Methods

A series of lab scale hammermill grinds were performed to generate flour ranging from coarse to relatively fine particle sizes. Raw starch fermentations were set up in a similar manner as in Example 2. Corn Flour used as substrate was ground through a lab hammermill to pass through screens of 0.5 mm, 2.0 mm, and 2.4 mm openings. The conditions tested are shown in Table 4.

Results and Discussion

Results are shown in Table 4, and FIGS. 3A, 3B, 3C, 3D. The data illustrates that smaller grind size provided higher ethanol yield and lower residual starch. At lower glucoamylase doses, grind size was a more influential factor. As the particle size of the grind increased, a higher enzyme dosage was required to achieve the same relative results.

Example 5

Impact of Grind Particle Size, Glucoamylase Type, and Acid Fungal Amylase Dosage on Fermentation Efficiency Results of an embodiment of the method of the present invention were evaluated with varying particle size of the ground plant material, varying glucoamylase type, and dosage of acid fungal amylase.

Materials and Methods

Whole Corn and corn flour was obtained from Dakota Ethanol LLC in Wentworth, S.D. The whole corn was ground through a 2.0 mm screen as in prior examples using a lab scale hammermill. Fermentations were set up in a similar manner as prior Examples according to the outline in Table 5.

TABLE 4

Impact of Grind Particle Size and Glucoamylase Dosage on Fermentation Efficiency

| | Sieve Results | | | | | | | Particle | |
|---|---|---|---|---|---|---|---|---|---|
| Grind Size (mm) | No. 12 1.70 | No. 16 1.18 | No. 20 0.85 | No. 25 0.71 | No. 30 0.60 | No. 35 0.50 | Pan <0.50 | Size (mm) Wt. Avg. | Std Screen Size Mesh Opening (mm) |
| Lab 0.5 | 0.0 | 0.0 | 0.0 | 0.0 | 0.0 | 0.0 | 100.0 | | |
| Lab 2.0 | 0.0 | 0.0 | 1.0 | 3.6 | 2.0 | 9.0 | 85.0 | | |
| Lab 2.4 | 0.1 | 0.4 | 2.1 | 5.7 | 2.4 | 15.0 | 72.8 | | |

| Hammermill Grind Size (mm) | Enzyme Dosage AGU's per Gram DSC | Ethanol Vol. % | Residual Carbohydrates Wt. % | | | | | Byproducts Wt. % | | | Total % Solids | Residual Starch % dw |
|---|---|---|---|---|---|---|---|---|---|---|---|---|
| | | | DP4+ | DP3 | Malt | Gluc | Fruc | Glyc | Lactic | Acetic | | |
| | | | 24 Hour Fermentation Results by HPLC | | | | | | | | | |
| 0.5 | 1.0 | 13.47 | 0.37 | 0.02 | ND | 0.03 | 0.15 | 0.92 | 0.05 | ND | 19.6 | |
| 2.0 | 1.0 | 12.68 | 0.36 | 0.02 | ND | 0.03 | 0.08 | 0.94 | 0.05 | ND | 18.9 | |
| 2.4 | 1.0 | 12.71 | 0.37 | 0.02 | ND | 0.03 | 0.14 | 0.95 | 0.05 | ND | 18.9 | |
| 0.5 | 1.5 | 14.15 | 0.39 | 0.02 | ND | 0.04 | 0.08 | 0.91 | 0.05 | ND | 17.9 | |
| 2.0 | 1.5 | 13.72 | 0.37 | 0.02 | ND | 0.04 | 0.08 | 0.93 | 0.05 | ND | 17.8 | |
| 2.4 | 1.5 | 13.86 | 0.38 | 0.02 | 0.01 | 0.05 | 0.08 | 0.94 | 0.05 | ND | 17.3 | |
| | | | 48 Hour Fermentation Results by HPLC | | | | | | | | | |
| 0.5 | 1.0 | 17.73 | 0.38 | 0.02 | 0.02 | 0.02 | 0.10 | 1.05 | 0.06 | ND | 14.3 | |
| 2.0 | 1.0 | 17.31 | 0.38 | 0.02 | 0.02 | 0.02 | 0.10 | 1.09 | 0.06 | ND | 14.5 | |
| 2.4 | 1.0 | 17.10 | 0.38 | 0.02 | 0.02 | 0.02 | 0.10 | 1.08 | 0.06 | ND | 15.0 | |
| 0.5 | 1.5 | 18.36 | 0.42 | 0.03 | 0.02 | 0.03 | 0.09 | 1.05 | 0.05 | ND | 13.0 | |
| 2.0 | 1.5 | 18.23 | 0.40 | 0.02 | 0.02 | 0.02 | 0.08 | 1.09 | 0.06 | ND | 13.6 | |
| 2.4 | 1.5 | 18.14 | 0.41 | 0.02 | 0.02 | 0.02 | 0.09 | 1.07 | 0.06 | ND | 13.6 | |
| | | | 72 Hour Fermentation Results by HPLC | | | | | | | | | |
| 0.5 | 1.0 | 18.99 | 0.40 | 0.02 | 0.02 | 0.05 | 0.10 | 1.10 | 0.06 | ND | 12.5 | 8.99 |
| 2.0 | 1.0 | 18.42 | 0.38 | 0.02 | 0.01 | 0.05 | 0.10 | 1.13 | 0.06 | ND | 12.8 | 11.34 |
| 2.4 | 1.0 | 18.54 | 0.39 | 0.02 | 0.02 | 0.05 | 0.10 | 1.14 | 0.06 | ND | 12.7 | 17.48 |
| 0.5 | 1.5 | 19.05 | 0.42 | 0.03 | 0.02 | 0.05 | 0.09 | 1.08 | 0.05 | ND | 11.8 | 6.81 |
| 2.0 | 1.5 | 18.78 | 0.40 | 0.02 | 0.02 | 0.05 | 0.09 | 1.11 | 0.06 | ND | 12.0 | 7.07 |
| 2.4 | 1.5 | 18.69 | 0.40 | 0.02 | 0.02 | 0.05 | 0.09 | 1.09 | 0.06 | ND | 12.2 | 8.72 |

TABLE 5

Impact of Grind Particle Size, Glucoamylase Type, and Acid Fungal Amylase Dosage on Fermentation Efficiency

| Screen Size (mm) | No. 12<br>1.70 | No. 16<br>1.18 | No. 20<br>0.85 | No. 25<br>0.71 | No. 30<br>0.60 | No. 35<br>0.50 | Pan<br><0.50 | Sieve Size<br>Pore Size (mm) |
|---|---|---|---|---|---|---|---|---|
| 2.0 mm | 0.0 | 0.2 | 1.4 | 3.2 | 3.6 | 15.3 | 73.0 | "Finer Grind" |
| Plant Hammermill #7 | 10.2 | 18.9 | 14.0 | 7.4 | 3.8 | 7.9 | 38.1 | "Coarser Grind" |

Experimental Outline for Example 5

| AFAU Dose Per Gram DSC | | | AGU Activity per gram DSC | | | | | |
|---|---|---|---|---|---|---|---|---|
| From SP 288<br>SP 288<br>Units/gm DSC | From GA<br>GA<br>Units/gm DSC | Total AFAU<br>Total AFAU<br>Units/gm DSC | From SP 288<br>SP 288<br>Units/gm DSC | From GA<br>GA<br>Units/gm DSC | Total AGU's<br>Total AGU's<br>Units/gm DSC | Flour<br>Grind | L-400 GA<br>Applied | Fermenter # |
| 0 | 0.20 | 0.20 | 0.00 | 1.10 | 1.10 | Finer | Spirizyme+ | 1 |
| 0.20 | 0.20 | 0.39 | 0.02 | 1.10 | 1.12 | Finer | Spirizyme+ | 2 |
| 0.59 | 0.20 | 0.78 | 0.05 | 1.10 | 1.15 | Finer | Spirizyme+ | 3 |
| 0.00 | 0.20 | 0.20 | 0.00 | 1.10 | 1.10 | Coarser | Spirizyme+ | 4 |
| 0.20 | 0.20 | 0.39 | 0.02 | 1.10 | 1.12 | Coarser | Spirizyme+ | 5 |
| 0.59 | 0.20 | 0.78 | 0.05 | 1.10 | 1.15 | Coarser | Spirizyme+ | 6 |
| 0.00 | 0.08 | 0.20 | 0.00 | 1.10 | 1.10 | Finer | Distillase | 7 |
| 0.20 | 0.08 | 0.39 | 0.02 | 1.10 | 1.12 | Finer | Distillase | 8 |
| 0.59 | 0.08 | 0.78 | 0.05 | 1.10 | 1.15 | Finer | Distillase | 9 |
| 0.00 | 0.08 | 0.20 | 0.00 | 1.10 | 1.10 | Coarser | Distillase | 10 |
| 0.20 | 0.08 | 0.39 | 0.02 | 1.10 | 1.12 | Coarser | Distillase | 11 |
| 0.59 | 0.08 | 0.78 | 0.05 | 1.10 | 1.15 | Coarser | Distillase | 12 |

72 Hour Results

| Fermenter # | % Ethanol | Residual Carbohydrates Wt. % | | | | | Byproducts Wt. % | | | Total % Solids | Residual Starch % dw |
|---|---|---|---|---|---|---|---|---|---|---|---|
| | | DP4+ | DP3 | Malt | Gluc | Fruc | Glyc | Lactic | Acetic | | |
| 1 | 17.84 | 0.36 | 0.01 | 0.01 | 0.01 | 0.12 | 0.89 | 0.07 | ND | 15.31 | 17.09 |
| 2 | 18.17 | 0.36 | 0.01 | 0.01 | 0.01 | 0.12 | 0.89 | 0.06 | ND | 15.12 | 16.53 |
| 3 | 18.57 | 0.36 | 0.01 | 0.01 | 0.02 | 0.12 | 0.90 | 0.06 | ND | 14.72 | 16.31 |
| 4 | 19.46 | 0.45 | 0.02 | 0.03 | 0.28 | 0.16 | 0.92 | 0.04 | ND | 14.36 | 15.14 |
| 5 | 19.65 | 0.44 | 0.02 | 0.04 | 0.57 | 0.17 | 0.92 | 0.04 | ND | 14.49 | 14.97 |
| 6 | 19.74 | 0.42 | 0.01 | 0.04 | 0.59 | 0.19 | 0.90 | 0.04 | ND | 14.40 | 13.81 |
| 7 | 14.42 | 0.37 | 0.01 | 0.01 | ND | 0.05 | 0.65 | 0.16 | ND | 20.24 | 36.27 |
| 8 | 15.89 | 0.37 | 0.01 | 0.01 | ND | 0.10 | 0.77 | 0.07 | ND | 16.68 | 27.24 |
| 9 | 17.25 | 0.37 | ND | 0.01 | 0.01 | 0.11 | 0.86 | 0.06 | ND | 15.97 | 20.43 |
| 10 | 17.19 | 0.46 | 0.01 | 0.01 | 0.01 | 0.10 | 0.80 | 0.05 | ND | 18.19 | 31.43 |
| 11 | 18.35 | 0.44 | 0.01 | 0.01 | 0.03 | 0.14 | 0.87 | 0.05 | ND | 16.16 | 24.07 |
| 12 | 19.30 | 0.42 | 0.01 | 0.01 | 0.06 | 0.15 | 0.92 | 0.05 | ND | 14.95 | 18.01 |

Results and Discussion

Figure 4A:
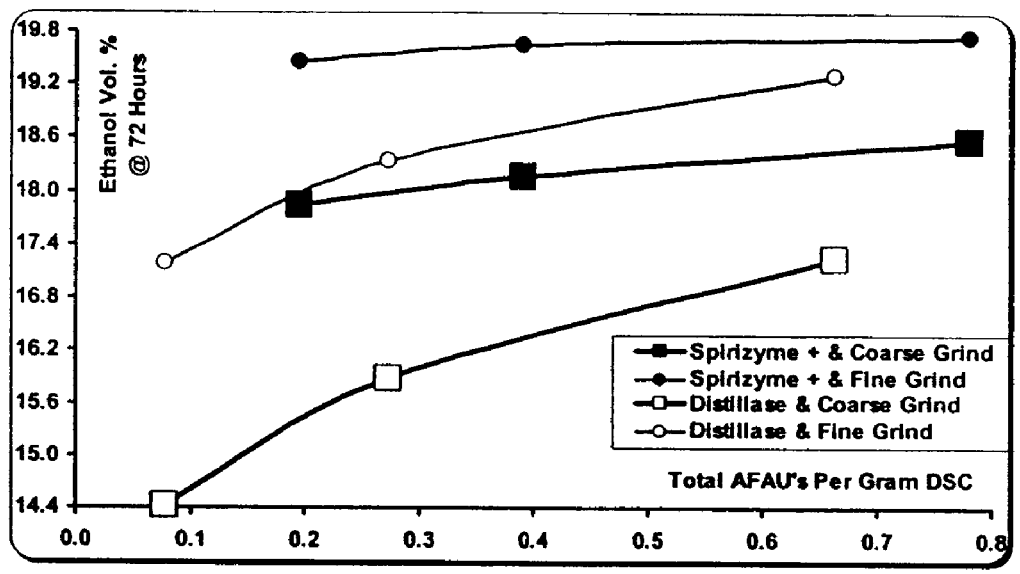
FIGS. 4A-4C illustrate the effect of grind size, glucoamylase type, and acid fungal amylase dosage on fermentation efficiency in the present process.
Figure 4B:
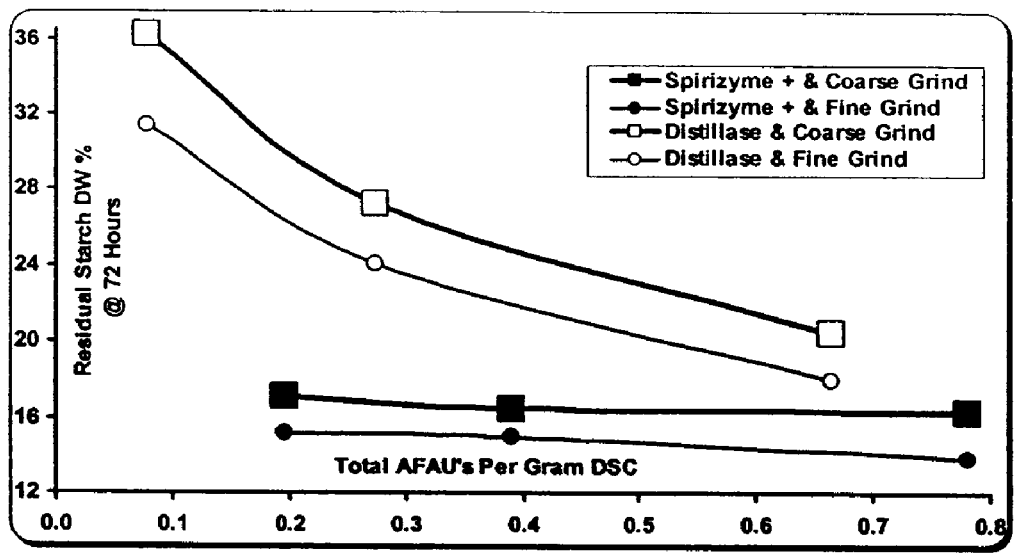
Figure 4C:
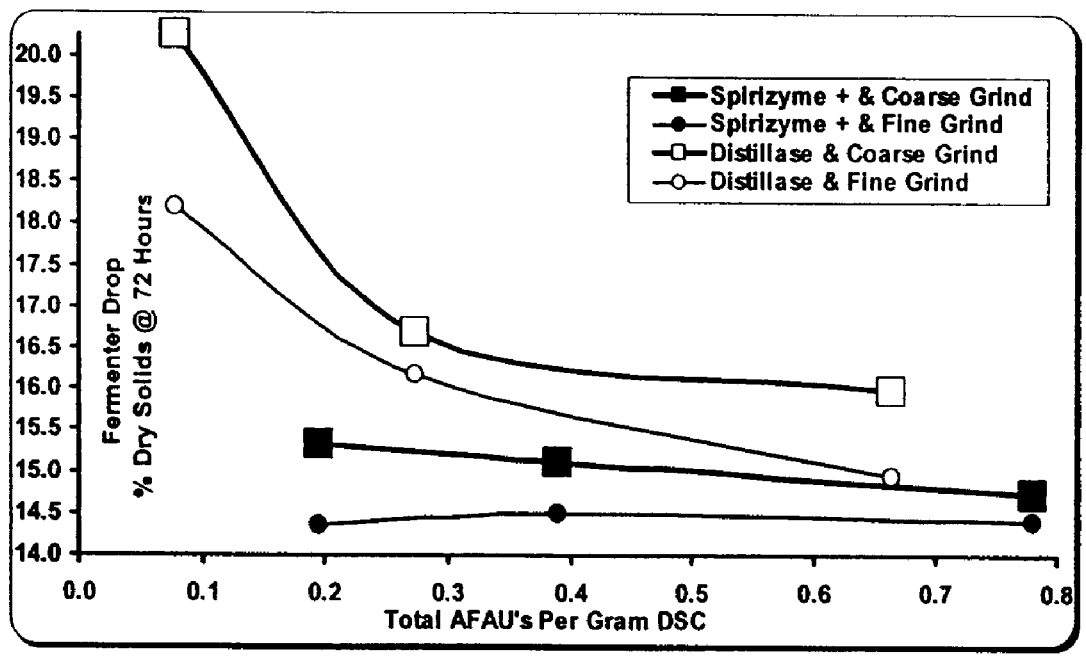
Figure 5A:
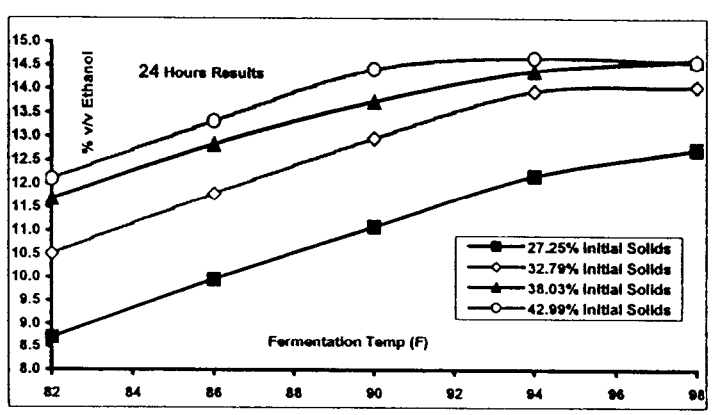
FIGS. 5A-5J illustrate the effect of initial dry solids and temperature on fermentation performance in the present process.
Figure 5B:
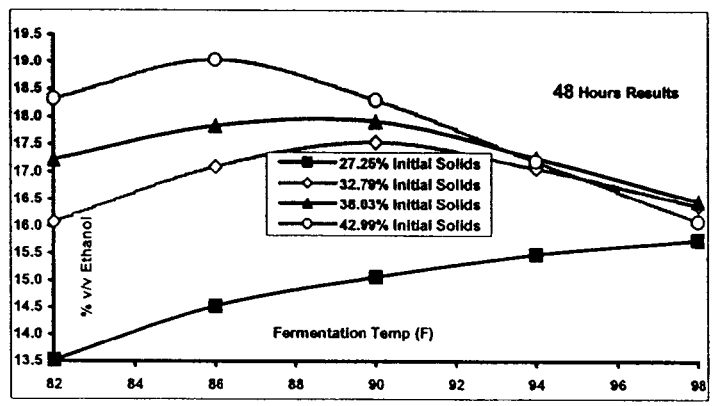
Figure 5C:
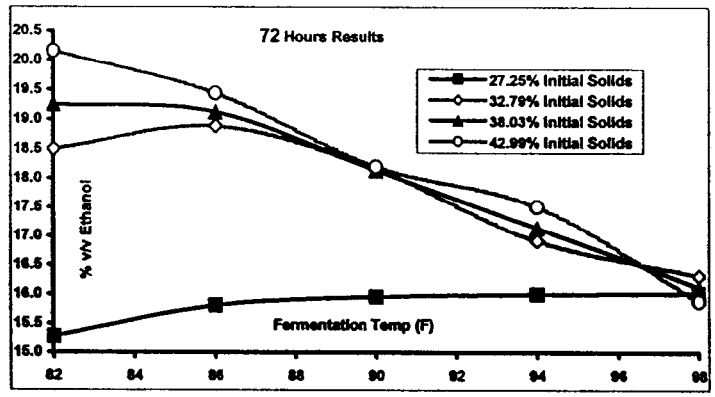
Figure 5D:
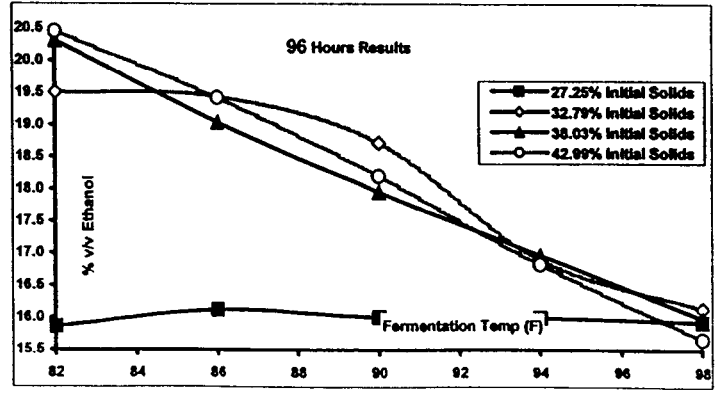
Figure 5E:
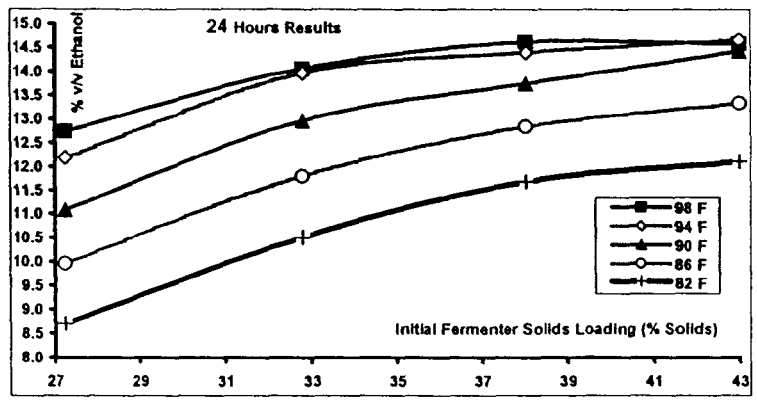
Figure 5F:
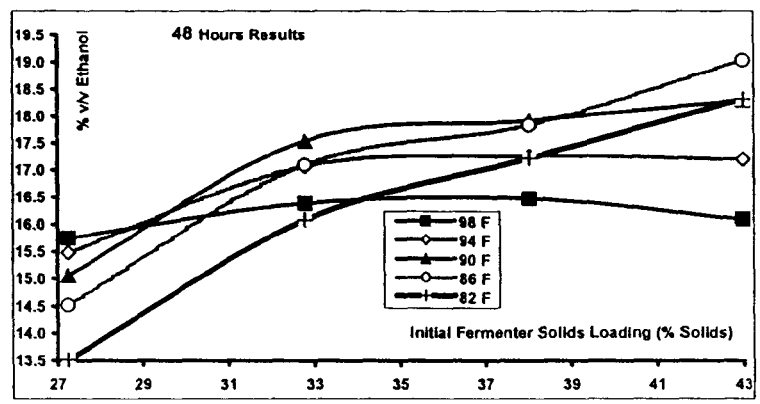
Figure 5G:
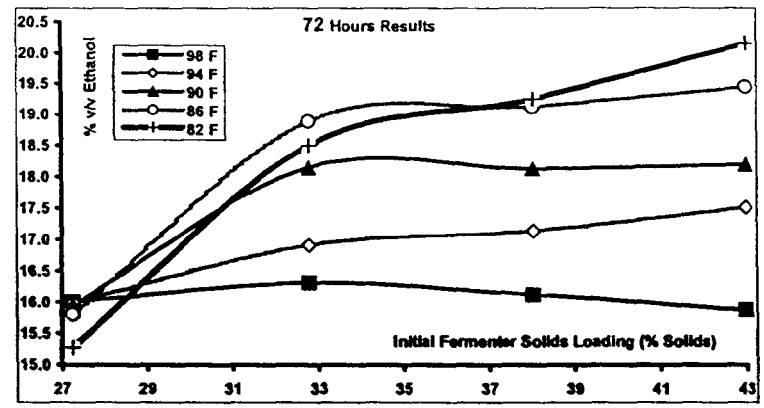
Figure 5H:
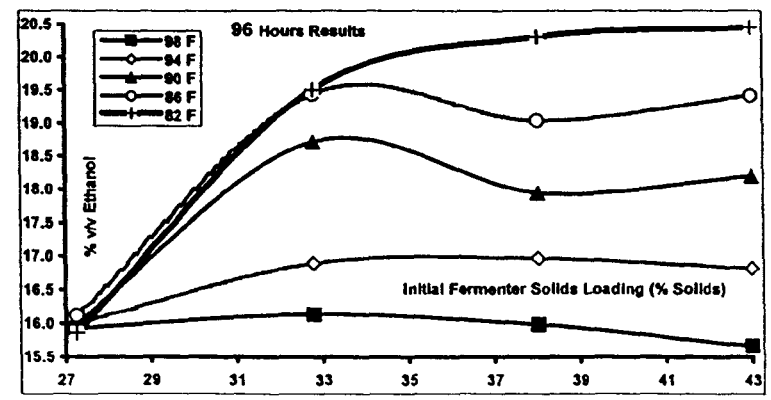
Figure 5I:
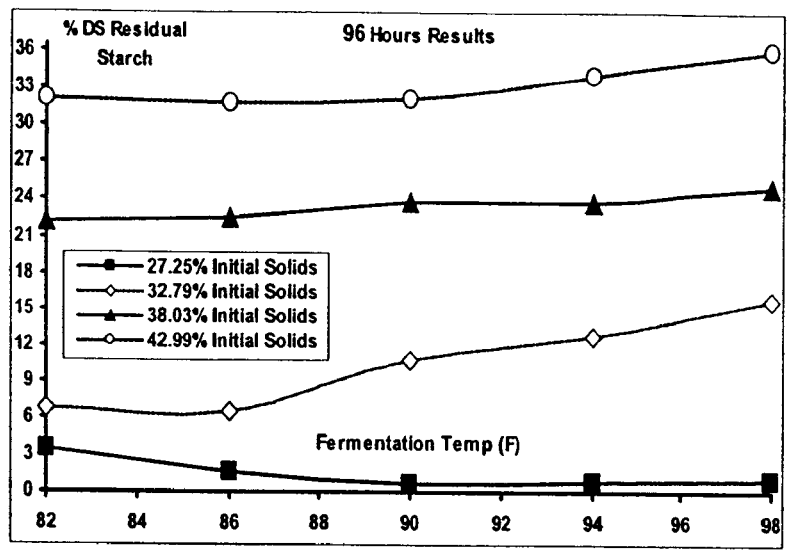
Figure 5J:
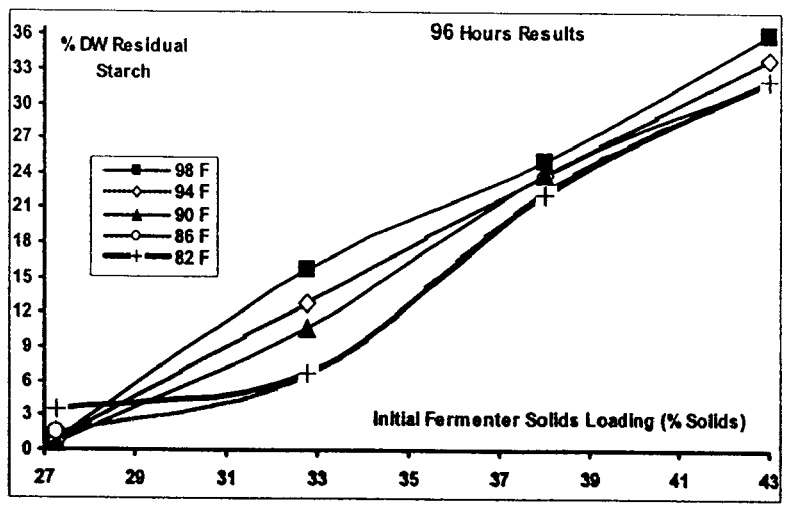

Final fermenter results are shown in FIGS. 4A, 4B, and 4C. Conventional glucoamylase enzymes such as Distillase from Genencor International contained a very low level of acid fungal amylase activity. Spirizyme Plus contained about 2.5 times as much AFAU activity per ml of enzyme and exhibited improved performance for hydrolyzing raw starch. SP 288 acid fungal amylase contained a relatively low level of glucoamylase.

It was possible to gain an understanding of the importance of grind size, glucoamylase dosage level, and acid fungal amylase dosage level on fermentation performance. Improved results were obtained when a "finer" grind was combined with glucoamylase containing enhanced acid fungal amylase levels. With a courser grind, high dosage levels of glucoamylase including acid fungal amylase yielded improved fermentation performance. Glucoamylase including acid fungal amylase provided benefits as grind size decreased.

Example 6

Impact of Fermenter Dry Solids Loading and Temperature on Fermenter Kinetics and Ethanol Performance An embodiment of the present invention was employed to produce ethanol from corn. This process produced high alcohol corn beer, high protein, high fat, and high fiber distiller's dried grain. Comparison with conventional saccharification and liquefaction process indicate superior performance of the present method.

Materials and Methods

Example 6 was set up in a manner similar to prior examples except the initial fermentation solids and temperature were varied as described in the presentation of the results.

Results

An interesting feature of the present raw starch fermentation process is the ability to enhance the rate of fermentation through increasing the solids content or initial temperature of fermentation. Solids loading, temperature, grind size, glucoamylase dosage, acid fungal amylase dosage, and yeast dosage can be combined to increase the performance of raw starch fermentation. FIGS. 5A, 5B, 5C, 5D, 5E, 5F, 5G, 5H, 5I, and 5J illustrate the influence of temperature at different solids loadings.

The residual starch values reported for this Example suggest that temperature can be used to improve the efficiency of raw starch fermentations at intermediate fermentation gravities, which are defined as fermentation solids levels which would yield between 15% to 18% ethanol. The fermentation temperature could be used to accelerate raw starch fermentations so that they finish in less than 48 hours, yet still achieve alcohol levels of 15% to 18%, with acceptable residual starch levels. The increased fermentation set point will help to accelerate enzymatic conversion of native starch to glucose, which appears to be the rate limiting step in the raw starch process. Fermentation performance using higher temperature set points is an aspect of the process for intermediate ethanol ranges, especially when viewed from the perspective of prior examples establishing that raw starch fermentations can tolerate a higher level of residual starch in the residual distillers dried grains and with distillers dried grains solubles, and still produce excellent quality DDG or DDGS according to the proximate analysis. Alternatively, the dry substance of raw starch fermentations can be increased by approximately 20% to increase the rate of fermentation, while producing higher alcohol content in the fermenter and more DDGS with excellent quality even if the residual starch levels are high. By balancing the above inputs, a yield versus throughput economic optimization can be done with a significant decrease in difficulty. The ease of operating a high gravity, high throughput process while producing a saleable DDGS is significantly enhanced by the raw starch process.

Example 7

Advantageous Aspects of Ethanol Production by the Present Process

A variety of fermentation runs were conducted and the results were evaluated and compiled to demonstrate the increased alcohol production and production of distiller's dried grain by the present process.

Ethanol Production

Figure 6A:
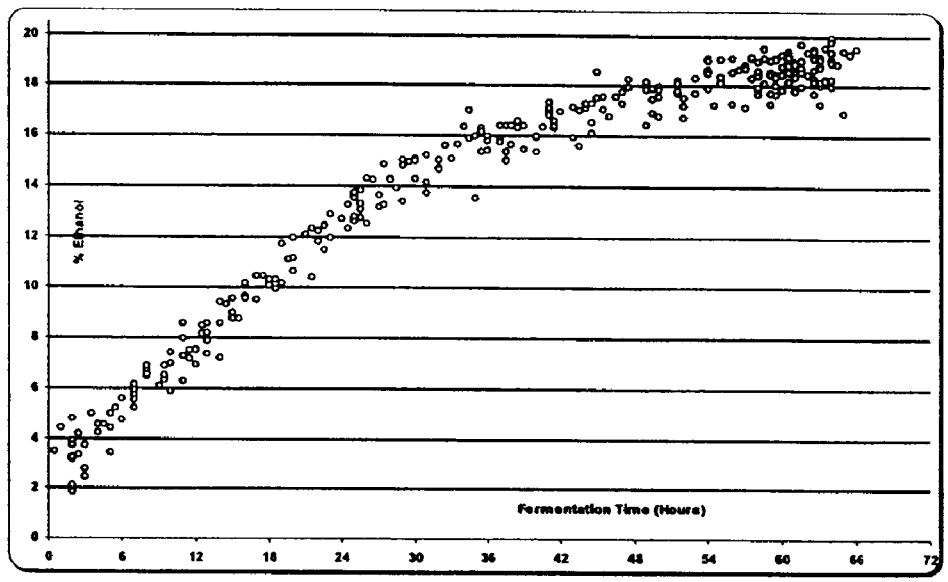
FIGS. 6A and 6B illustrate high levels of ethanol production from the process of the present invention using simultaneous saccharification and fermentation (SSF) batch or continuous modes of operation.
Figure 6B:
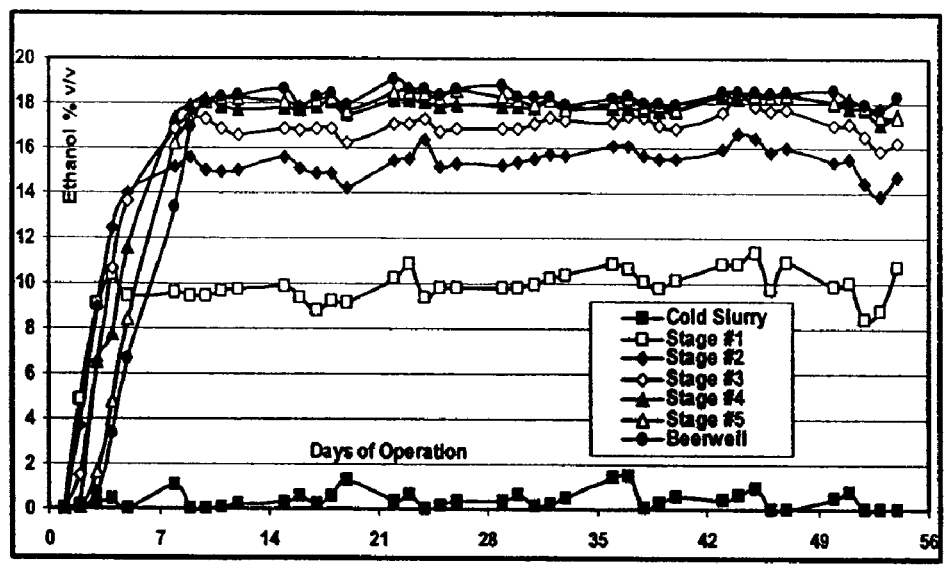

The present method produced ethanol containing corn beer with greater than 18 vol-% ethanol. Runs produced at least 18 vol-% ethanol and up to 23 vol-% ethanol within 48 to 96 hours of incubation and fermentation. The beer contained these high levels of ethanol even when it also included higher levels of residual starch. After 24 hours of incubating and fermenting the corn beer contained 9-16.5 or 12-15 vol-% ethanol. After 48 hours of incubating and fermenting the corn beer contained 13-20 vol-% ethanol. Ethanol production was linear up to a level of 14-16 vol-%. A compilation of ethanol production results from various runs is illustrated at least in FIGS. 6A and 6B.

Figure 7:
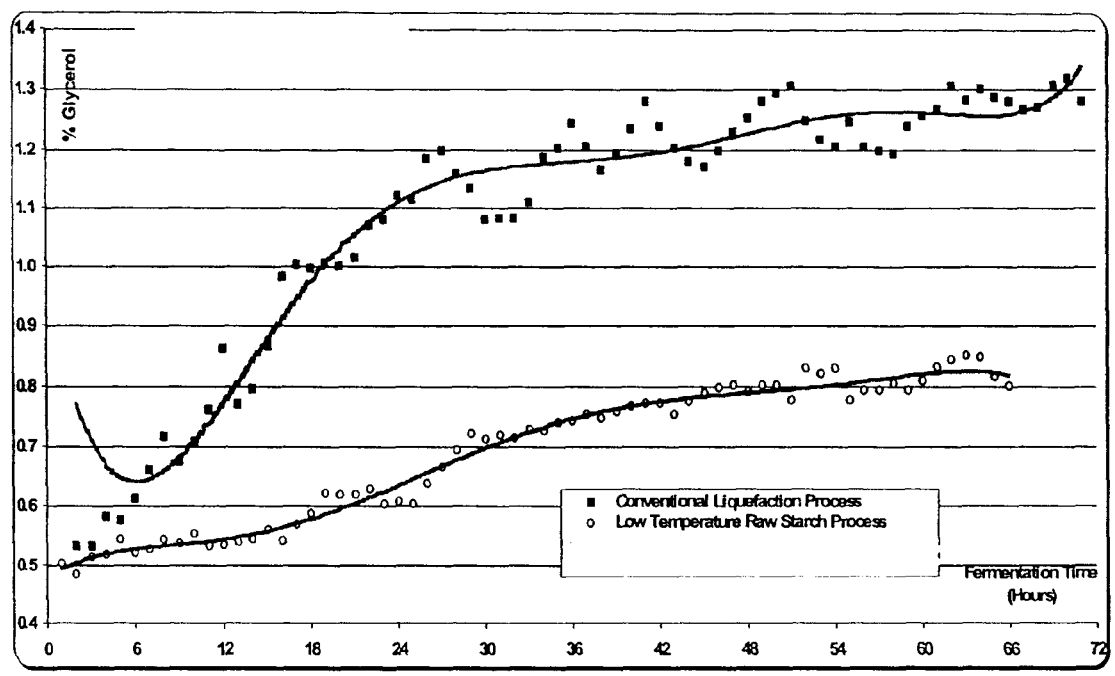
FIG. 7 illustrates that the present process maintained low levels of glycerol using SSF batch operations.
Figure 8:
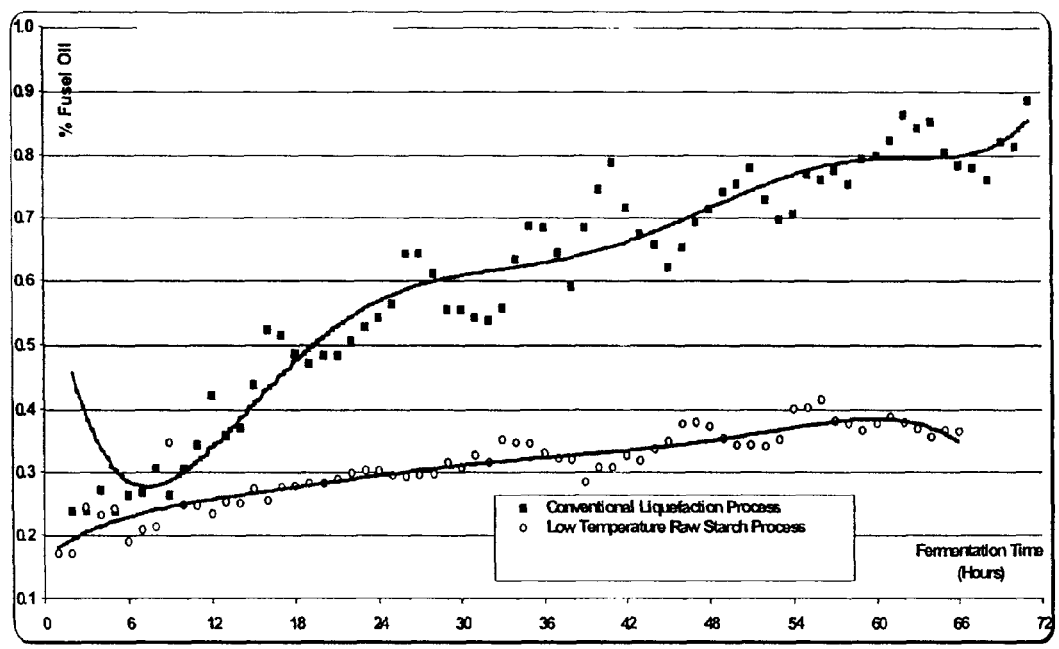
FIG. 8 illustrate that the present process maintained low levels of fusel oils during SSF batch operations.

The beer contained approximately 0.4 to 0.5 wt-% less glycerol than conventional fermentation at otherwise identical fermentation conditions (FIG. 7). The beer contained less extracted oil from the germ fraction, resulting in reduced fouling and lower VOC emissions in the water vapor during drying of the residual animal feed product. (Table 1) The beer contained less extracted oil from the germ fraction, resulting in reduced fouling and lower CO emissions in the water vapor during drying of the residual animal feed product (Table 1). The beer contained less fusel oil (FIG. 8), which inhibits yeast cell growth and fermentation if these alcohol compounds are unintentionally recycled in distillation side stripper bottoms streams. Fusel oils are also an undesirable component of potable alcohol manufacturing operations, so the present process offers an improved method of production of potable alcohol. The beer also contained less lactic and acetic acid relative to the conventional process. The beer also contained higher yeast cell counts, which contributes to improved feed products.

In addition, the present process maintained yeast at or above 300 cells/mL in these numerous runs. Yeast budding was observed in at least 40% of the yeast from hours 0-20 of incubating and fermenting and/or at least 15-20% of the yeast after hours 60 of incubating and fermenting. These yeast counts and budding are higher than observed in the conventional process.

Example 8

The Present Process Maintains Low Levels of Glucose, Maltose (DP2), Maltotriose (DP3), and Dextrins (DP4+)

The levels of glucose, maltose (DP2), maltotriose (DP3), and dextrins (DP4+) produced by an embodiment of the present invention was compared to a conventional process. The present method exhibited decreased levels of glucose, maltose (DP2), maltotriose (DP3), and dextrins (DP4+) respectively. Comparison of the level of glucose to the conventional process indicates superior performance of the present method.

Materials and Methods

Experiment 1

Whole Corn and corn flour was obtained from Dakota Ethanol LLC in Wentworth, S.D. The whole corn for continuous ethanol fermentation examples was ground through a 0.5 mm screen as in prior examples using a lab scale hammermill. The whole corn for SSF examples was ground through a #4 screen using a commercial scale Bliss hammermill, which achieved approximately 50% of the ground flour passing through a 0.5 mm screen as measure in a sieve test of the flour.

Batch fermentations were set up in a similar manner as Example 1. Continuous ethanol fermentation was evaluated in a bench top system consisting of a refrigerated cold slurry tank followed by five (5) fermenters operating in continuous mode and finishing with a beerwell collecting the fermented beer. The volume of each fermentation stage was approximately two (2) liters. When operated at a mash flow rate of 1.5 to 2.0 ml per minute, the average fermentation time was approximately ninety-six (96) hours. Average fermenter fill solids was approximately 30-35% dry solids corn, depending on the starch content of the substrate. The mash slurry for feeding fermentation was prepared every 3 to 4 days and maintained between 6 to 12 degrees Centigrade to discourage bacterial growth in the feed tank.

The mash preparation procedures did not sterilize the mash prior to fermentation, and the fermentation train was operated with no antibiotic addition to inhibit bacterial contaminants. The mash was stored at a cold temperature to reduce the amount of work required for substrate preparation. 15 to 20 ml of 50% urea liquor was added to the cold slurry tank, which had a final mash volume of approximately 9000 liters.

Each fermenter in the continuous series was fed from the prior fermenter, while the first fermenter was fed directly from the cold slurry tank. Fermentation temperature was held at a constant 82° F. through the five (5) stage fermentation.

Glucoamylase was dosed into the first fermenter to provide a dosage of approximately 2.0 to 2.4 AGU's per gram dry substance corn. Fali yeast, obtained from Fleischmann's Yeast, was added at a rate of approximately 0.65 grams per liter of slurry makeup, and was batched into the cold slurry each time fresh mash was prepared.

Experiment 2

Figure 16A:
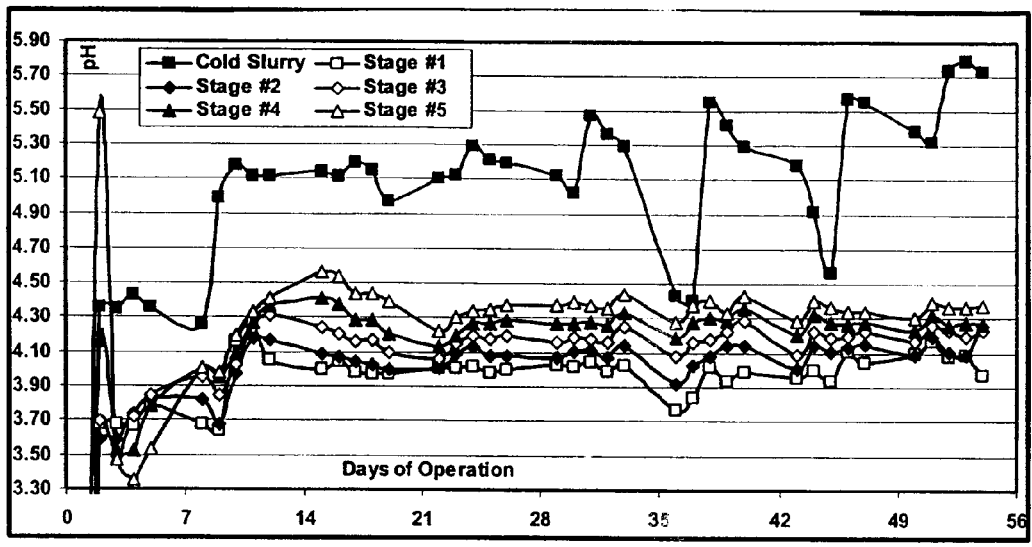
FIGS. 16A-C illustrate that the process of the present invention is capable of stable operation in a continuous mode of operation without significant loss due to acid producing bacterial contamination.

A continuous fermentation run was set up employing the procedure described above for experiment 1. Lactic acid and acetic acid measurements were taken at various times and stages during the continuous multistage fermentation process. Toward the end of the run, the initial slurry pH was purposely increased, as shown, to challenge the system microbiologically. In certain circumstances, slurry pH was intermittently lowered to keep contamination in check (see, e.g., FIGS. 16A, 16B, and 16C).

Experiment 3

Data in Experiment 3 was created from the continuous fermentation system examples described in Examples 1,2, and 8. Residual starch was measured using a commercially available starch assay (the Megazyme® starch assay). This assay works for samples ranging in starch content from 0-100%, which makes it applicable for residual starch analysis as well as starch assaying in raw grain. This method is an enzymatic conversion based assay that uses alpha amylase and amyloglucosidase to convert starch to glucose. The resulting glucose is then measured via HPLC and the starch content calculated.

Results and Discussion

Figure 9A:
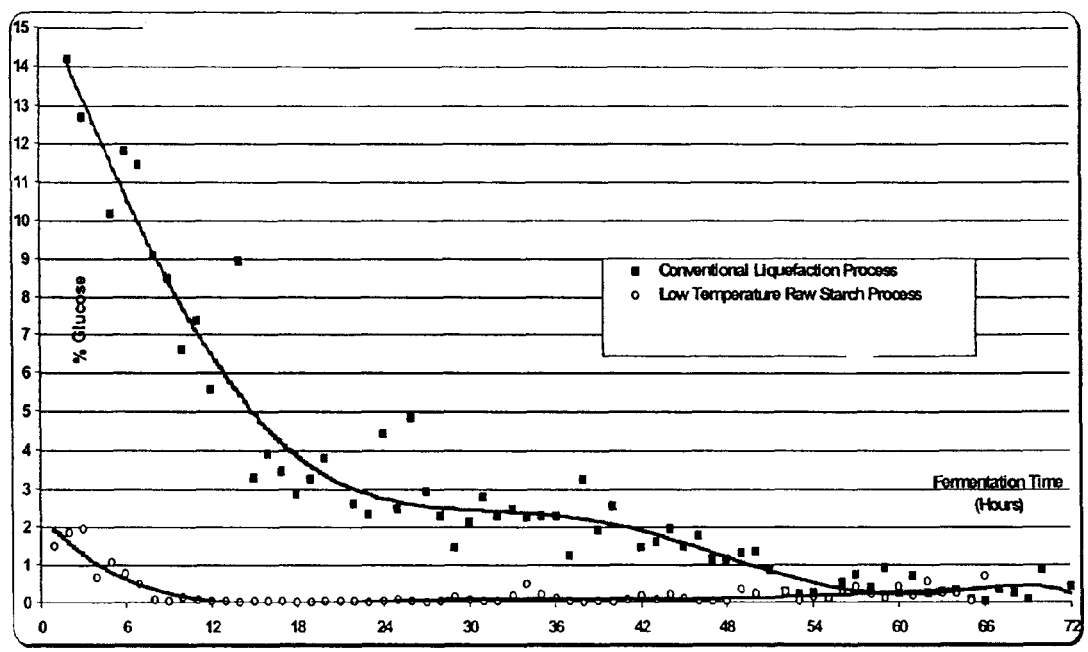
FIGS. 9A and 9B illustrate that the present process maintained low levels of glucose during SSF batch or continuous fermentation modes of operation.
Figure 9B:
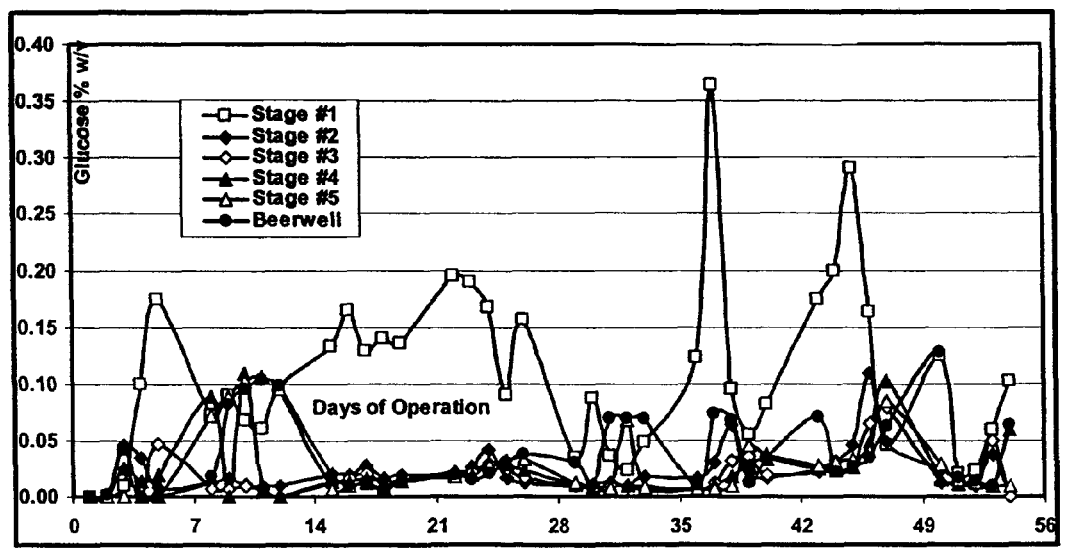

FIGS. 9A and 9B illustrate that the present process maintained low levels of glucose during simultaneous saccharification and fermentation (SSF) and continuous raw starch fermentations. Although not limiting to the present invention, it is believed that this low level of glucose reduces potential reactions such as reversion, condensation, or Maillard Browning Reactions. Such reactions in turn can reduce ethanol yield. The data compiled in this example demonstrates that the process maintained glucose at levels at or below 3 wt-% for the entire run and at or below 1 wt-% for about 90% of the run. In particular, the process maintained glucose at levels at or below 1 wt-% from hours 12-54 of incubating and fermenting.

Figure 10A:
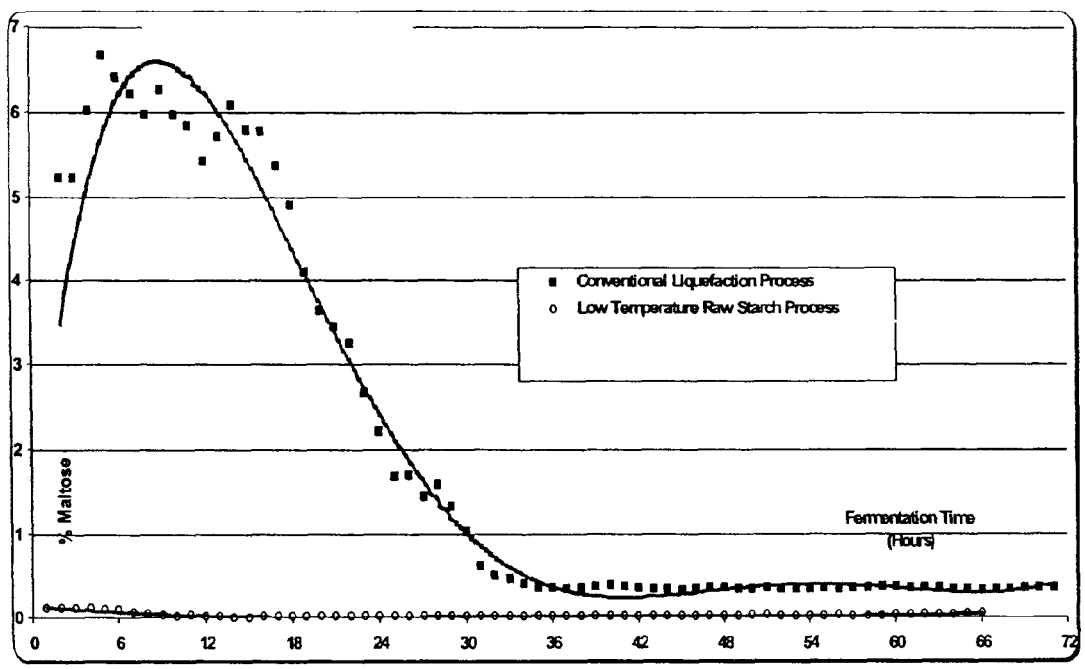
FIGS. 10A and 10B illustrate that the present process maintained low levels of maltose during SSF batch or continuous fermentation modes of operation.
Figure 10B:
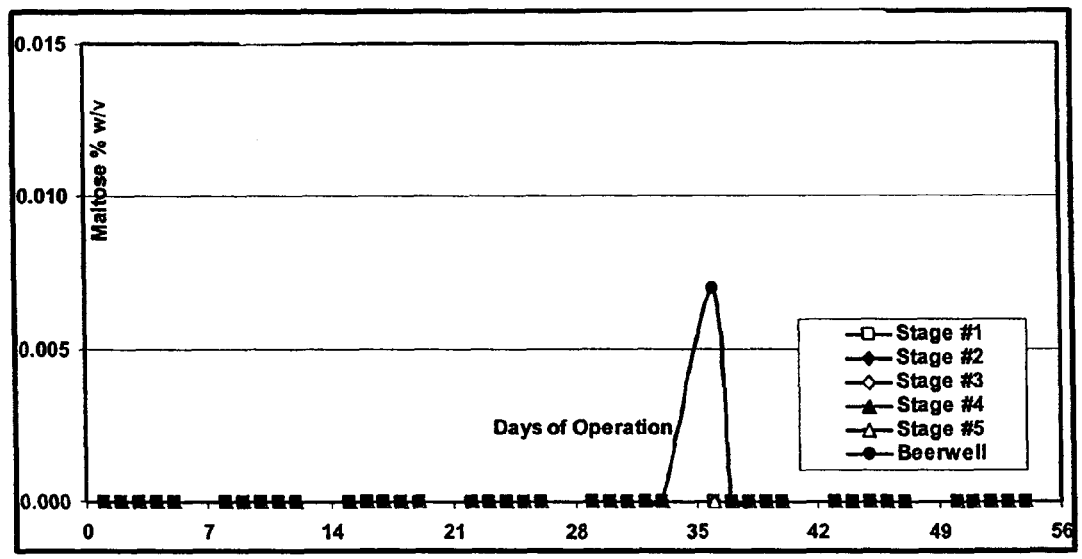
Figure 11A:
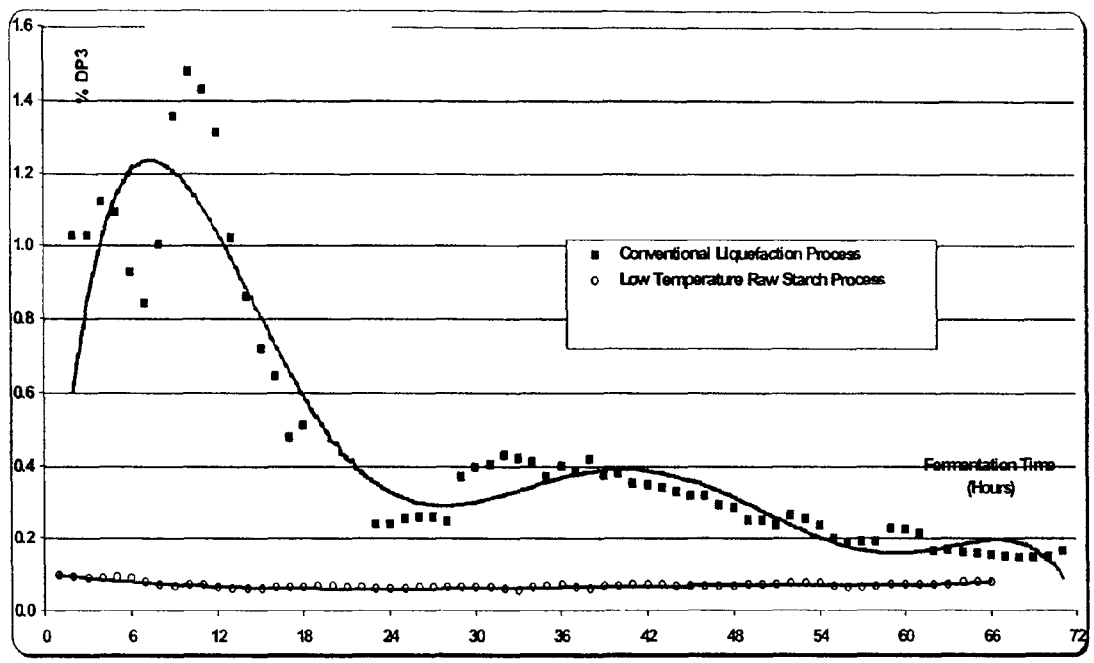
FIGS. 11A and 11B illustrate that the present process maintained low levels of maltotriose (DP3) during SSF batch or continuous fermentation modes of operation.
Figure 11B:
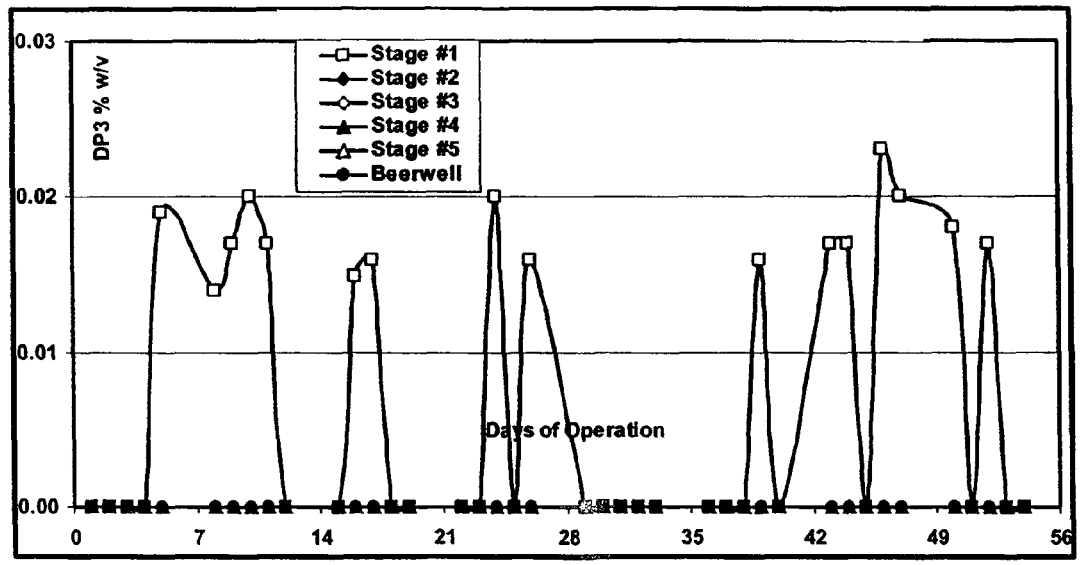

FIGS. 10-12 illustrate that the present process maintained low levels of dextrin during SSF and continuous raw starch fermentation. FIGS. 10A and 10B illustrate that the present process maintained maltose (DP2) at levels at or below about 0.2 wt-% during simultaneous saccharifying and fermenting and below about 0.34 wt-% during continuous raw starch fermentation. The data shown in FIG. 11A demonstrate that the process maintained low levels of maltotriose (DP3) during simultaneous saccharifying and fermenting at levels at or below 0.2 wt-% and at or below 0.1 wt-%. The data shown in FIG. 11B demonstrate that the present process maintained low levels of maltotriose (DP3) during a continuous raw starch fermentation at levels at or below 0.25 wt-%.

Figure 12A:
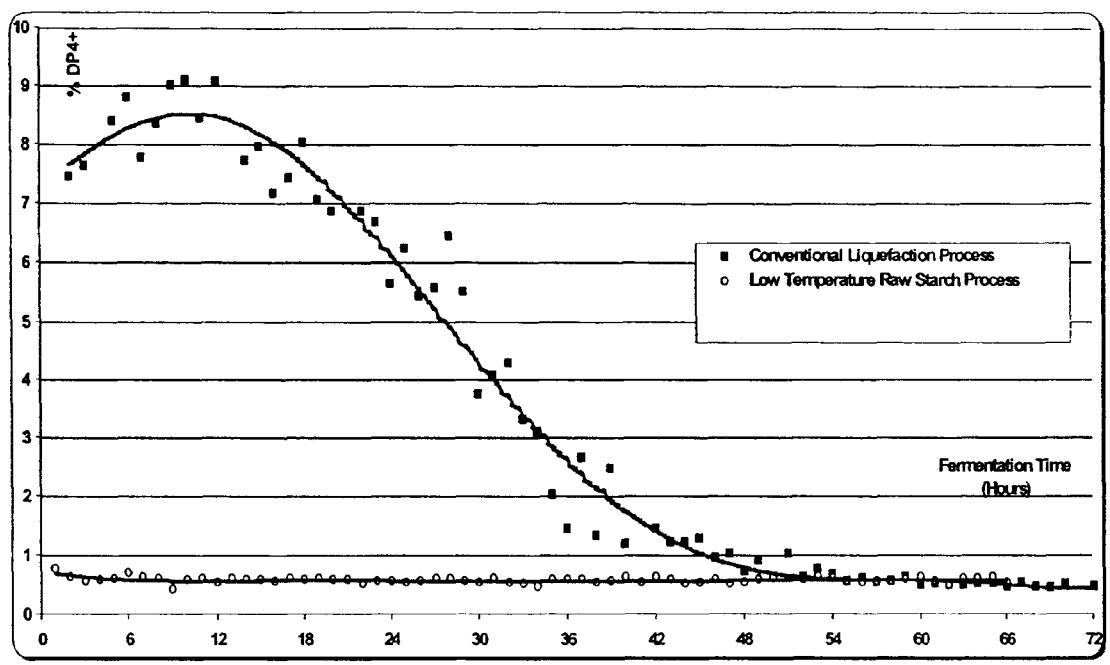
FIGS. 12A and 12B illustrate that the present process maintained low levels of dextrins (DP4) during SSF batch or continuous fermentation modes of operation.
Figure 12B:
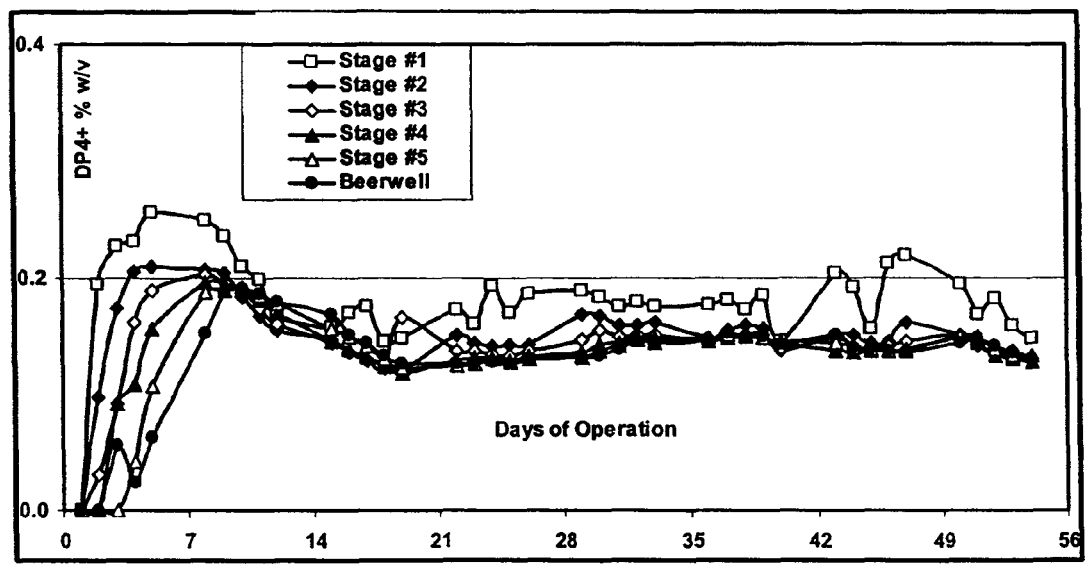

The data shown in FIG. 12A demonstrate that the process maintained low levels of dextrins (DP4+) during simultaneous saccharifying and fermenting at levels at or below 1 wt-% and at or below 0.5 wt-%. The data shown in FIG. 12B demonstrate that the process maintained low levels of dextrins (DP4+) during continuous raw starch system at levels at or below 0.3 wt-%.

Figure 16B:
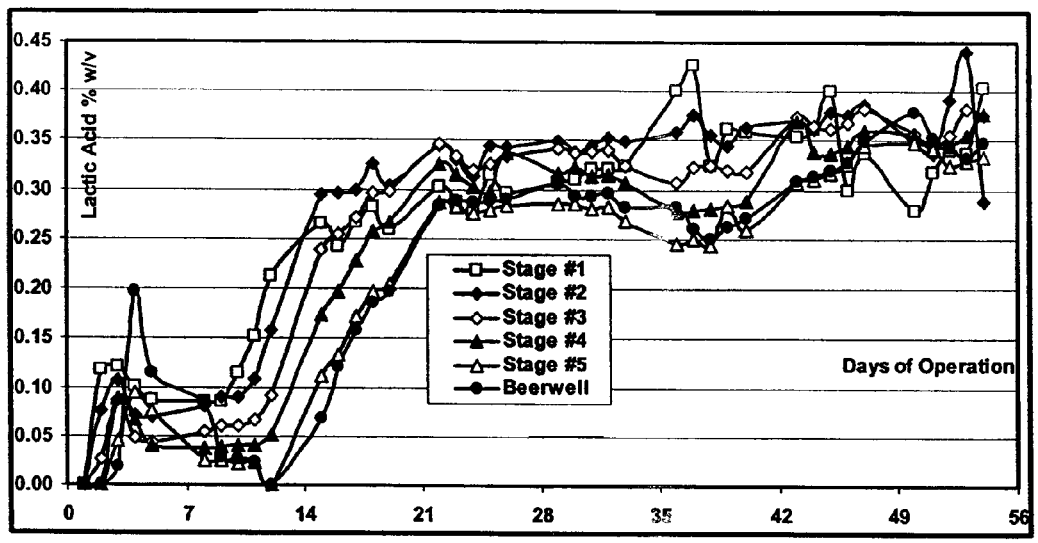
Figure 16C:
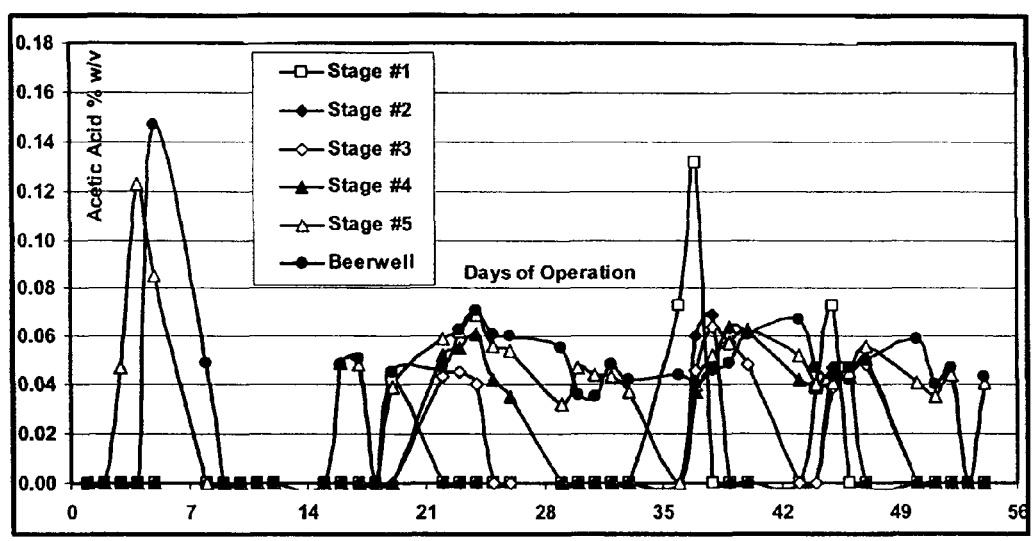

The results of experiment 2 show that initial slurry pH levels up to approximately 5.8 in the present method (FIG. 16A) resulted in acceptable ethanol yields and maintained acidic fermentation contaminants within a tolerable range (e.g., fermentation was not inhibited). The percentage of lactic acid remained less than 0.45 (in most cases less than 0.35) (FIG. 16B). The percentage of acetic acid remained less than 0.18 (in most cases less than 0.06) (FIG. 16C). This embodiment of the present method resulted in consistently low lactic and acetic acid levels and stable pH levels. This resulted in greater ethanol production, which was at least in part likely due to less yeast stress.

Figure 17:
FIG. 17 illustrates that the present process is capable of achieving low residual starch levels in a continuous mode of operation.

The results of experiment 3 demonstrate that a continuous embodiment of the present method produced residual starch levels lower than that produced by the conventional process (FIG. 17). The residual starch levels produced using this embodiment of the present method remained lower than the residual starch levels of the conventional process (FIG. 17). The percentage of starch produced using this embodiment of the present method remained at about twenty (e.g. 21) or less (FIG. 17) whereas the percentage starch produced using the conventional process was as high as 27 (FIG. 17).

Discussion

Although not limiting to the present invention, it is believed that as glucose is formed during fermentation, it is quickly metabolized by the yeast, which resulted in low glucose levels. The slight increase in glucose observed at the end of fermentation suggests a drop in yeast viability. Again, not to limit the present invention, this can be explained by a decrease in yeast viability and fermentation that results in glucose production rates exceeding metabolic utilization rates (fermentation of glucose no longer keeps up with production).

According to an embodiment of the present invention, temperature staging can be employed to minimize residual glucose production. That is, the temperature of the fermentation can be reduced as the fermentation progresses. It is believed that, in general, for every 10° C. (18° F.) increase in temperature, the rate of an enzymatic reaction approximately doubles. In an embodiment of the present method, for example, enzyme action can be slowed by decreasing the temperature of the fermentation mixture after a time period, such as after 30 hours. It is believed that cooling also maintains yeast viability, so that fermentation can continue to utilize the glucose that has been formed. Conventional commercial variations of multistage continuous fermentation processes exist. One such conventional process includes running a saccharification stage prior to fermentation to provide fermentable glucose for a more rapid yeast fermentation. The present process does not require a saccharification stage before fermentation and produces improved results. Another conventional continuous process includes aerating the $1^{st}$ fermentor, and possibly the second fermentor, to encourage yeast growth. The present process provides improved results and does not require aeration of the fermentor. Some conventional continuous systems employ a yeast recycle method. The present method does not require yeast recycling and provides improved results. This embodiment of the present invention is superior to such conventional continuous fermentation systems. The present invention can employ simultaneous saccharification and fermentation of raw starch and can operate at high gravity. In an embodiment, the process of the present invention can produce ethanol at fast rates despite the apparent lack of adequate fermentable substrate.

A continuous ethanol production embodiment of the present method maintained low acidity levels throughout the fermentation cycle. These experiments indicate that an embodiment of the present method employing continuous fermentation created low, manageable levels of lactic and acetic acid. Low levels of lactic and acetic acid can be advantageous for maintaining a stable pH in fermentation, and can also decrease yeast stress and increase ethanol production.

A continuous ethanol production embodiment of the present method maintained lower starch levels throughout the fermentation cycle. Comparison of the present residual starch level to the conventional process provides an indication of advantageous performance from the present method. The mass balance of the present raw starch process suggests that residual starches can actually be higher in this process relative to the conventional, while still achieving a higher ethanol yield and improved proximate mass balance.

Example 9

The Present Process Produces DDGS With Less Caking and Compacting

The DDGS according to an embodiment of the present invention was compared to that produced by a conventional process. The present method produced an inventive DDGS that exhibited less caking compared to DDGS produced by the conventional process. The present DDGS with less caking is superior to conventional DDGS.

Materials and Methods

The DDGS was collected as a co-product of ethanol production from the conventional high temperature liquefaction process and from the process of the present invention. The caking/collapse assay was performed by filling a 500 ml cylinder with approximately 400 ml of DDGS. Attention was given to avoiding physical packing of the DDGS when filling the cylinder. After filling, a 4.4 cm diameter disc weighing 78 grams was placed on top of the DDGS, followed by placement of 1.5 kg of lead shot (in an appropriately sized plastic bag) on top of the disc. Assay preparation was completed by covering each cylinder with a plastic bag and sealing the apparatus with a rubber band to prevent moisture loss. The weight applied to the DDGS is used to exaggerate the effect and approximate the conditions which DDGS is exposed to during transport, for example, in a railcar. The level of the DDGS is noted at the beginning of storage and at various times during storage at a temperature of 50° C. The measured height of the collapsed (caked) DDGS was compared to the initial height of the DDGS. The measured height was compared to the initial height as an estimate of the tendency of the product to collapse or cake.

Results

Figure 13:
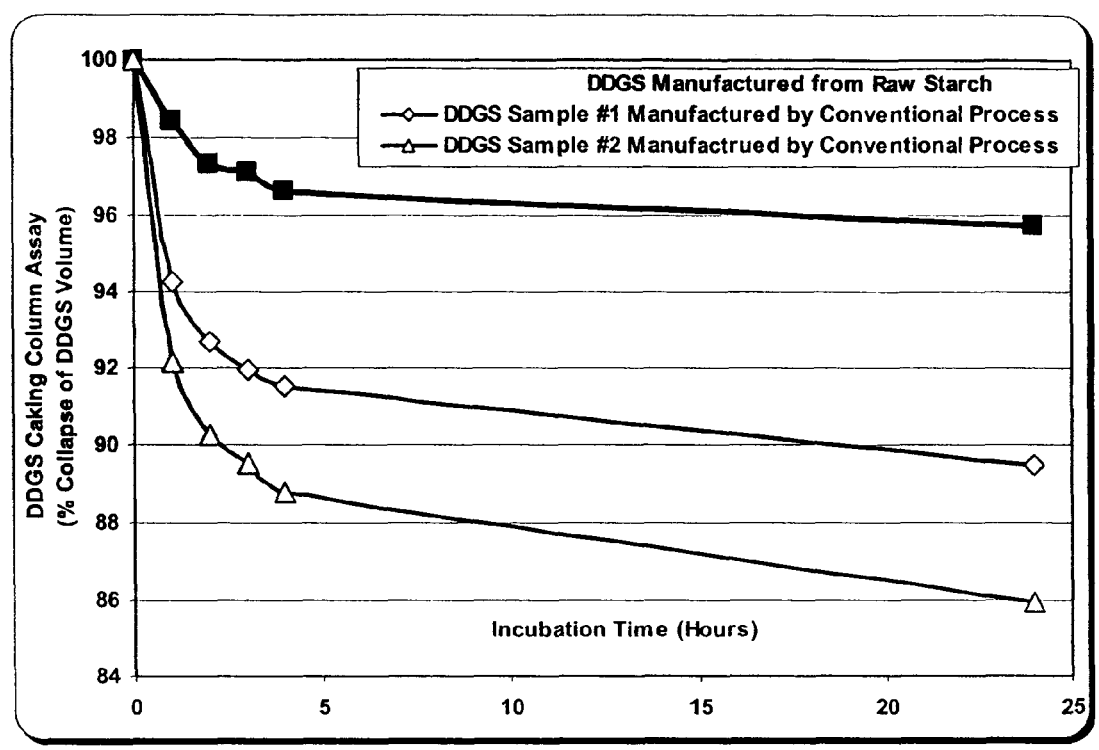
FIG. 13 Schematically illustrates that the present process impacts DDGS quality favorably based on caking tendency.

The DDGS from the present invention shows less caking collapse over time (FIG. 13) when compared to the DDGS of the conventional process. Over a twenty-five hour compaction time the DDGS according to the present invention collapsed only 4-5% of the initial volume as compared to 10-14% of the volume collapse for DDGS of the conventional process.

Discussion

The compaction of DDGS at controlled conditions models the DDGS caking observed in the containers of transportation vehicles, for example railcars and trucks. DDGS produced using the process of this invention exhibited less caking related collapse than that of the conventional process, indicating superior performance of the present method.

Although not limiting to the present invention, it is believed that the observed compaction is consistent with that suggested by glass transition theory. For example, glass transition temperature increases with molecular weight for polymers such as those found in DDGS. The present DDG includes higher levels of such polymers and should exhibit a higher glass transition temperature. It is believed that product moisture, storage temperature, and chemical composition can impact the transition of DDGS from an amorphous glass to an amorphous rubber phase. DDGS in the rubber phase compacts more readily that DDGS in the glass phase.

Example 10

The Present Process can Employ High Protein Corn to Produce High Protein DDGS and High Levels of Ethanol In an embodiment, the present invention can include fermenting high protein corn to produce high protein DDGS and high levels of ethanol. This provides for advantageous flexibility for processing high protein corn.

Materials and Methods

DDGS was collected as a co-product of ethanol production from fermentation of various corn hybrids with fermentations set up in a similar manner as Example 1. All fermentations were set up using identical conditions. Different corn hybrids were tested using various grind sizes using a lab scale hammermill. The hammermill screen size was varied from 0.5 mm to 4.0 mm to create flour particle sizes ranging from fine (0.5 mm screen) to coarse (4.0 mm screen).

Results

Figure 15A:
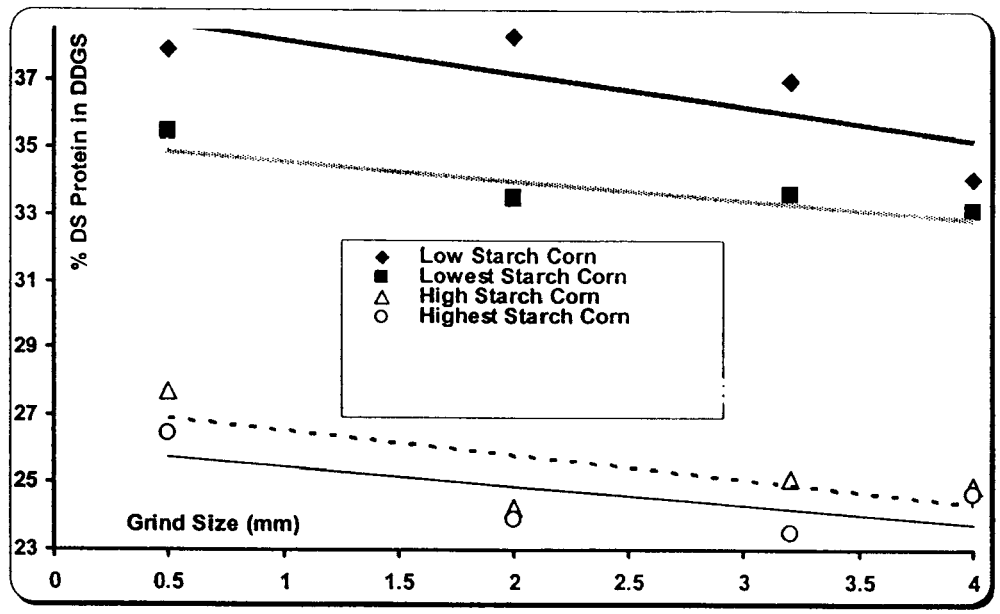
FIGS. 15A-D illustrate that the present process affords advantageous fermentation of non traditional feedstocks.
Figure 15B:
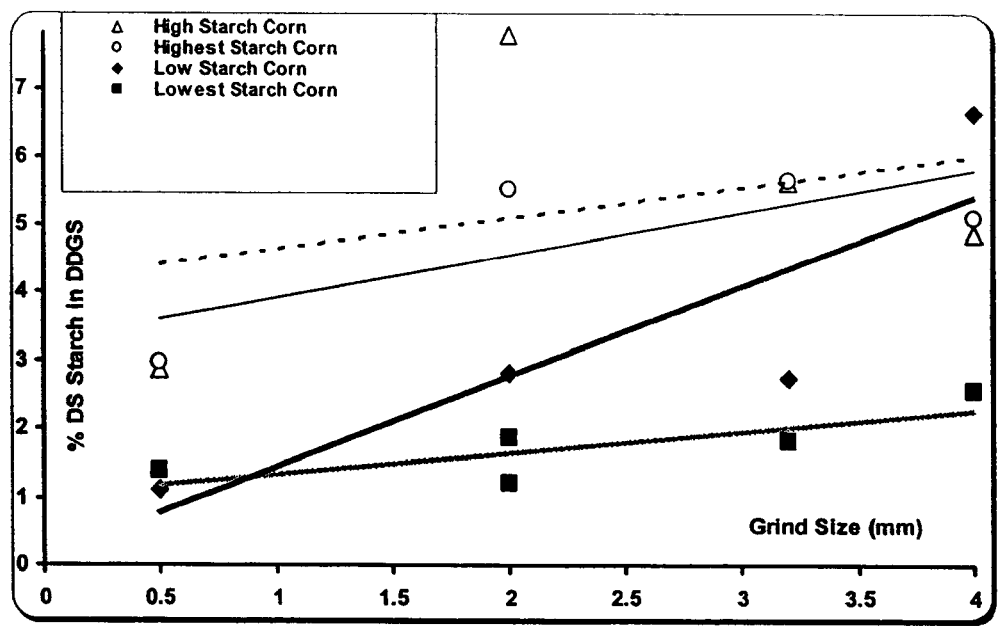
Figure 15C:
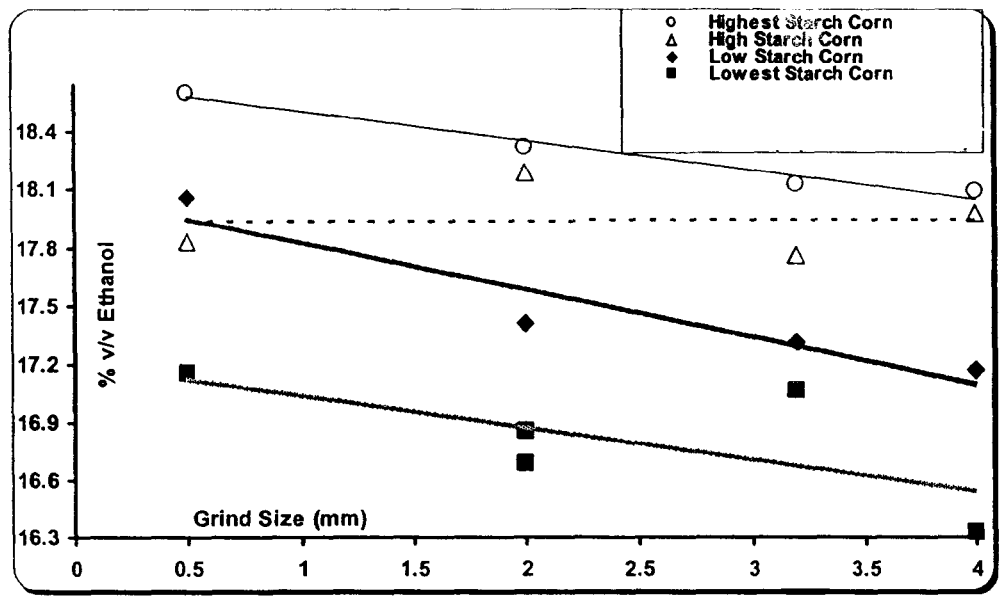
Figure 15D:
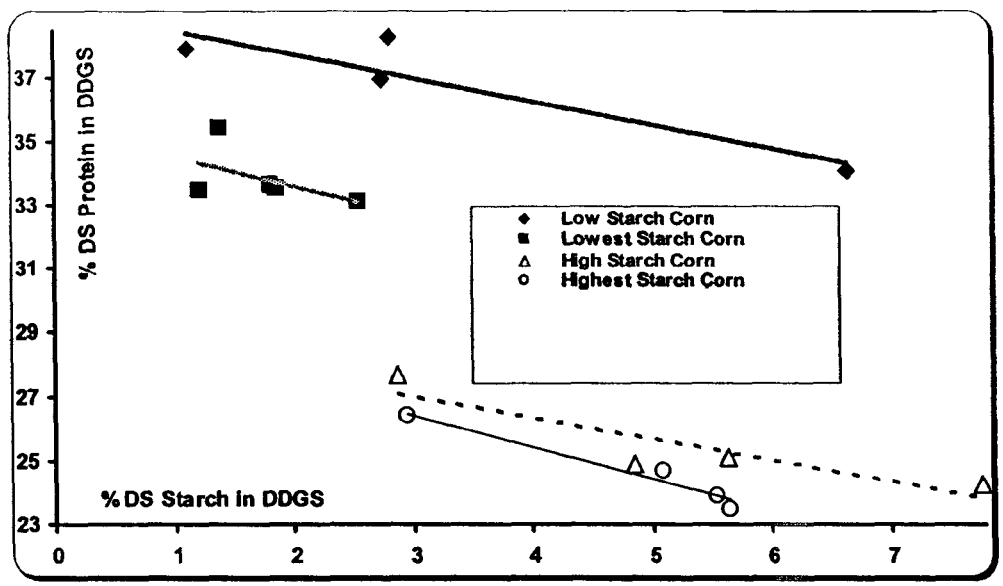

FIG. 15A illustrates the dependence of protein level in DDGS on grind size. This figure illustrates the inverse correlation between grind size and protein: as particle size increases the protein content of DDGS decreases for each tested corn hybrid (FIG. 15A). FIG. 15B illustrates the dependence of starch level in DDGS on grind size. This figure illustrates a positive correlation between grind size and starch content in: as particle size increases the starch content of the DDGS increases for each tested corn hybrid (FIG. 15B). FIG. 15C illustrates the dependence of ethanol production on grind size. This figure illustrates that as particle size decreases there is an increase in ethanol production (FIG. 15C).

Discussion

Reduced particle size arising from grinding of the corn enables higher ethanol yields and higher protein DDGS to be created. A strong correlation is also seen between the initial protein content of the corn and the resulting protein content of the DDGS. In the conventional process, higher protein corn is undesirable because it lowers fermentable starch content. The conventional process, being more constrained by viscosity arising from liquefaction, limits the processor's ability to maintain fermentables by increasing the solids level in fermentation. The present method is less constrained by viscosity, such that fermentable solids can be increased to maintain potential ethanol production titers while simultaneously producing a higher protein DDGS. The higher protein DDGS can be used for any of a variety of purposes.

It should be noted that there is significant effort within the current industry to encourage the use of "highly fermentable corn" hybrids. The "highly fermentable corn" hybrids can have a higher starch concentration and not a high protein concentration. This example demonstrates that higher protein corn hybrid varieties of standard #2 yellow corn can be used to obtain high levels of ethanol production. Despite standard #2 yellow corn lower starch contents, fermenter dry solids can be increased to maintain ethanol % levels in the fermenter while producing a higher protein DDGS.

Example 11

The Raw Starch Process Enables Production of Co-product With Inventive Features

In an embodiment, the present invention provides improved access to the prolamin protein (such as zein) fraction of cereal grains. The high protein content of DDG and DDGS is useful in compounding.

Results and Discussion

Figure 14A:
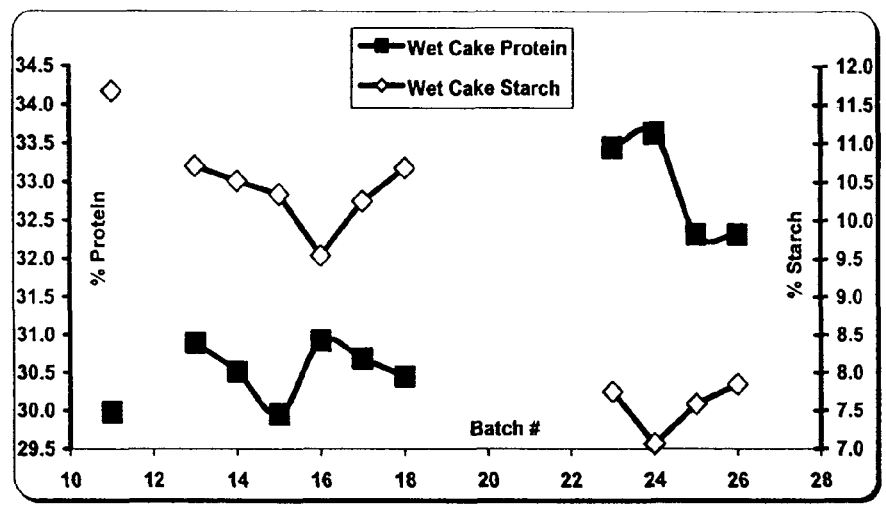
FIGS. 14A and 14B illustrate mass balance of the present process related to proximate separations during the centrifugation step of ethanol production.
Figure 14B:
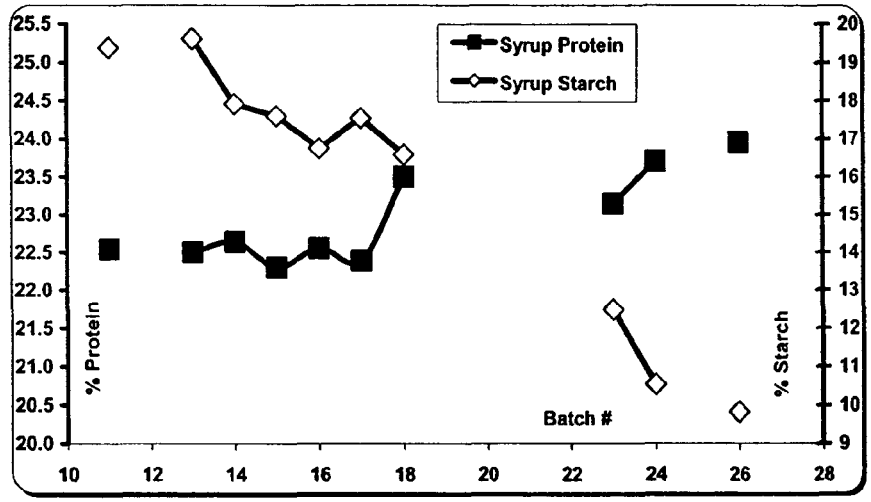

This results in DDG/DDGS with varying ratios of prolamin protein (such as zein) and residual starch. FIGS. 14A and 14B show the relationship of: wet cake, syrup starch, and protein levels. As the residual starch in the wet cake reduces the protein in the wet cake increases. This indicates an inverse relationship. A similar response occurs in the syrup fraction.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

I claim:

1. A method for producing ethanol from ground corn which method comprises:

providing an aqueous composition comprising ground corn sized such that more than 50% of the ground corn passes through a 0.5 mm screen, a fungal acid amylase and a glucoamylase under conditions which produce glucose including a pH of from 3 to 6, a temperature of from about 25° C. to about 40° C., and a solids content in said composition of from about 20 to 50 weight percent; and fermenting the glucose in the presence of a yeast under conditions which produce ethanol wherein said conditions include a pH of from about 3 to 6 and maintaining a glucose concentration in the aqueous composition of less than about 1 weight percent after 12 hours of saccharification and fermentation, wherein said method produces at least 18 volume percent ethanol.

2. The method of claim 1, wherein the aqueous composition of ground corn, fungal acid amylase and glucoamylase is maintained at a pH of from about 4.0 to 5.0.

3. The method of claim 1, wherein the amount of said fungal acid amylase to dry solids in said composition ranges from about 0.1 to about 10 fungal acid amylase units per gram of said dry solids.

4. The method of claim 3, wherein the amount of said glucoamylase to dry solids in said composition ranges from about 0.5 to about 6 glucoamylase units per gram of said dry solids.

5. A method for producing ethanol from ground corn which method comprises:

providing an aqueous composition comprising ground corn sized such that the ground corn passes through a 0.5 mm screen, a fungal acid amylase and a glucoamylase under conditions which produce glucose including a pH of from 3 to 6, a temperature of from about 25° C. to about 40° C., and a solids content in said composition of from about 20 to 50 weight percent; and fermenting said glucose in the presence of a yeast under conditions which produce ethanol wherein said conditions include a pH of from about 3 to 6 and maintaining a glucose concentration in the aqueous composition of less than about 2 weight percent;

wherein the production of glucose and the fermentation of glucose to ethanol is conducted in a simultaneous process, and further wherein said method produces at least 18 volume percent ethanol.

6. The method of claim 5, wherein the aqueous composition of ground corn, fungal acid amylase and glucoamylase is maintained at a pH of from about 4.0 to 5.0.

7. The method of claim 5, wherein the amount of said fungal acid amylase to dry solids in said composition ranges from about 0.1 to about 10 acid fungal acid amylase units per gram of said dry solids.

8. The method of claim 7, wherein the amount of said glucoamylase to dry solids in said composition ranges from about 0.5 to about 6 glucoamylase units per gram of said dry solids.

9. The method of claim 5, wherein the glucose concentration during fermentation is maintained at less than about 1 weight percent.

10. The method of claim 5, wherein during the production of ethanol, the pH is maintained at 3-4.5 during the first half of the fill cycle and at 4.5-6.0 during the second half of the fill cycle.

11. A method for producing ethanol from ground corn which method comprises:

providing an aqueous composition comprising ground corn kernels sized such that the ground corn passes through a 0.5 mm screen, a fungal acid amylase and a glucoamylase under conditions which produce glucose wherein said conditions include a pH of from 3 to 6, a temperature of from about 30° C. to about 35° C., a solids content in said composition of from about 25 to 45 weight percent, an amount of said fungal acid amylase to dry solids in said composition which ranges from about 0.1 to about 10 fungal acid amylase units per gram of said dry solids, and an amount of said glucoamylase to dry solids in said composition which ranges from about 0.5 to about 6 glucoamylase units per gram of said dry solids; and fermenting the glucose in the presence of a yeast under conditions which produce ethanol wherein said conditions comprise an initial temperature of about 35° C. which temperature is decreased during fermentation to a temperature of about 30° C., and maintaining a glucose concentration in the aqueous composition of less than about 1 weight percent after 12 hours of saccharification and fermentation wherein the production of glucose and the fermentation of glucose to ethanol is conducted in a simultaneous process, and further wherein said method produces at least 18 volume percent ethanol.

12. The process of claim 11, wherein said process is a continuous process.

13. The process of claim 11, wherein said process is conducted for a period of time up to about 96 hours.

* * * * *